United States Patent
Graft et al.

(10) Patent No.: US 6,753,957 B1
(45) Date of Patent: Jun. 22, 2004

(54) MINERAL DETECTION AND CONTENT EVALUATION METHOD

(75) Inventors: Michael Graft, Rishon-Lezion (IL); Lev Nagli, Petah Tikva (IL)

(73) Assignee: Florida Institute of Phosphate Research, Bartow, FL (US)

( * ) Notice: Subject to any disclaimer, the term of this patent is extended or adjusted under 35 U.S.C. 154(b) by 11 days.

(21) Appl. No.: 10/064,804

(22) Filed: Aug. 19, 2002

Related U.S. Application Data

(60) Provisional application No. 60/313,189, filed on Aug. 17, 2001.

(51) Int. Cl.[7] .............................................. G01N 21/63
(52) U.S. Cl. ...................................................... 356/318
(58) Field of Search .................................. 356/317, 318

(56) References Cited

U.S. PATENT DOCUMENTS

| | | |
|---|---|---|
| 3,472,375 A | 10/1969 | Mathews |
| 3,722,676 A | 3/1973 | Mathews |
| 4,365,153 A | 12/1982 | Seigel et al. |
| 4,423,814 A | 1/1984 | White |
| 5,042,947 A | 8/1991 | Potzschke et al. |
| 5,198,871 A | 3/1993 | Hill, Jr. et al. |
| 5,206,699 A | 4/1993 | Stewart et al. |
| 5,351,117 A | 9/1994 | Stewart et al. |
| 5,410,154 A | 4/1995 | Broicher et al. |
| 5,628,410 A | 5/1997 | Smith et al. |
| 5,813,543 A | 9/1998 | Gesing et al. |
| 5,847,825 A | 12/1998 | Alexander |
| 6,147,754 A | 11/2000 | Theriault et al. |
| 6,545,240 B2 * | 4/2003 | Kumar ....................... 356/318 |

* cited by examiner

Primary Examiner—F. L. Evans
(74) Attorney, Agent, or Firm—Anton J. Hopen; Smith & Hopen, P.A.

(57) ABSTRACT

A system and method for online, essentially instantaneous analyses of ore compositions on a moving belt use laser-induced break-down spectroscopy (LIBS), wherein intensity ratios of emission lines characteristic of specific minerals or ions are calculated on areas of the moving belt, with elevated contents of identifying ions or species being detectable. The ratios are derived from ions present in the sample that differentiate a first substance from a second substance, thus allowing sorting of the samples. The substance may include an ion, an element, or a compound.

7 Claims, 54 Drawing Sheets

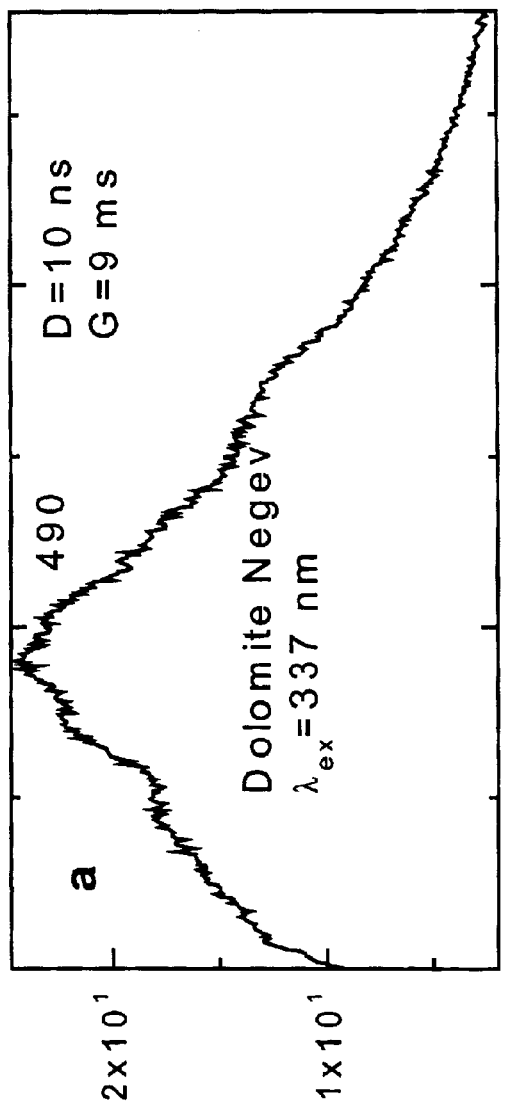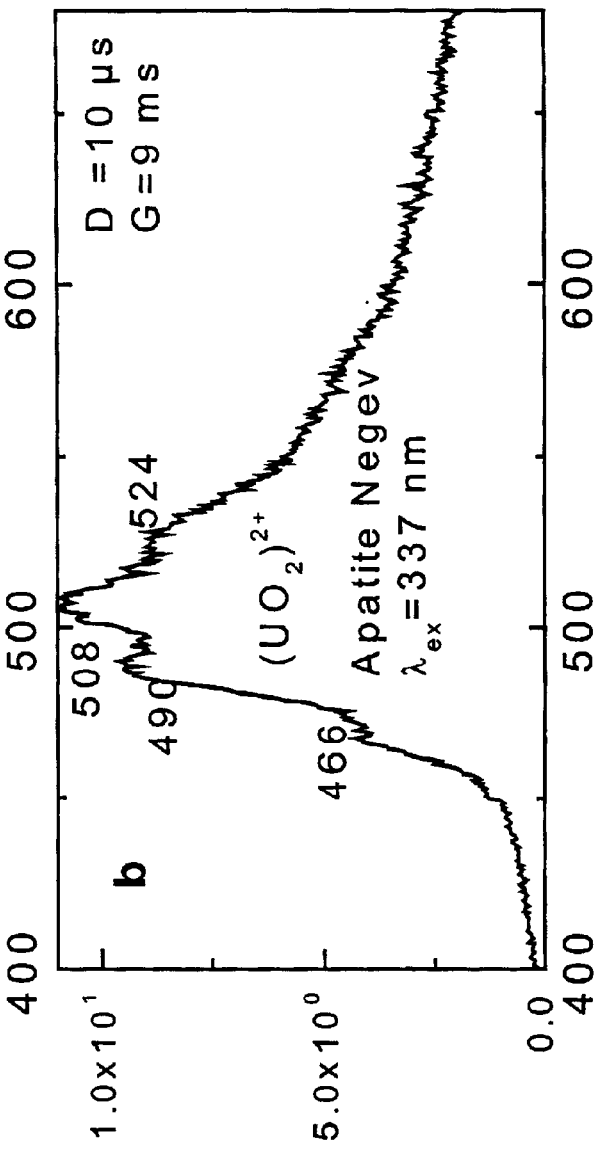
Fig. 1A
Fig. 1B

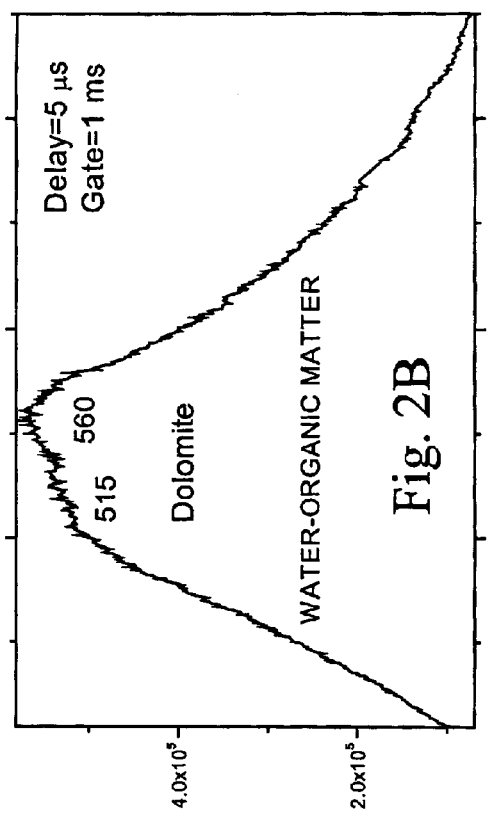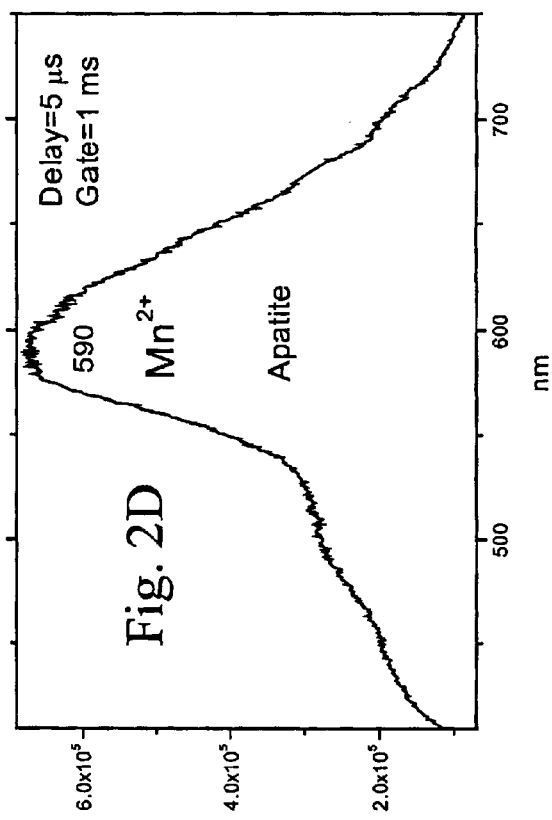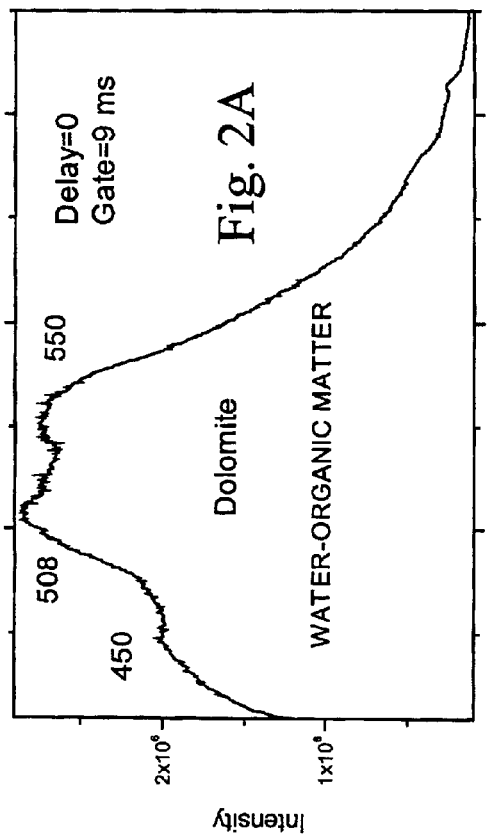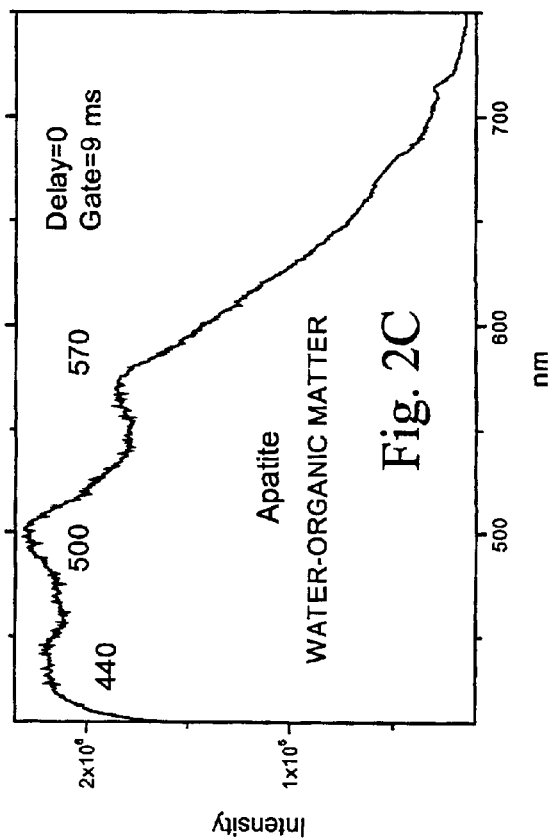

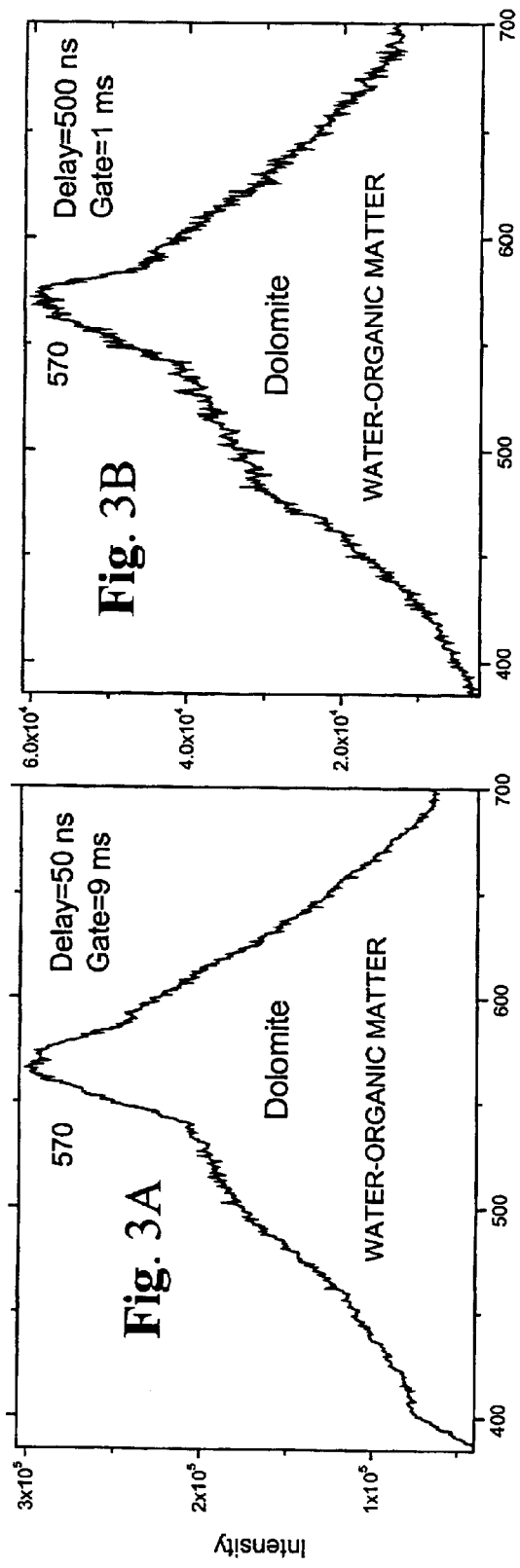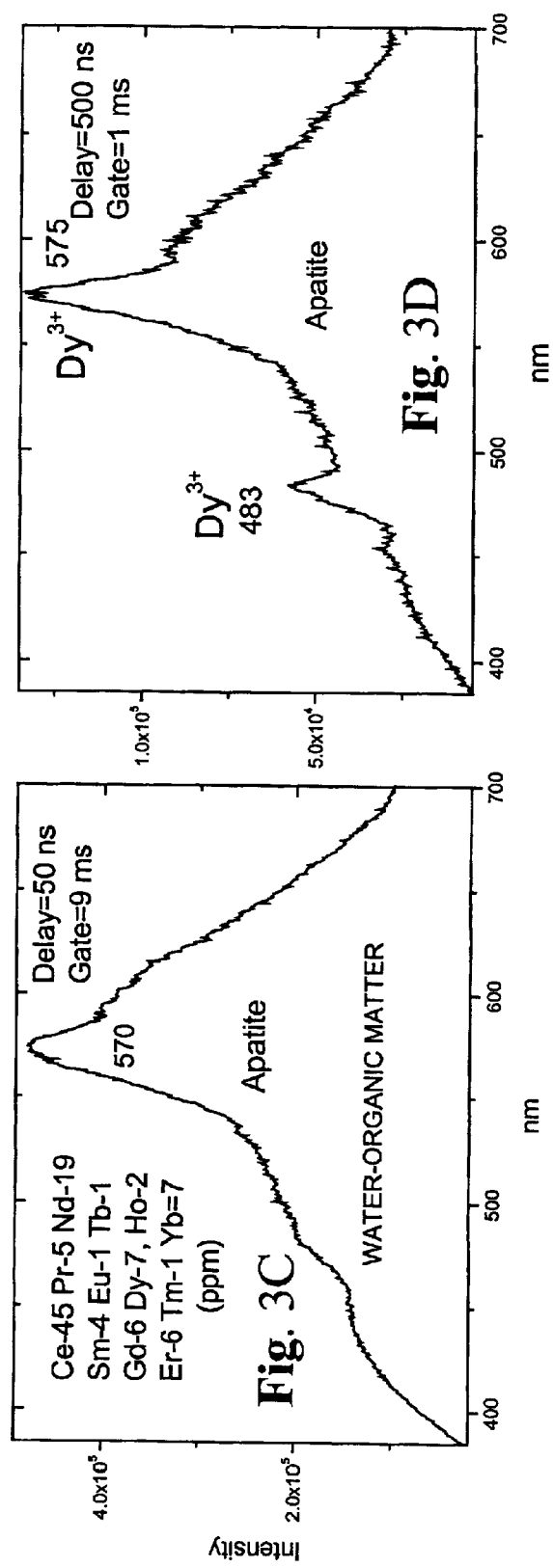

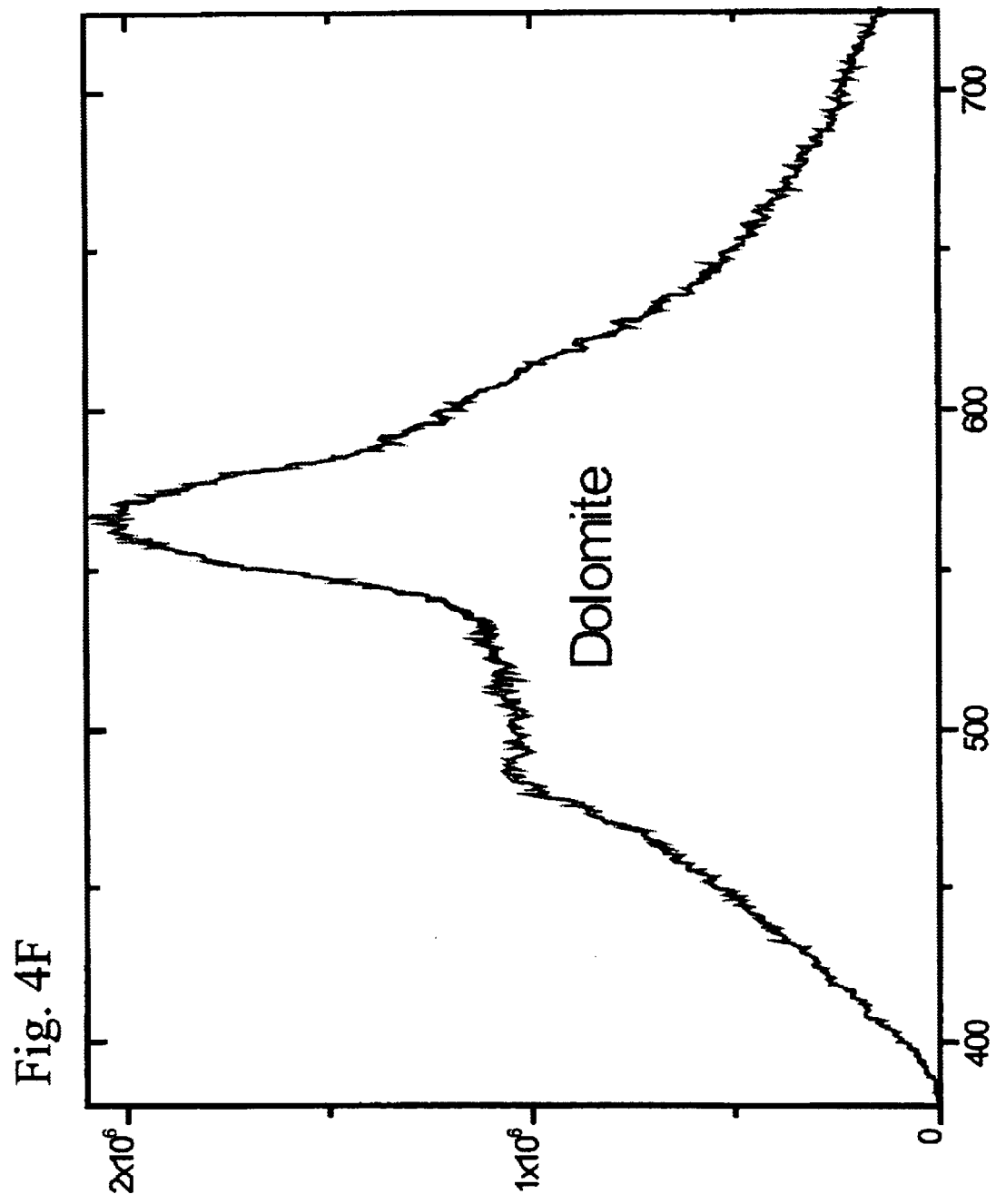

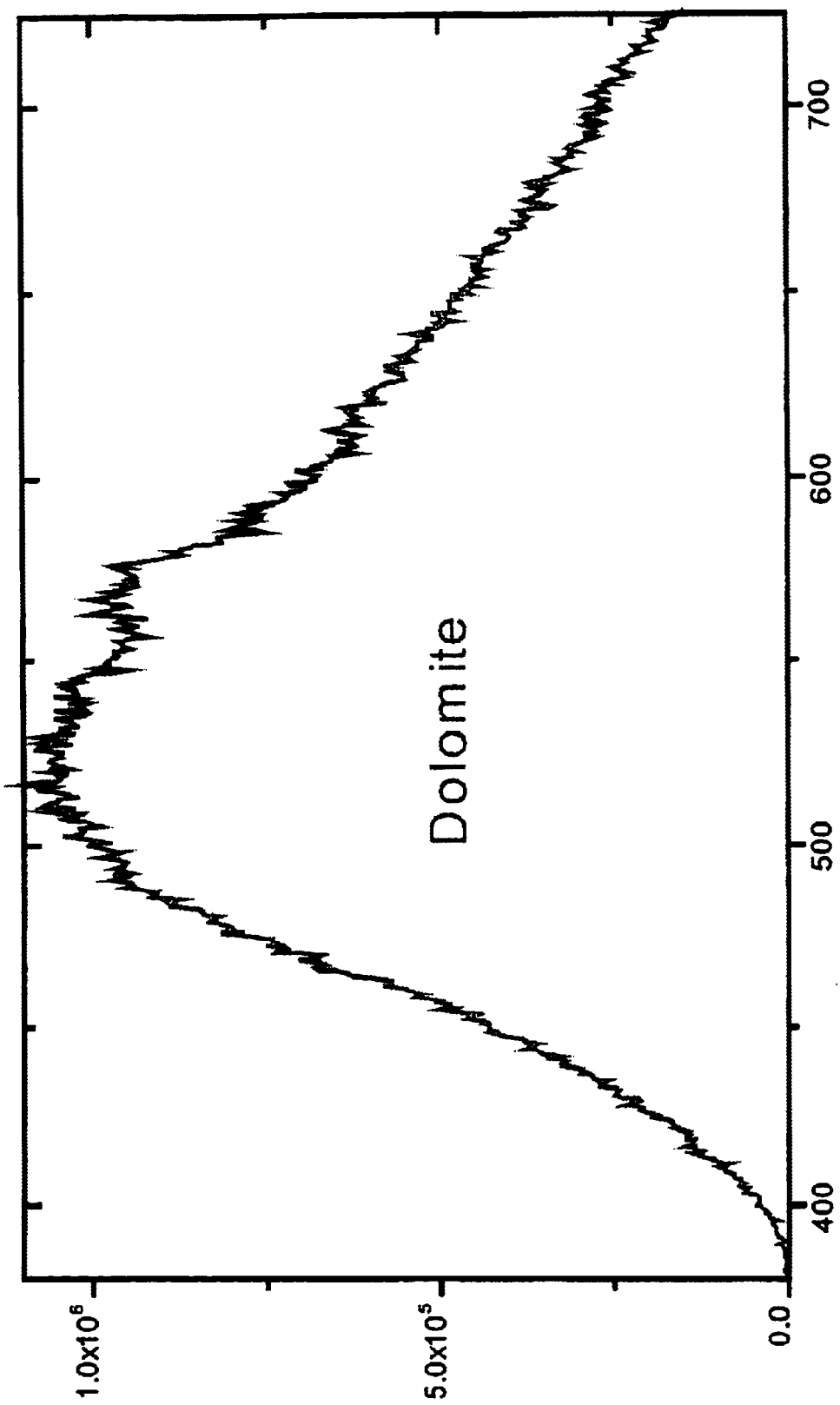

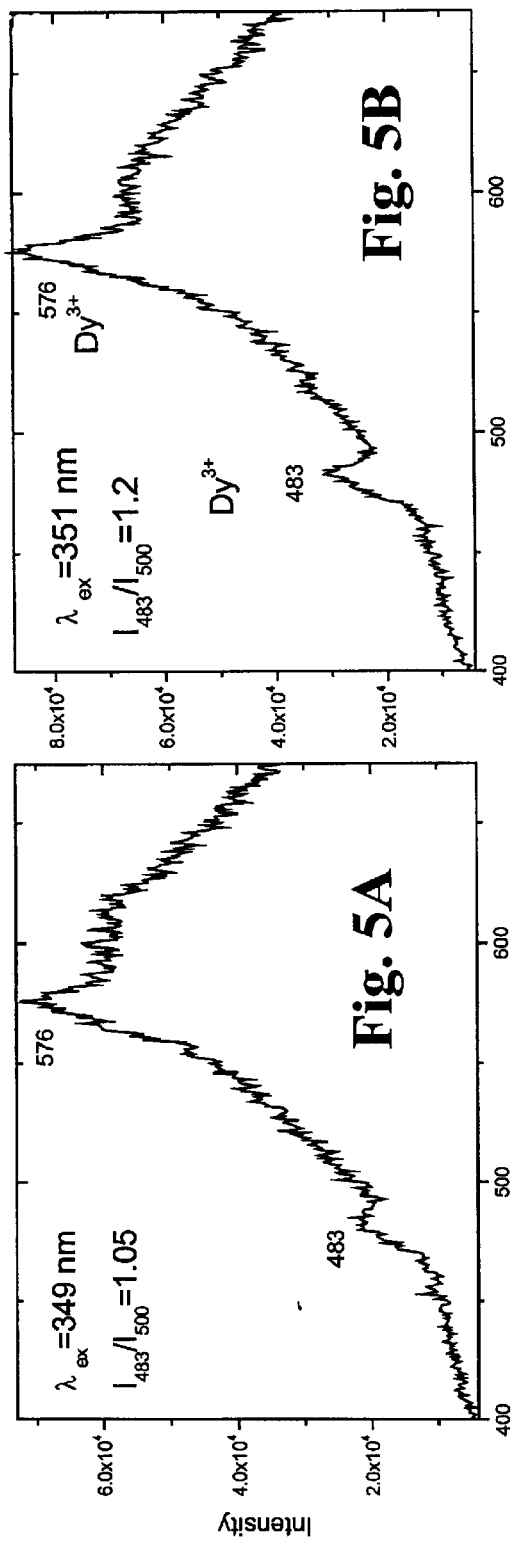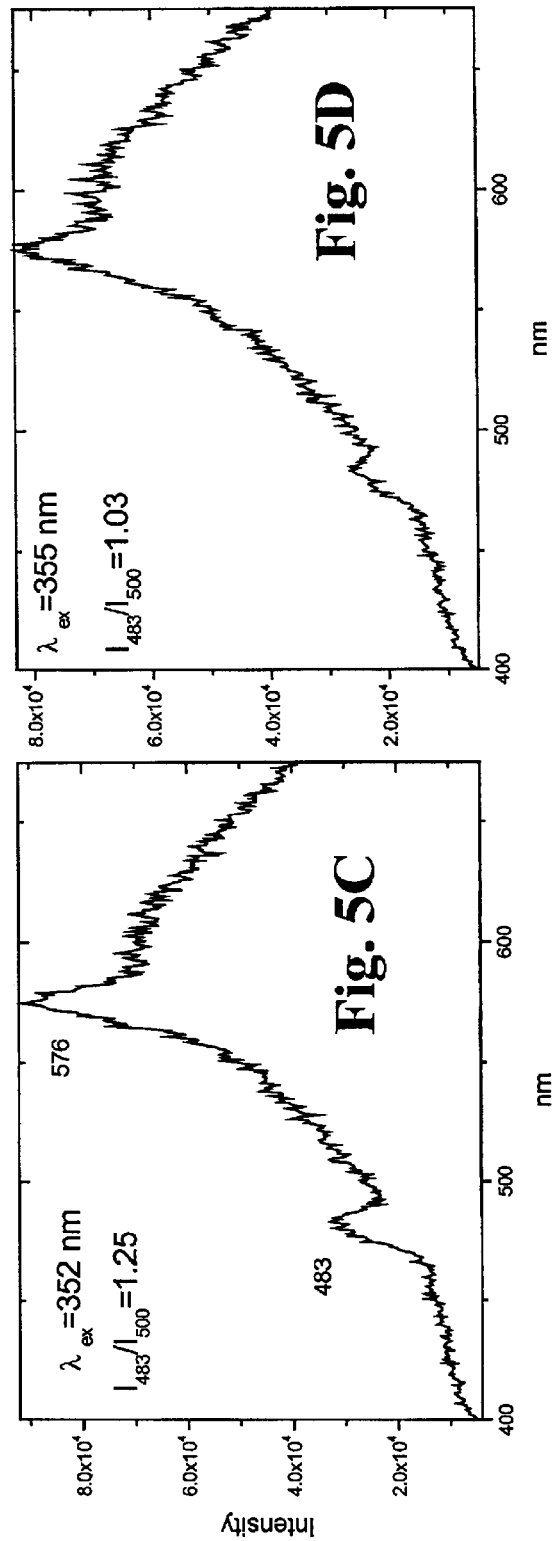

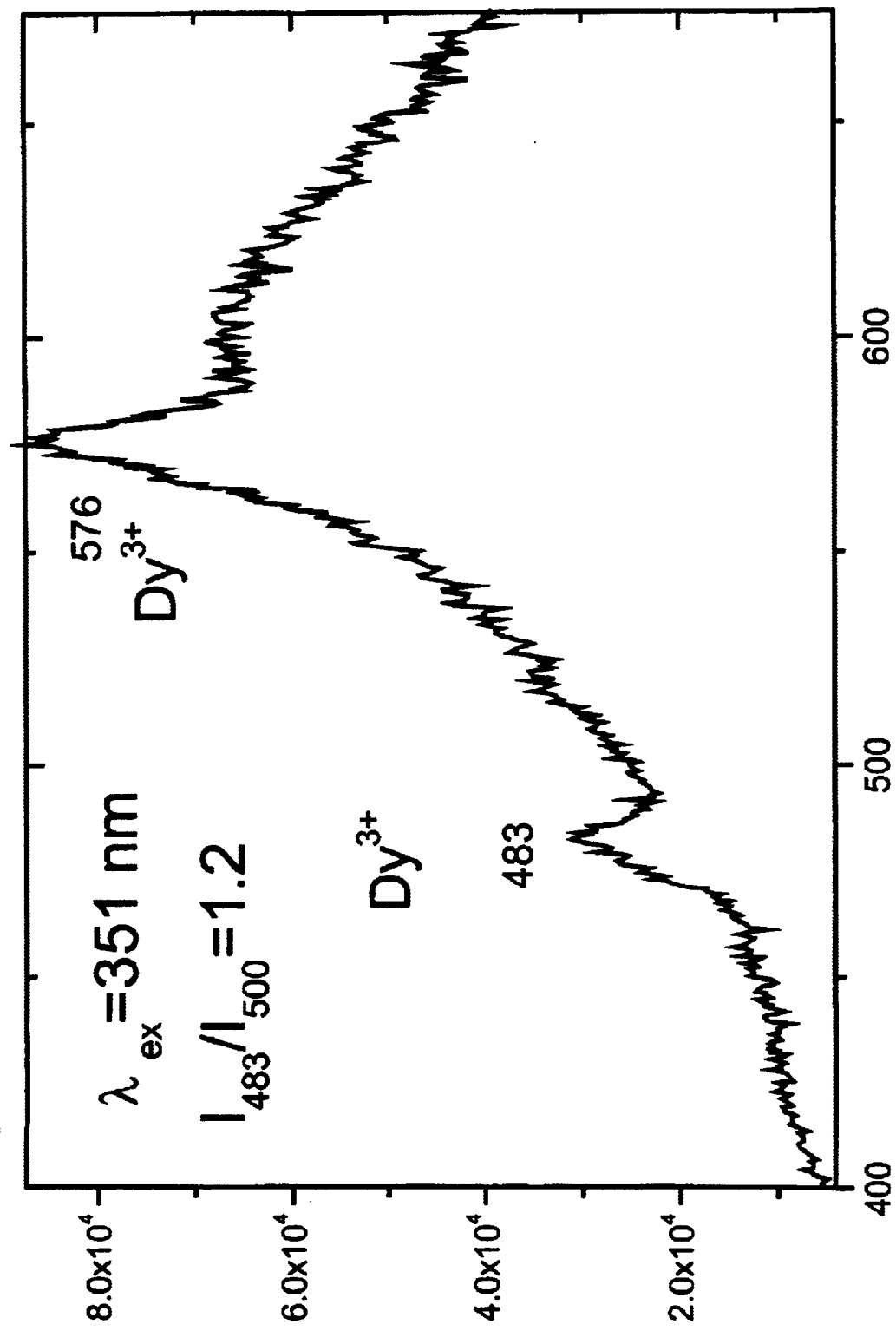

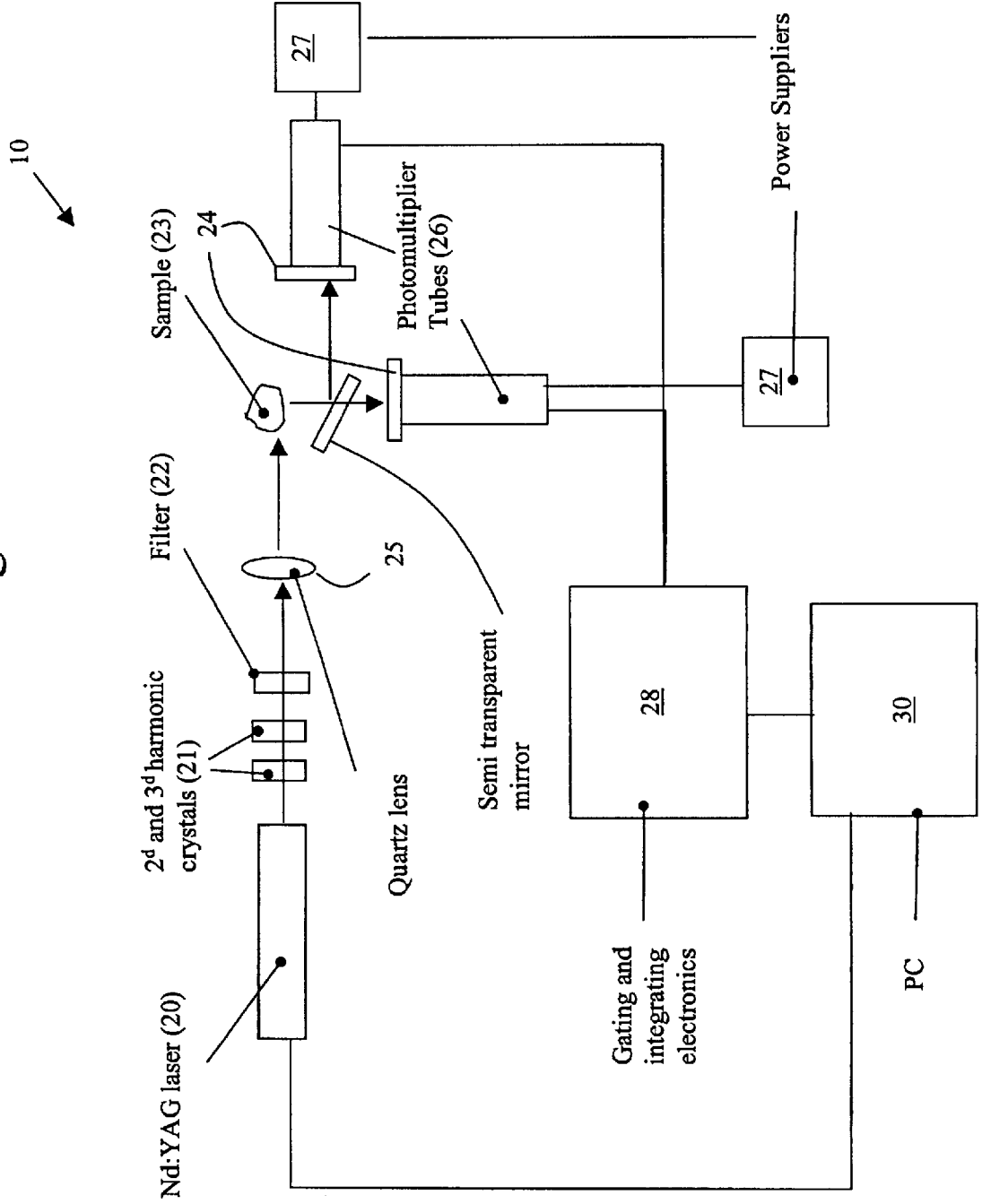

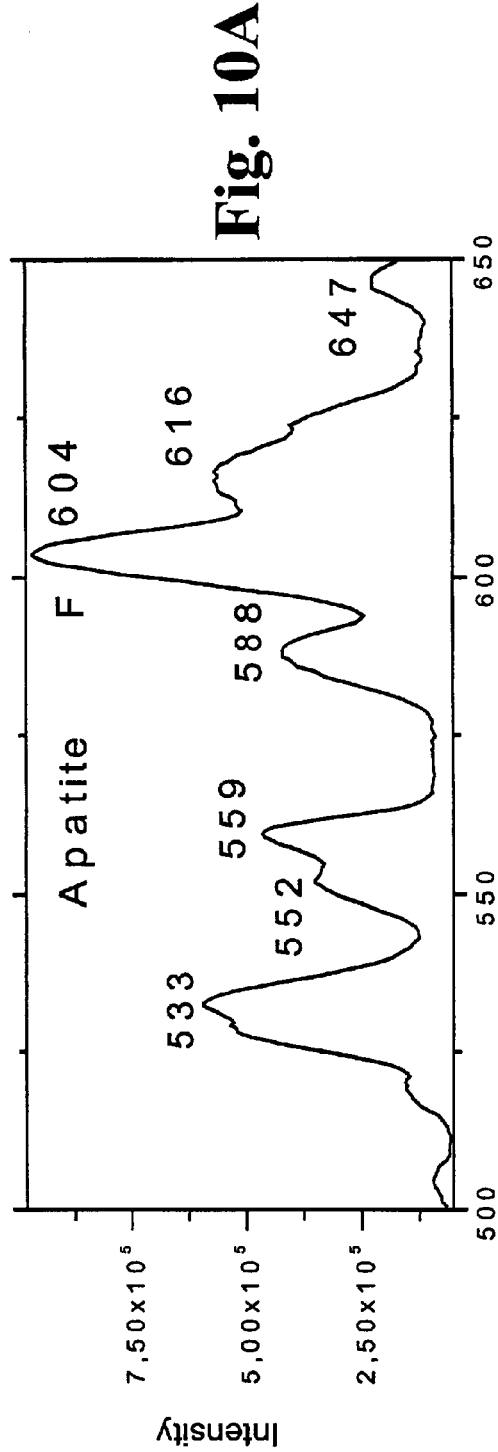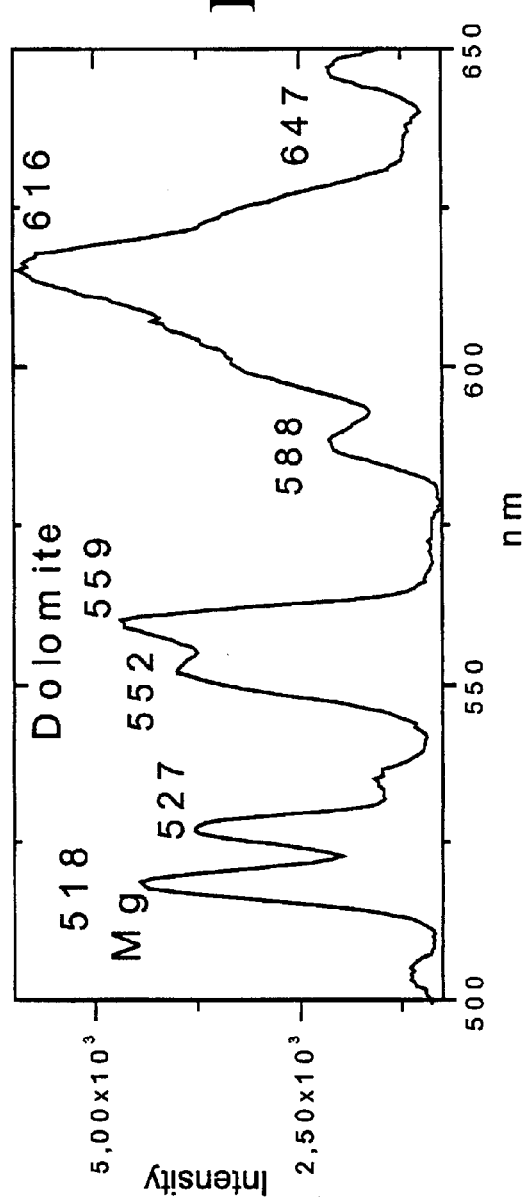
Fig. 10A
Fig. 10B

FIG. 14

| Table 1 |
|---|
| Rare-Earth Element Concentration in Florida Apatite Determined by Inductively Couple Plasma Method (ICP) |

| REE | Ce | Pr | Nd | SM | Eu | Tb | Gd | Dy | Ho | Er | Tm | Er | Yb |
|---|---|---|---|---|---|---|---|---|---|---|---|---|---|
| Ppm | 45 | 4.5 | 19 | 4 | 1.2 | 1.0 | 6 | 7 | 1.7 | 5.6 | 0.9 | 5.6 | 6.8 |

FIG. 15

| Table 2(a). $I_{580}/I_{530}$ Distinguishing Features in Apatite and Dolomite Under 337 and 355 nm Excitation | | | | | | |
|---|---|---|---|---|---|---|
| Sampling | Color | Apatite % | Apatite with $I_{580}/I_{530}$ % | Dolomite | Dolomite with $I_{580}/I_{530}$ % | Apatite without $I_{580}/I_{530}$ % |
| +1/2 | white | 41 | 67 | 59 | 0 | 33 |
|  | black | 100 |  | 0 |  |  |
| +3/8 | white | 52 | 80 | 48 | 7 | 20 |
|  | black | 83 |  | 17 |  |  |
| +.156 | white | 63 | 80 | 37 | 0 | 20 |
|  | black | 92 |  | 8 |  |  |
| +16 | white | 92 | 84 | 8 | 0 | 16 |
|  | black | 100 |  | 0 |  |  |
| Kingsford | white | 70 | 81 | 30 | 0 | 19 |
|  | black | 100 |  | 0 |  |  |
| Fort Green | white | 83 | 87 | 17 | 0 | 13 |
|  | black | 92 | 9 | 8 |  |  |

FIG. 16

| Table 2(b). Dy³⁺ Distinguishing Features in Apatite and Dolomite Under 337 and 355 nm Excitation | | | | | | |
|---|---|---|---|---|---|---|
| Sampling | Color | Apatite % | Apatite with Dy³⁺ % | Dolomite | Dolomite with Dy³⁺ % | Apatite without Dy³⁺ % |
| +1/2 | white | 41 | 67 | 59 | 0 | 33 |
|  | black | 100 |  | 0 |  |  |
| +3/8 | white | 52 | 40 | 48 | 0 | 60 |
|  | black | 83 |  | 17 |  |  |
| +.156 | white | 63 | 80 | 37 | 0 | 20 |
|  | black | 92 |  | 8 |  |  |
| +16 | white | 92 | 80 | 8 | 0 | 20 |
|  | black | 100 |  | 0 |  |  |
| Kingsford | white | 70 | 56 | 30 | 0 | 44 |
|  | black | 100 |  | 0 |  |  |
| Fort Green | white | 83 | 73 | 17 | 0 | 27 |
|  | black | 92 | 9 | 8 |  |  |

FIG. 17

| | Table 3. Chemical Analyses of the Products Received by LIBS | | | | | | | | |
|---|---|---|---|---|---|---|---|---|---|
| | PITRLS | No. Pebbles | MgO | $P_2O_5$ | BPL | F | $Fe_2O_3$ | $Al_2O_3$ | Insoluble |
| 1 | "Bad" | 20 | 2.21 | 3.48 | 7.60 | 0.37 | 1.11 | 2.23 | 70.40 |
| | "Good" | 31 | 0.46 | 28.61 | 62.52 | 3.58 | 0.74 | 1.08 | 12.94 |
| 2 | "Bad" | 18 | 2.50 | 5.93 | 12.96 | 0.52 | 1.06 | 3.84 | 63.92 |
| | "Good" | 33 | 0.44 | 28.11 | 61.42 | 3.33 | 0.78 | 0.75 | 13.33 |
| 3 | "Bad" | 13 | 4.6 | 4.49 | 9.81 | 0.3 | 1.27 | 2.01 | 56.46 |
| | "Good" | 45 | 0.34 | 27.37 | 59.80 | 3.42 | 0.76 | 1.42 | 14.24 |

FIG. 18

Table 4 shows LIBS analysis of the same samples.

| Table 4. LIBS Data Using PMP Setup | | | | | |
|---|---|---|---|---|---|
| Sample | | $I_{600}$ | 1520 | $I_{600}/I_{520}$ | Mineral |
| 1/2 | 4 | 18.2 | 4.8 | 3.8 | Apatite |
| 1/2 | 5 | 6.4 | 3.2 | 2 | Dolomite |
| 1/2 | 6 | 11.6 | 6.6 | 1.8 | Dolomite |
| 1/2 | 7 | 15.6 | 2.1 | 7.8 | Apatite |
| 1/2 | 8 | 8.8 | 4.2 | 2.1 | Dolomite |
| 1/2 | 9 | 14.4 | 9 | 1.6 | Dolomite |
| 1/2 | 10 | 25 | 4.4 | 5.7 | Apatite |
| 1/2 | 12 | 10.6 | 1.7 | 6.2 | Apatite |
| 1/2 | 13 | 15.6 | 2.1 | 7.8 | Apatite |
| 1/2 | 14 | 11 | 2.5 | 4.4 | Apatite |
| 1/2 | 15 | 1.8 | 0.8 | 2.3 | Apatite |
| 3/8 | 9 | 7 | 4.6 | 1.5 | Dolomite |
| 3/8 | 10 | 19.4 | 3 | 6.5 | Apatite |
| 3/8 | 11 | 4.2 | 4.2 | 1 | Dolomite |
| 3/8 | 13 | 4.6 | 2.3 | 2 | Dolomite |
| 3/8 | 15 | 7.5 | 1.2 | 6.2 | Apatite |
| 3/8 | 16 | 11.4 | 1.4 | 8.1 | Apatite |
| 3/8 | 17 | 16 | 2.2 | 7.3 | Apatite |
| 3/8 | 18 | 19 | 3.6 | 5.3 | Apatite |
| 3/8 | 19 | 18 | 2.4 | 7..5 | Apatite |
| 3/8 | 20 | 13 | 1.6 | 8.1 | Apatite |

MINERAL DETECTION AND CONTENT EVALUATION METHOD

RELATED APPLICATIONS

This application is a Continuation-in-Part and claims priority to U.S. patent application Ser. No. 60/313,189 filed on Aug. 17, 2001.

BACKGROUND OF INVENTION

1. Field of the Invention

This invention deals with the evaluation of mineral ores and the identification of components in the ores and the ability to selectively determine with a high degree of accuracy the content of such ores. In specific, by using the apparatus and method of the present invention, wanted or unwanted chemical species can be identified, thus making this an effective screening tool for rapid analysis of ores in mining applications. It is also anticipated that the present invention may be deployed in any application for which the identity of a chemical species is sought.

2. Description of Related Art

The need for instantaneous evaluation of mineral contents on moving belt systems has led to the necessity of remote sensing techniques to instantly differentiate between corresponding minerals to select desired mineral ores from those that are undesirable. This selection may be based on selective influence of the different kinds of irradiation on those minerals, whereby discrete pebbles are analyzed within a fraction of a second for a characteristic that can distinguish between "accept" and "reject" fractions. At present when dealing with moving belt systems, mineral evaluation is mainly performed using photometric, radiometric, steady-state luminescence, gamma-ray or X-ray fluorescence, and neutron absorption characteristics are mainly used for mineral evaluation.

U.S. Pat. No. 4,365,153 to Siegel describes the detection of certain minerals, including zinc, tungsten, fluorine, molybdenum, mercury, and other metals using a photoluminescence method. The basis of selective detection is that the lifetimes of photoluminescent emissions of many industrial minerals are much longer than the lifetimes of photoluminescent emissions of background materials that are likely to occur at the Earth's surface. The measurement of the photoluminescent response measured here is based on a response-retention factor and not on a direct readout at the time of irradiation. The detection here is based on taking a delayed readout to identify the minerals of economic interest after enough time has elapsed to enable unwanted sources of photoluminescence to decay.

Broicher (U.S. Pat. No. 5,410,154) describes detection of quality alterations contained in goods as they progress on a moving belt. The use of laser-induced luminescence, reflected light, and temperatures including detection of signal intensity and the fading behavior of the signals in definite spectral ranges is disclosed. This approach was also used by AIS Sommer GmbH of Germany, in their laser-induced fluorescence (LIF) analyzer for quality control in minerals and mineral processing. The LIF analyzer includes two light detector systems with three photomultipliers each, which evaluate three spectral bands in two time windows each. Such a system was employed in the Kirumna phorphorus iron ore mine in Sweden.

The limitation of LIF analysis is that its accuracy depends on the complexity of the composition of the ore and the concentration and fluorescence properties of the critical minerals in relation to all the other minerals present.

Another approach to differentiation of samples is described by White (U.S. Pat. No. 4,423,814). Here the natural luminescence of the accept and reject fractions is similar. The basis of separation of magnesium-bearing ore particles is obtained by first conditioning the exposed magnesium-rich mineral with a surface coupling agent of hydroxquinoline, then irradiating the conditioned ore to excite and induce fluorescence and then effecting separation of the magnesium-rich minerals from the lean ore particles by detection of the difference of the intensity of the fluorescence. This method detects ores having high magnesium contents on the surfaces of the pebbles.

Many similar methods have been used in the past to screen samples based on physico-chemical properties. Another example of this is selective flotation of phosphates and dolomites. As stated above, the difficulties of selective flotation of phosphates with high magnesium content are explained by similar physico-chemical properties of phosphates and dolomites. This problem exists also with other ores, thus making it desirable within the mining field to find separation systems that can quickly distinguish between wanted and unwanted ore fractions.

Alexander (U.S. Pat. No. 5,847,825) describes a method and apparatus for detection and concentration measurement of trace metals using laser-induced breakdown spectroscopy (LIBS). LIBS is a simple, rapid, real-time analytical technique based on the analysis of the spectral emission from laser-induced sparks or plasma. Pulsed laser radiation is first focused to a small spot on the sample material. When power densities exceed hundreds of $MW/cm^2$, a high-temperature, high-electron-density laser microplasma is formed. The temperature of this plasma initially is very hot: $10^4$ to $10^7$ □ C. At such a high temperature, any sample material is broken down, vaporized and ionized. As the plasma cools down to the point when neutral atoms in excited states are formed, the excited species relax and emit optical energy at characteristic wavelengths. The emission can then be spectrally resolved to identify the elemental species that are present in the sample based on the presence of the characteristic lines.

It has been shown that LIBS is practical in situations, which require very fast, real-time measurements with no sample preparation. One such method is a penetrometer system for subsurface spectral analyses; such a system being described in Theriaul et al. (U.S. Pat. No. 6,147,754). Here, elemental identification using a cone penetrometer unit is achieved by using atomic spectral analyses of contaminants that are stimulated by a laser-induced breakdown of the soil containments to be determined.

Potzchke (U.S. Pat. No. 5,042,947) describes a scrap detection system using another LIBS system. Here a method and apparatus is disclosed whereby metal particles are detected in the context of being contained in compositions of alloying metals. Sorting of metal particles is effected by a plasma process, which cleans and then identifies the particles of interest. However, these metal particles are not in ion form as are those contained in mineral samples.

SUMMARY OF INVENTION

It is therefore an object of the invention to provide a LIBS system that is capable of detection of trace metals in an ore sample, such metals even being in an ionic species form.

It is a further object of the invention to provide a low-cost multi-element analysis system adapted to being compact and requiring no sample preparation.

It is another object of the invention to provide a system for sorting mineral ore samples which allows for rapid sorting of minerals in a moving belt system.

The present invention comprises a system and a method for mineral sorting and detecting, including remote sensing, and more particularly, for real-time detection and content evaluation of minerals or trace concentrations of elements in materials as they are conveyed on a moving belt. The instant invention employs a laser-induced breakdown spectroscopy (LIBS) system wherein intensity ratios of the emission lines characteristic for specific elements or minerals enable detection of the same while on a moving belt. Because associated minerals have different chemical compositions, namely, major or minor elements, the relative intensities, defined by their characteristic spectral lines, enables all phases to be consistently identified and assessed within a short time that is consistent with both LIBS and the moving belt system.

The steps to the invention include establishing a spectral signature ratio for at least one predetermined substance, the signature having a first intensity at a first wavelength relative to a second intensity at a second wavelength, applying pulsed laser energy to the mineral sample whereby plasma is produced, obtaining the spectral intensity of the plasma at the first and second wavelengths, and calculating the ratio of the spectral intensity at the first wavelength by the spectral intensity at the second wavelength whereby the presence or absence of the substance may be resolved.

It should be noted that the present invention permits the mineral sample to be analyzed substantially in real-time while in transit, such as moving on a conveyor belt. In a preferred embodiment, the steps include providing a computational processor and providing a radiation detector adapted to obtain the spectral intensity of the plasma. A database of spectral signatures for at least one substance is provided along with an output means communicatively coupled to the processor. The radiation detector, processor, and database are all communicatively coupled together wherein the spectral intensity is obtained by the radiation detector and measured values for the first and second wavelengths are passed onto the processor which calculates and compares the ratio to the database of spectral signatures and communicates the results to the output means. In another embodiment of the invention, the step of obtaining of the spectral intensity of the plasma may be time-gated to provide further discrimination of the sample's plasma.

The present invention is not limited to minerals, but to any compound for which the identity is sought in rapid analytical fashion. For example, food products (i.e., ingestible matter) may be rapidly analyzed for compounds or elements of interest.

BRIEF DESCRIPTION OF DRAWINGS

FIGS. 1A, 1B are examples of laser-induced time-resolved luminescence of dolomite and phosphate rock, respectively. Excitation by nitrogen laser at 337 nm; repetition rate 500 Hz, E=50 mJ, delay=10 $\mu$s, gate=500 $\mu$s, $\Delta\lambda_{lum}$=450–525 nm.

FIGS. 2A–2D are spectra of Florida dolomite (FIG. 2A, delay=0, gate=9 ms; FIG. 2B, delay=5 $\mu$s, gate=1 ms) and apatite (FIG. 2C, delay=0, gate=9 ms; FIG. 2D, delay=5 $\mu$s, gate=1 ms) at $\lambda$=337 nm excitation.

FIGS. 3A–3D are luminescence spectra of Florida dolomite (FIG. 3A, delay=50 ns, gate 9 ms; FIG. 3B, delay=500 ns, gate=1 ms) and apatite (FIG. 3C, delay=50 ns, gate=9 ms; FIG. 3D, delay=500 ns, gate=1 ms) under $\lambda$=355 nm excitation.

FIGS. 5A–5D are excitation spectra of $Dy^{3+}$ (10 ppm) in Florida phosphate (FIG. 5A, $\lambda_{exc}$=349 nm; FIG. 5B, $\lambda_{exc}$=351 nm, $I_{482}//_{500}$=1.75; FIG. 5C, $\lambda_{exc}$=352 nm; FIG. 5D, $\lambda_{exc}$=355 nm, $I_{482}//_{500}$=1.45).

FIGS. 6A–6D are excitation spectra of $Dy^{3+}$ (2 ppm) in Florida phosphate (FIG. 6A, $\lambda_{exc}$=349 nm, $I_{483}//_{500}$=1.05; FIG. 6B, $\lambda_{exc}$=351 nm, $I_{483}//_{500}$=1.2; FIG. 6C, $\lambda_{exc}$=352 nm, $I_{483}//_{500}$=1.25; FIG. 6D, $\lambda_{exc}$=355 nm, $I_{483}//_{500}$=1.03).

FIG. 7 is a schematic of the system of the instant invention.

FIG. 9B, dolomite; FIG. 9C, calcite; FIG. 9D, quartz).

FIGS. 10A,B are LIBS spectra of Florida apatite (FIG. 10A) and dolomite (FIG. 10B).

FIG. 11C, delay=500 ns, gate=9 ms, $I_{606}//_{518}$=8.6) and dolomite (FIG. 11B, delay=0, gate=9 ms, $I_{606}//_{518}$=0.3; FIG. 11D, delay=0, gate=500 ns, $I_{606}//_{518}$=0.1).

FIG. 12C, delay=1 $\mu$s, gate=9 ms, $I_{606}//_{519}$=19) and dolomite (FIG. 12B, delay=0, gate=9 ms, $I_{606}//_{519}$=0.35; FIG. 12D, delay=0, gate=500 ns, $I_{606}//_{519}$=0.2).

FIG. 13B, danburite, $CaB_2(SiO_4)_2$; FIG. 13C, fluorite, $CaF_2$; FIG. 13D, galenite, PbS; FIG. 13E, hydrozinkite, $Zn_5(CO_3)_2(OH)_6$; FIG. 13F, magnesite, $MgCO_3$; FIG. 13G, quartz, $SiO_2$; FIG. 13H, willemite, $Zn_2SiO_4$; FIG. 13I, wulfenite, $PbMoO_4$; FIG. 13J, zircon, $ZrSiO_4$].

FIG. 14 is a table showing Rare-Earth concentration in Florida Apatite determined by Inductivity Coupled Plasma Method (ICP).

FIG. 15 is a table showing $I_{580}/I_{530}$ distinguishing features in Apatite and Dolomite under 337 and 355 nm excitation.

FIG. 16 is a table showing $Dy^{3+}$ distinguishing features in Apatite and Dolomite under 337 and 355 nm excitation.

FIG. 17 is a table showing chemical analyses of the products received by LIBS.

FIG. 18 is a table showing LIBS data using PMP setup.

DETAILED DESCRIPTION

Figure 4A:
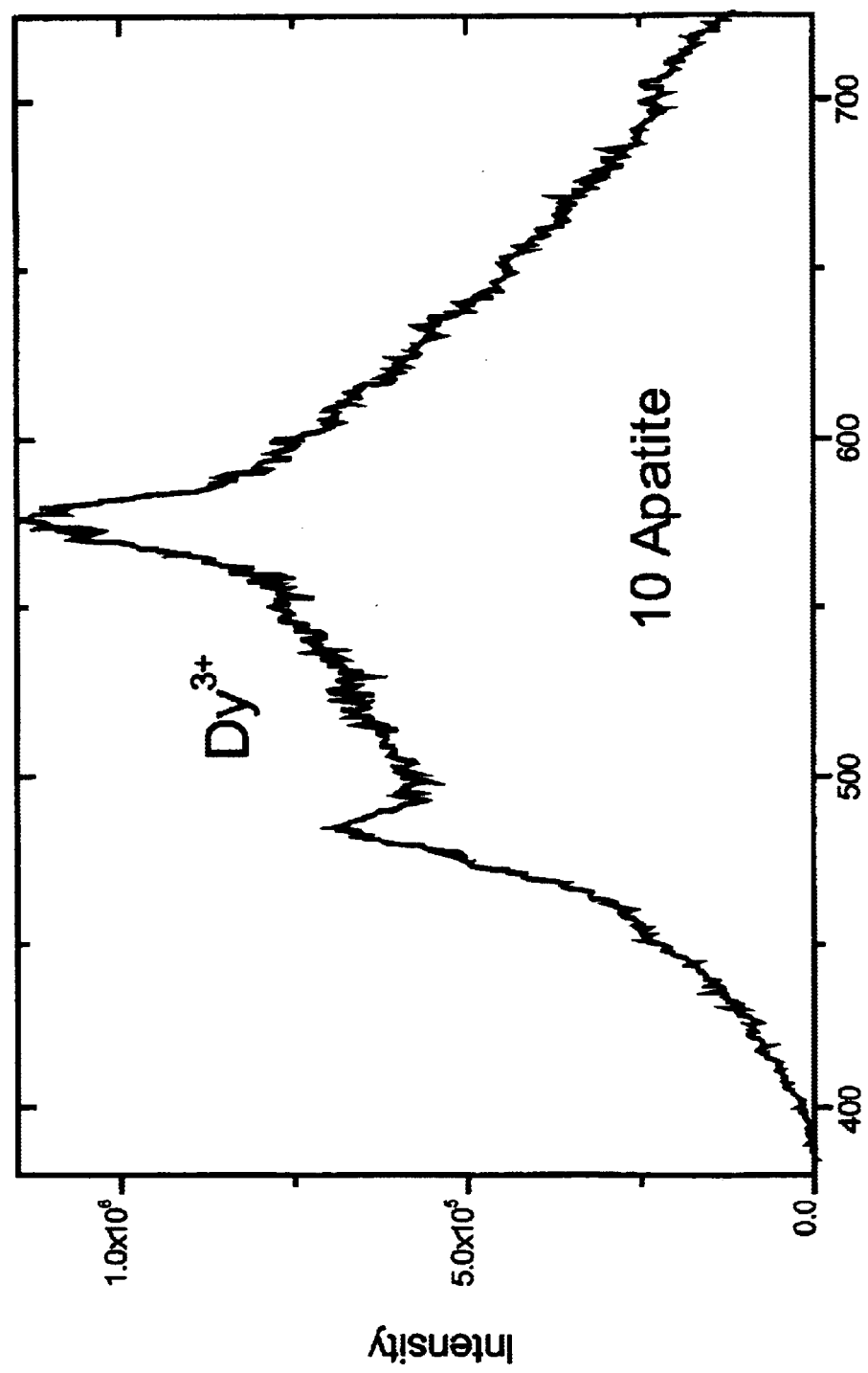
FIGS. 4A–4P are spectra of one set of fractions by under 355-nm excitation, identified as fraction +½.
Figure 4B:
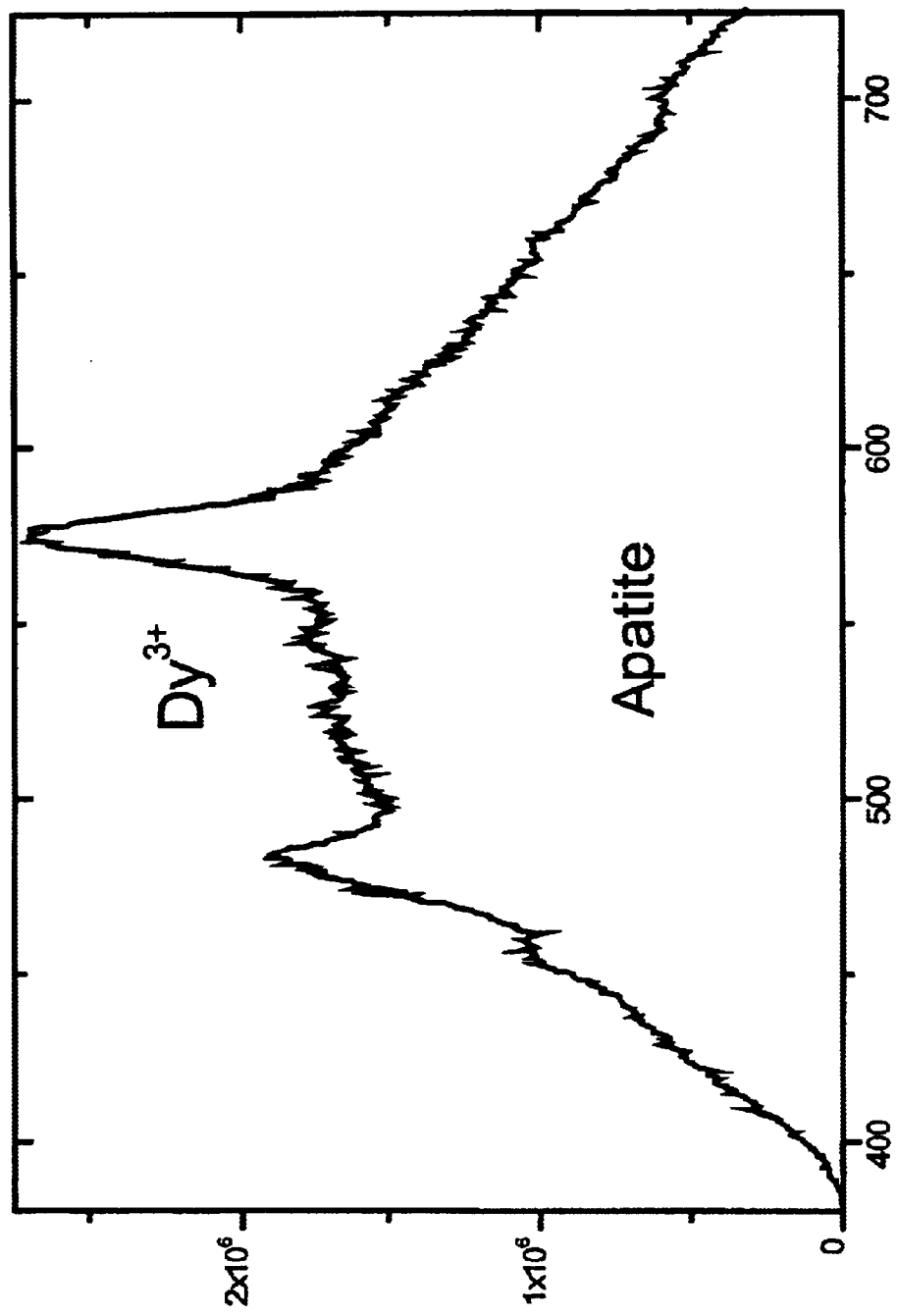
Figure 4C:
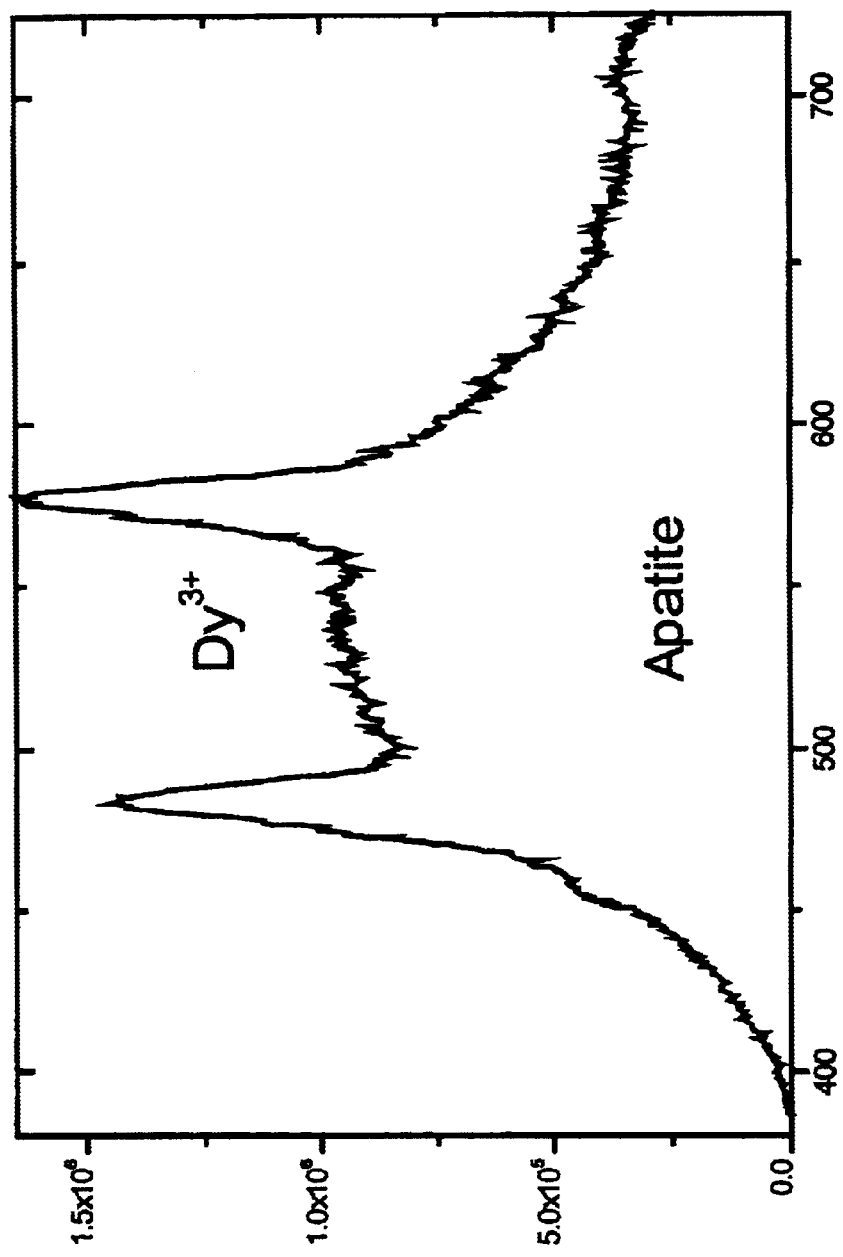
Figure 4D:
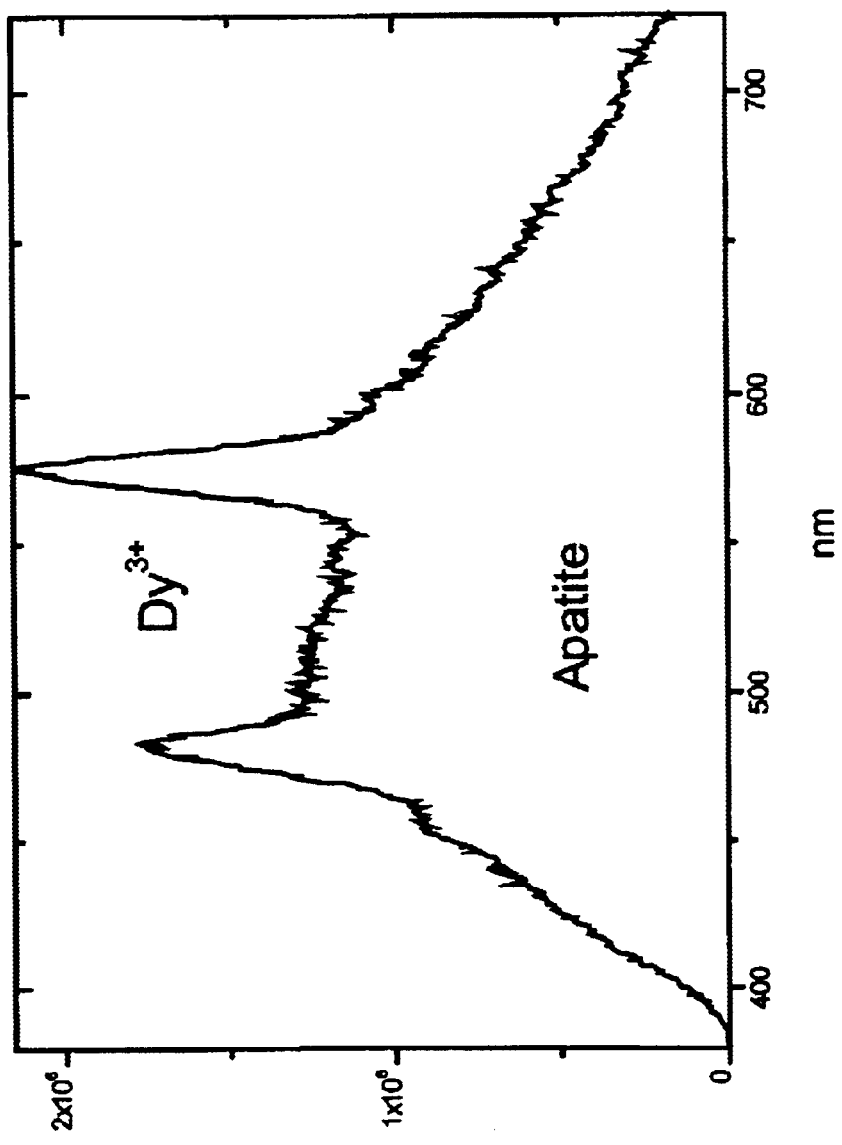
Figure 4E:
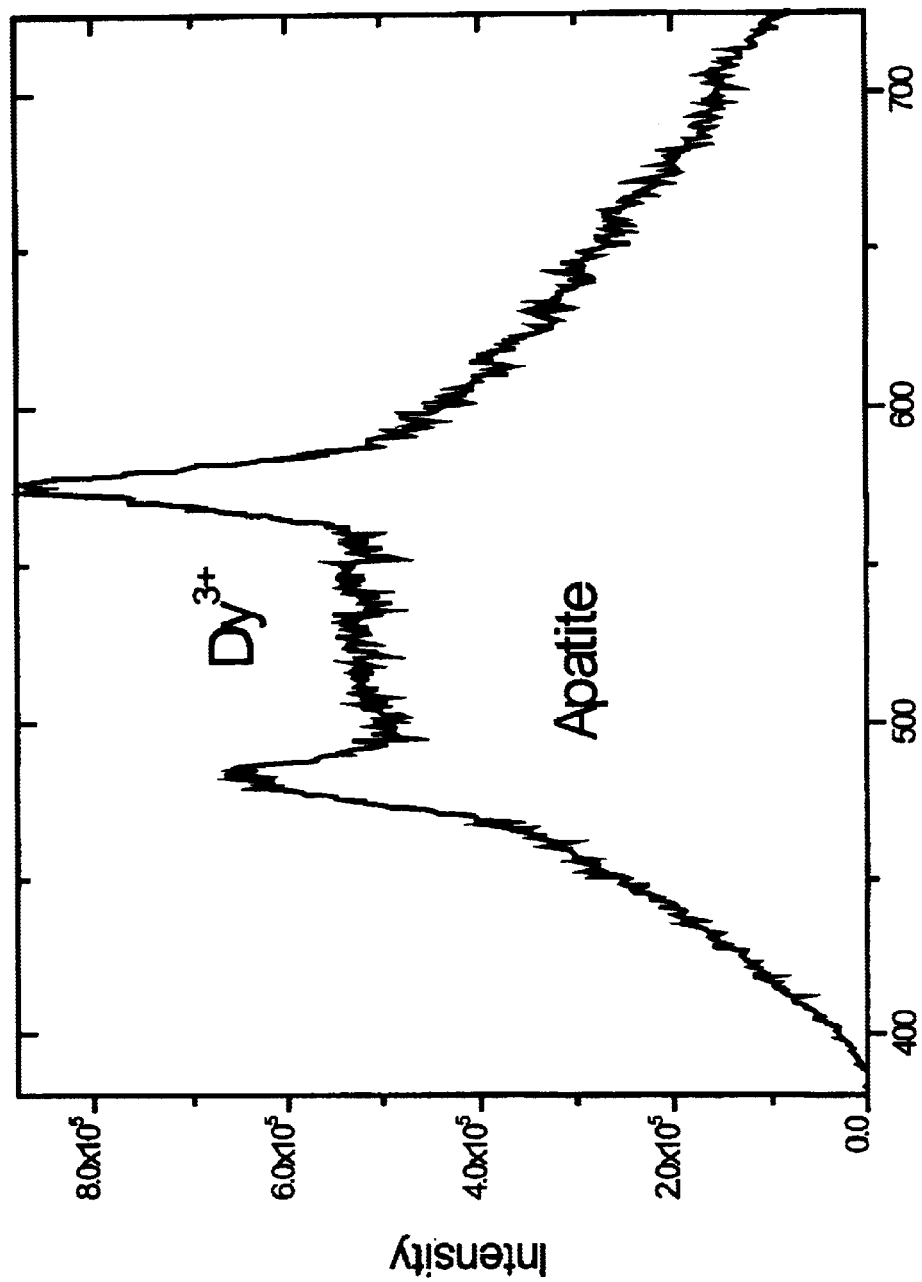
Figure 4G:
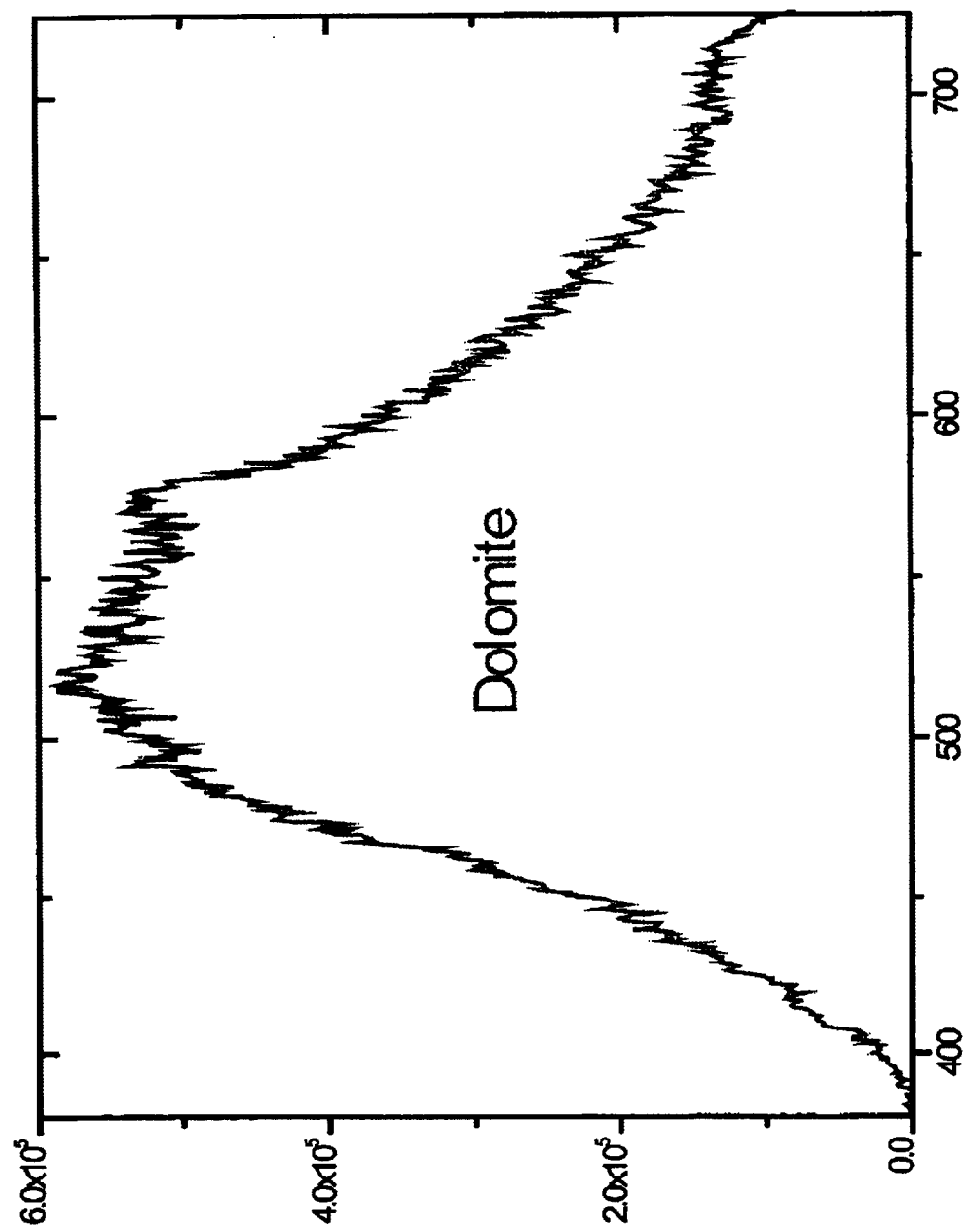
Figure 4I:
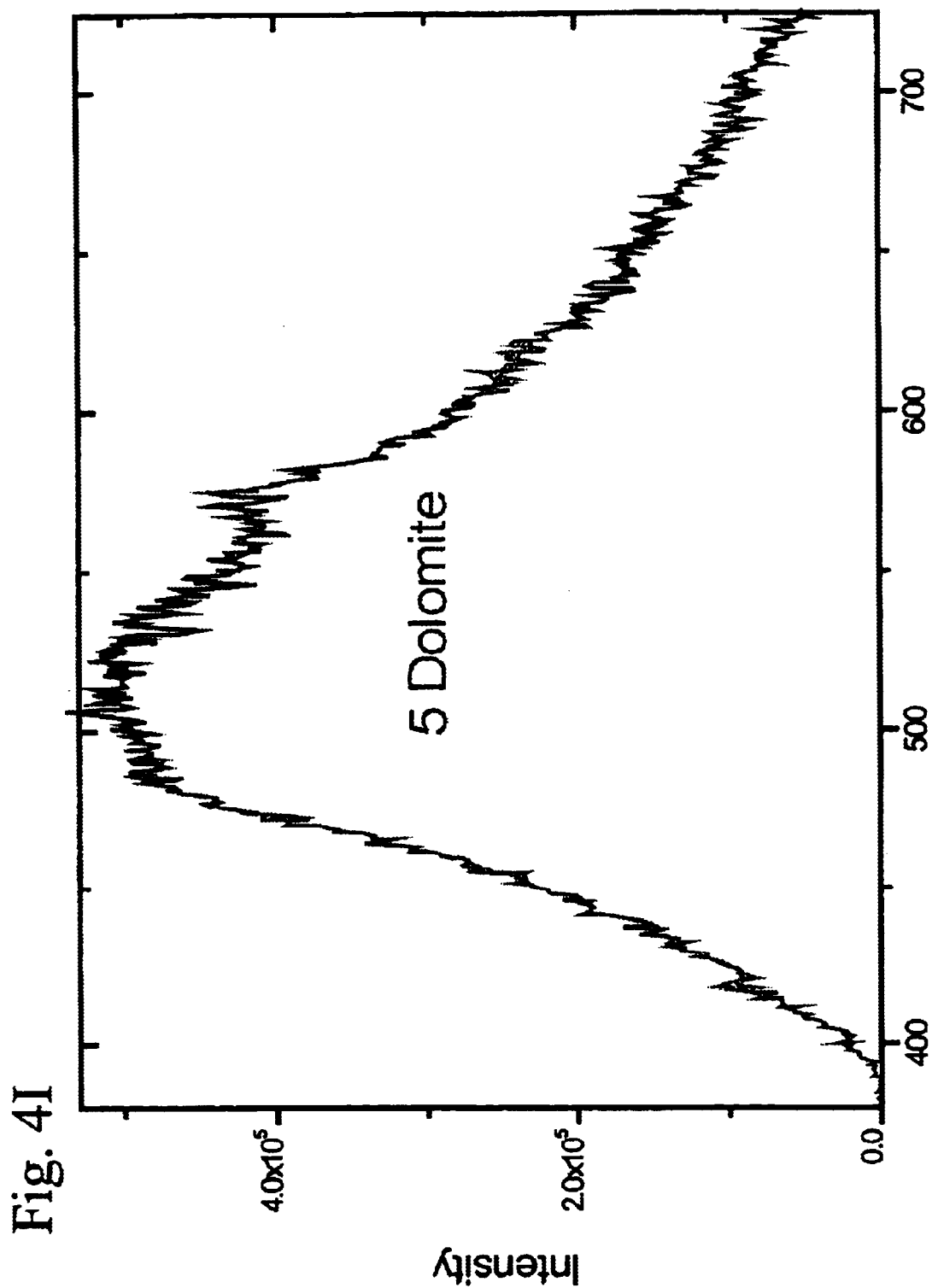
Figure 4J:
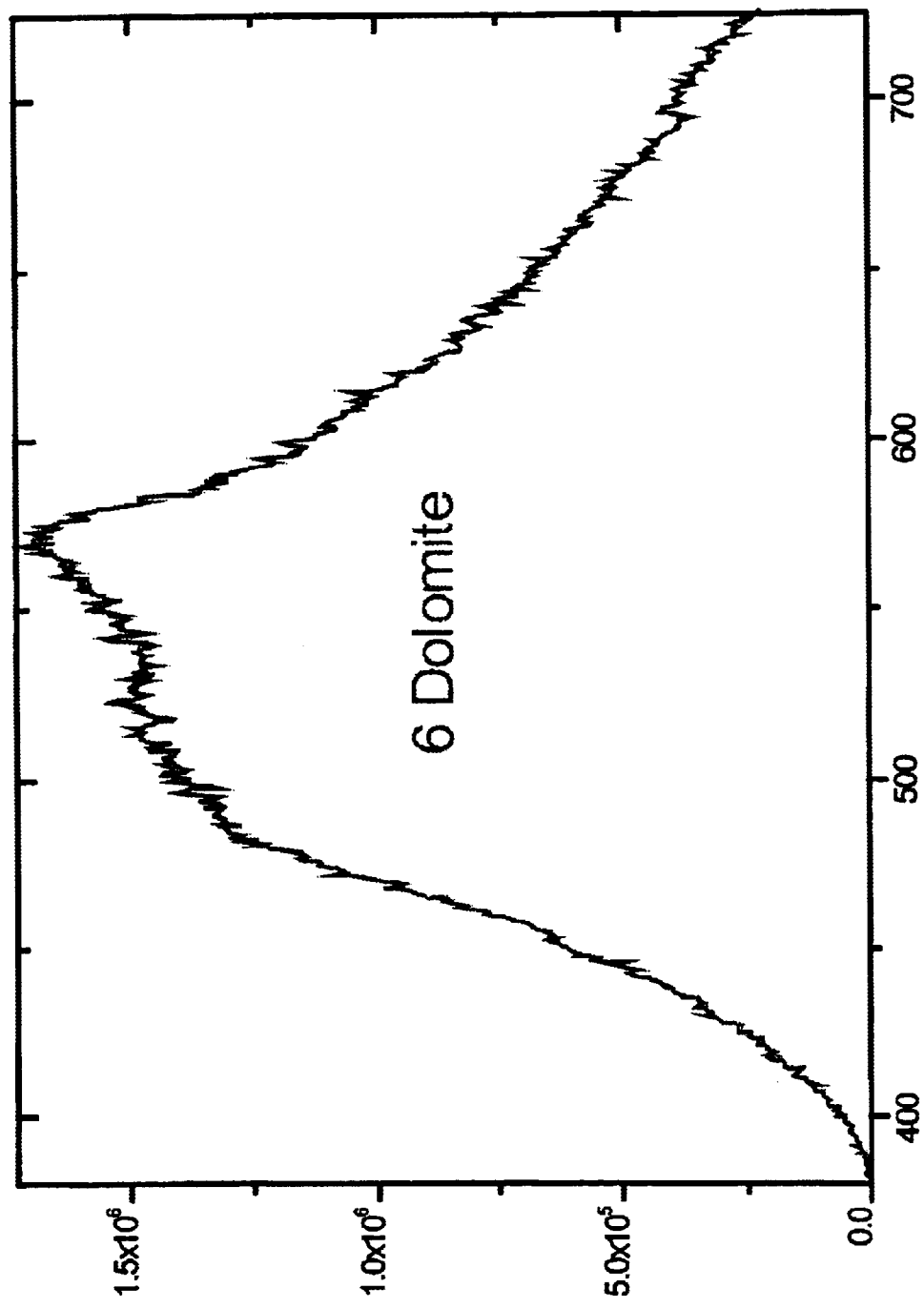
Figure 4K:
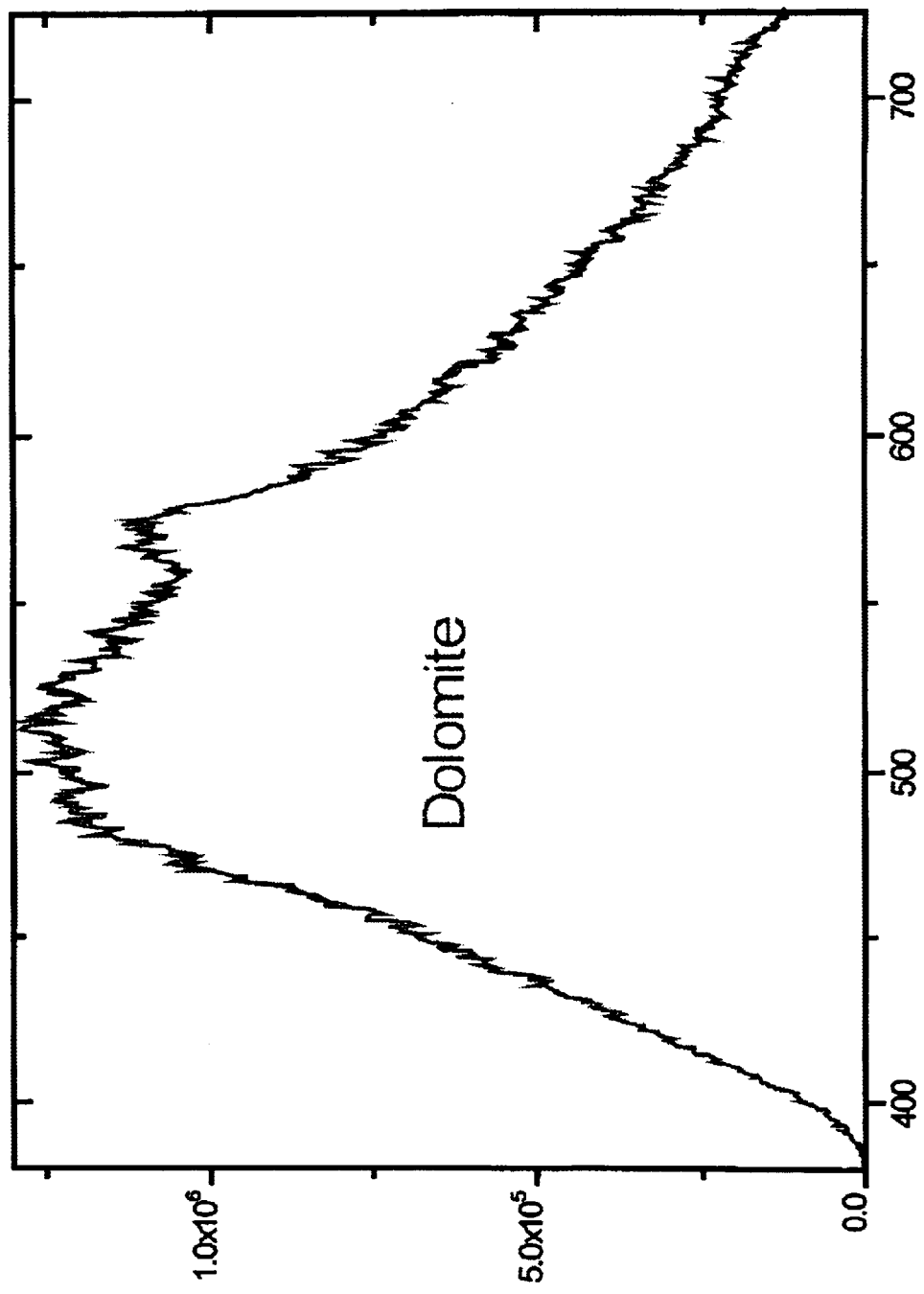
Figure 4L:
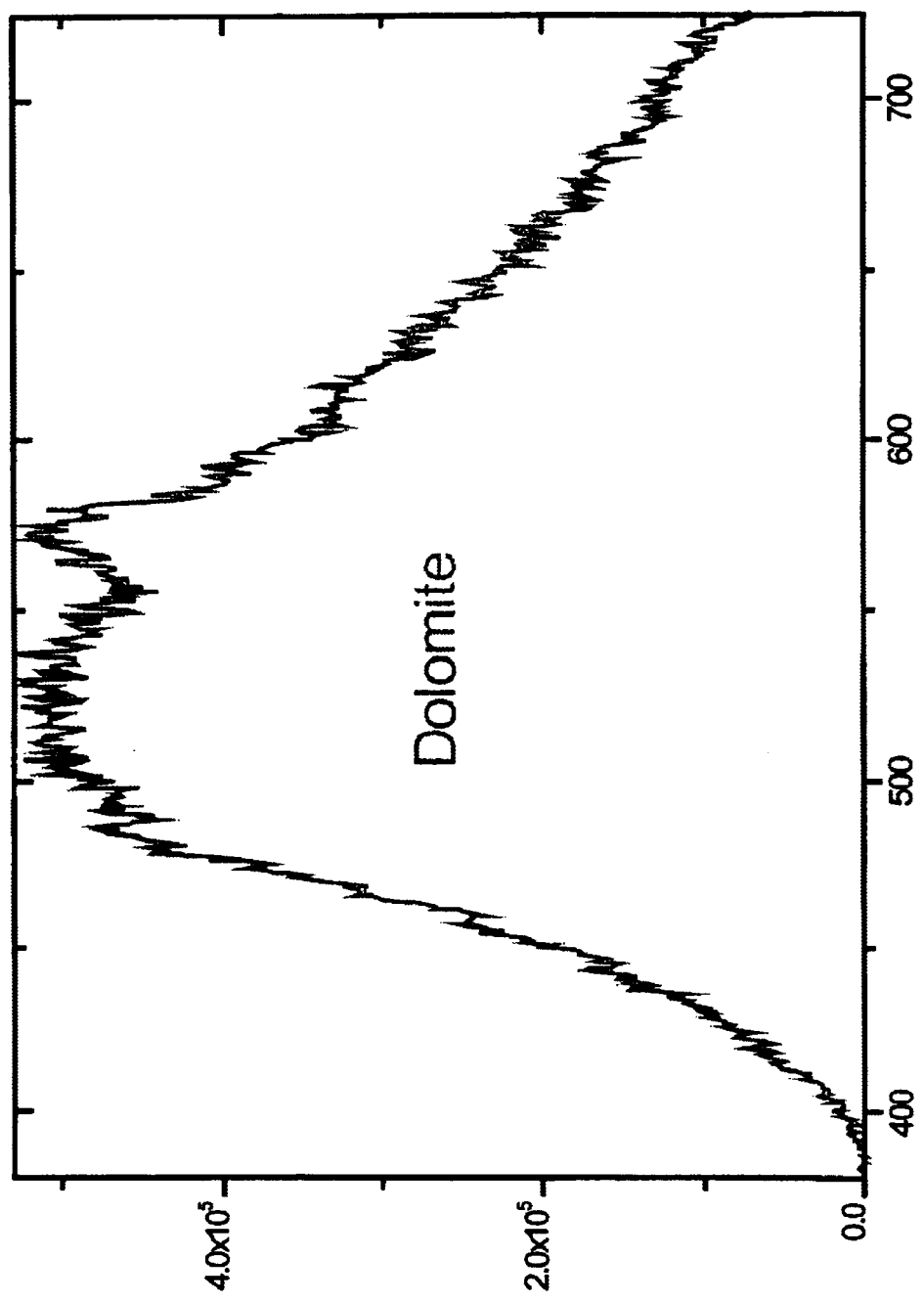
Figure 4M:
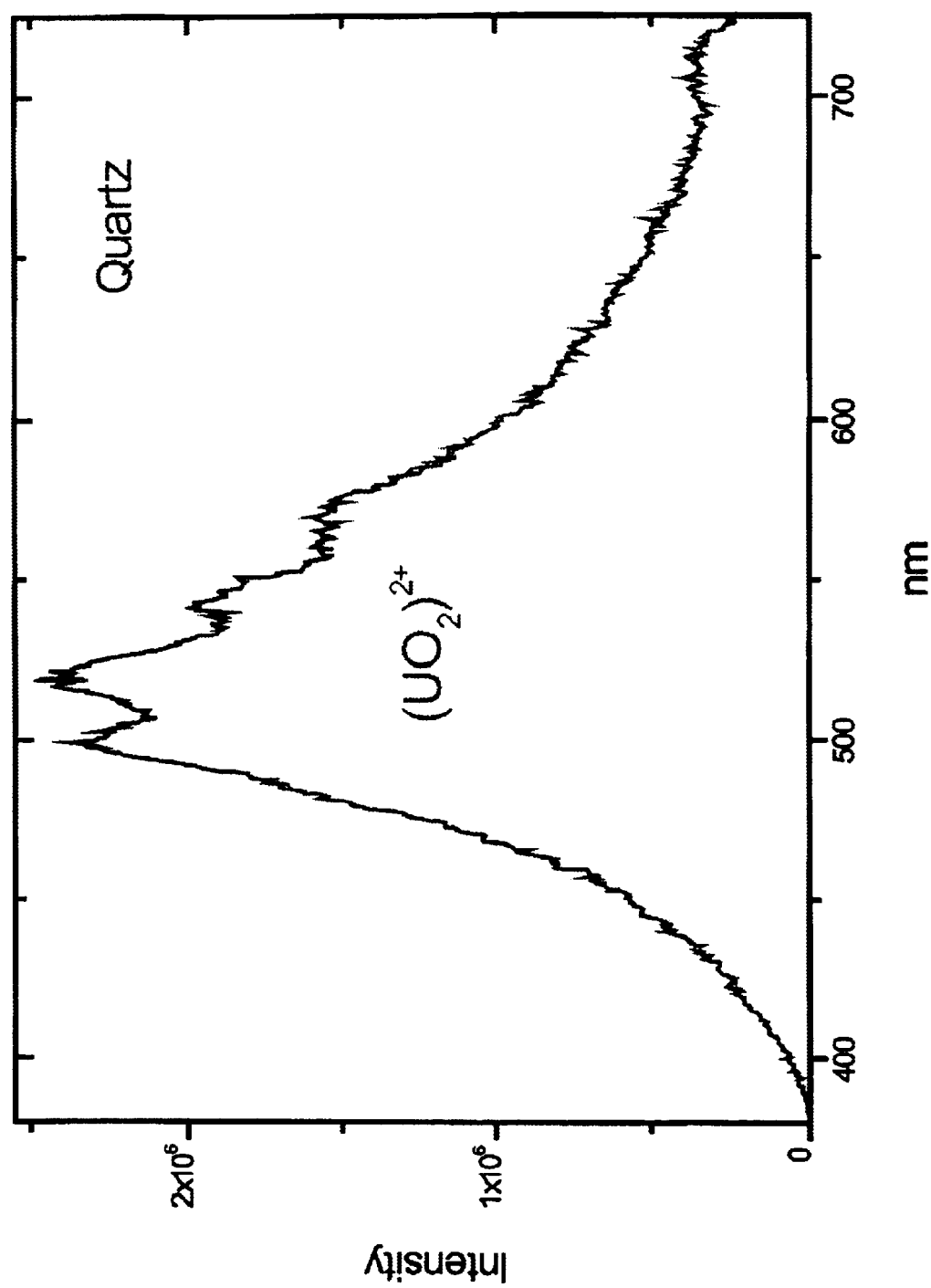
Figure 4N:
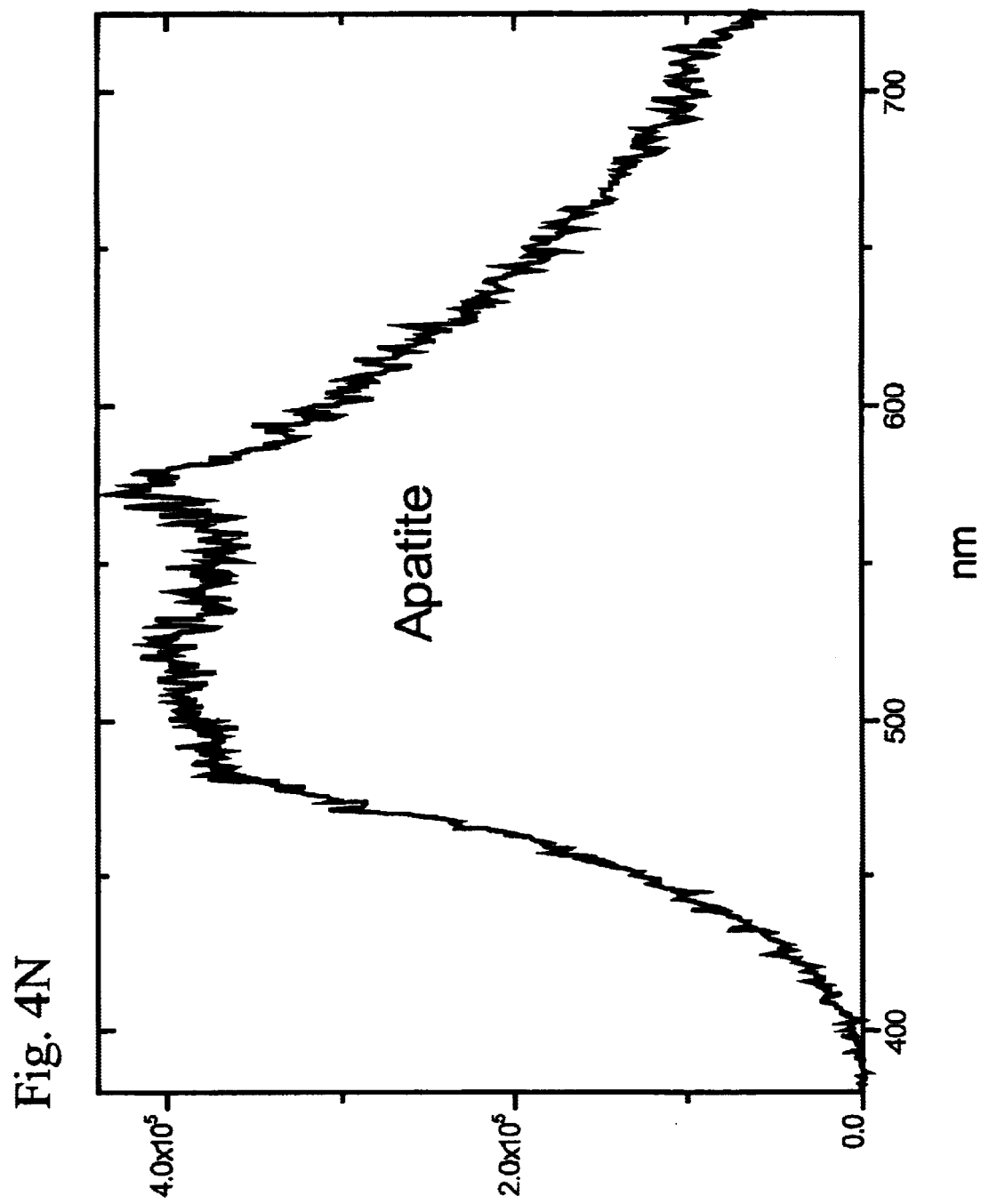
Figure 40:
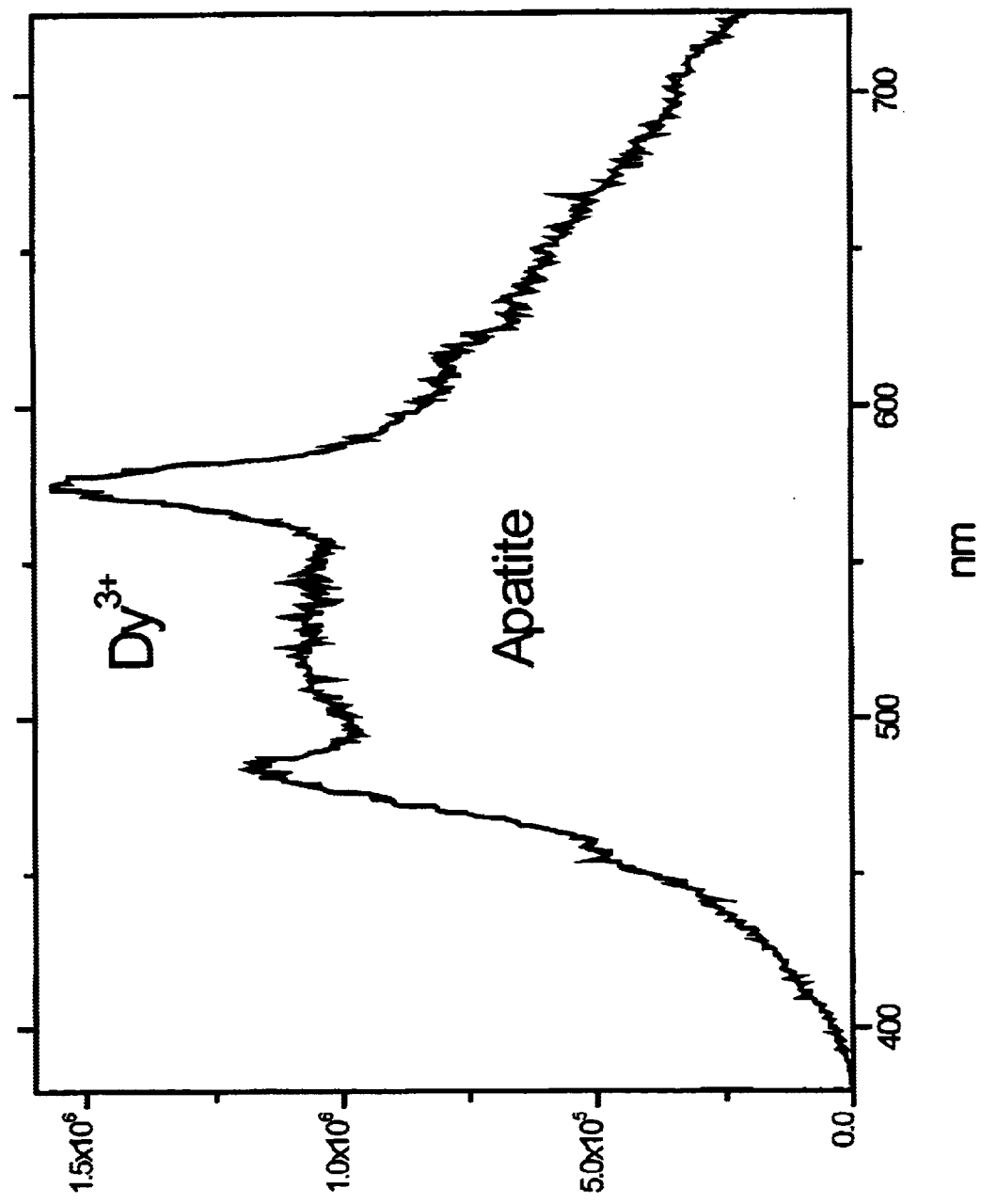
Figure 4P:
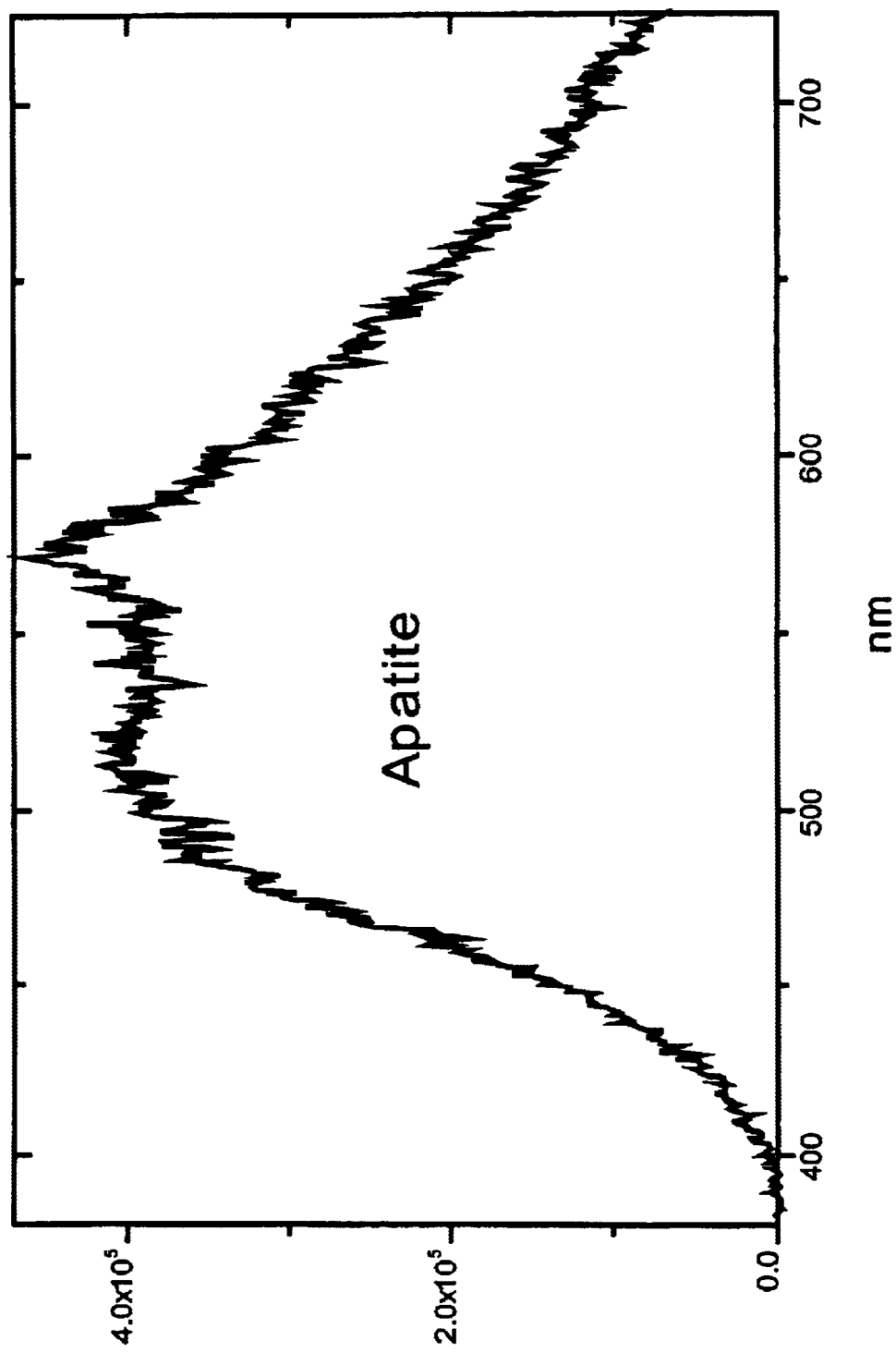
Figure 6A:
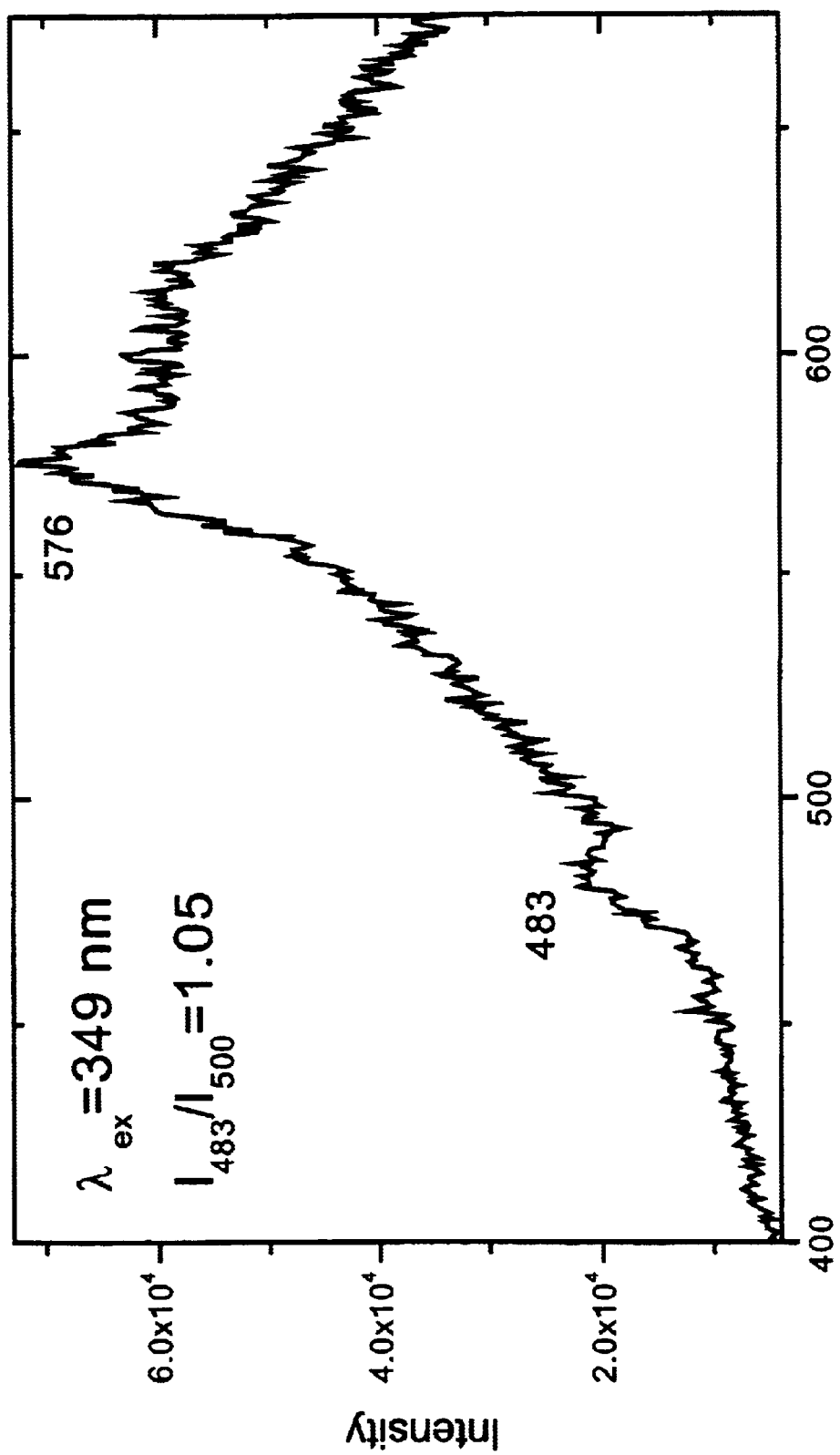
Figure 6C:
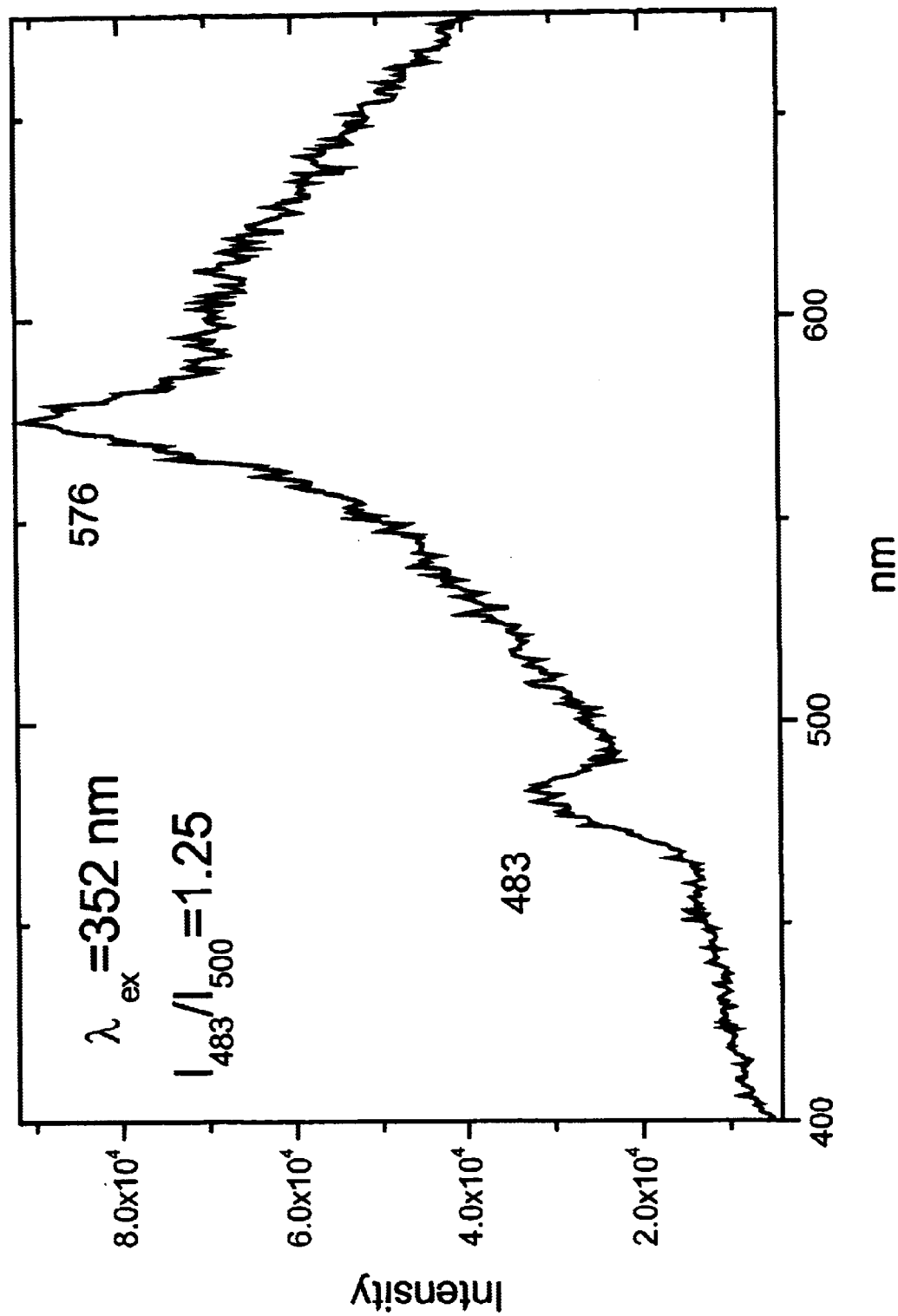
Figure 6D:
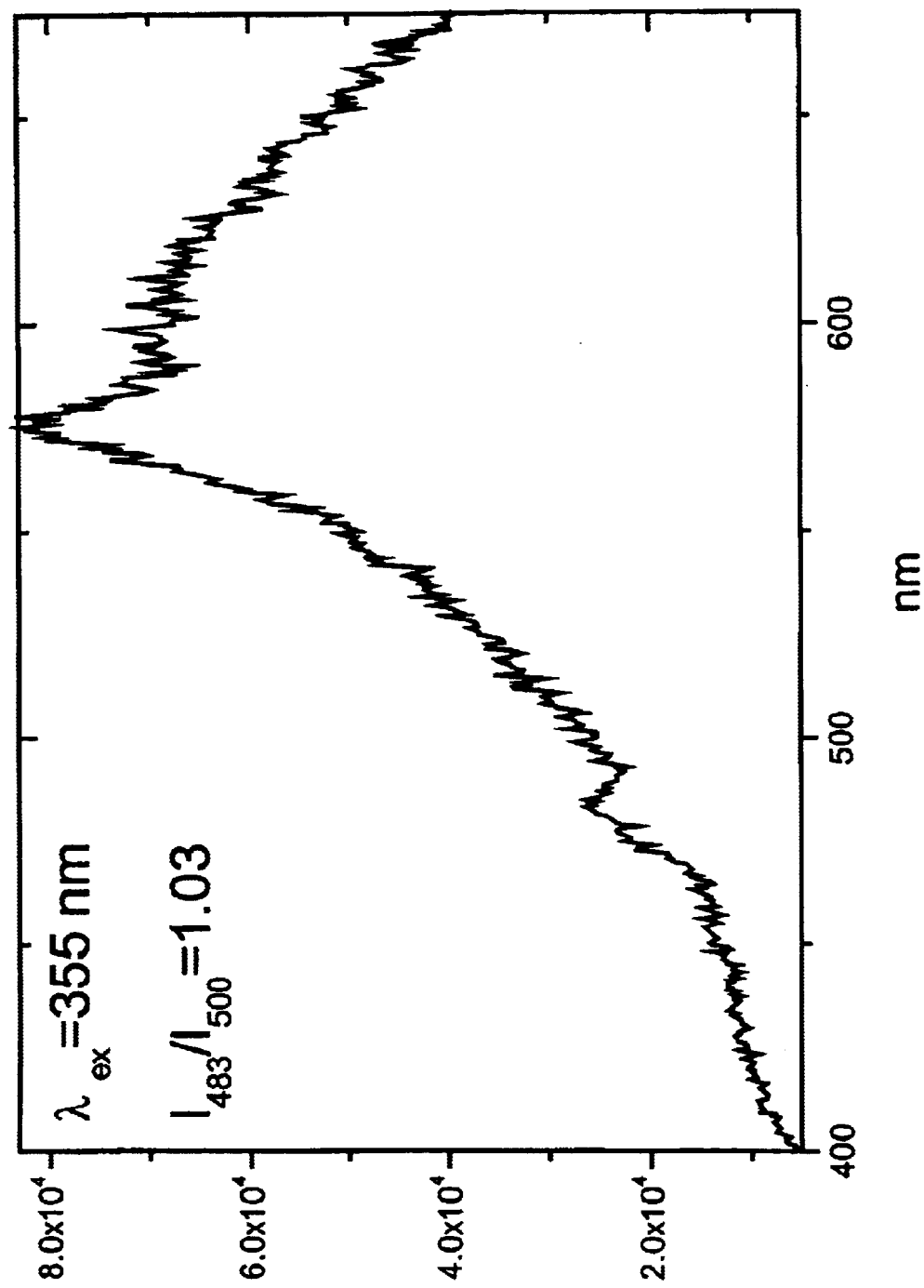

A detailed description of preferred embodiments of the present invention will now be presented with reference to FIGS. 1–13.

The instant invention includes an system and method for the identification of specific species in an ore sample. This is useful for the evaluation of phosphate with high dolomite content, but is not intended to be limited thereto, as the system and method also are applicable to other elements, ions, or compounds occurring in mined mineral ores. The detection of those ions is performed by a source of irradiation, such as a laser energy emitter or other suitable excitation source, and means for delivering to and focusing the irradiation, i.e., the laser energy emission, on a sample on a moving belt, or other conveyor means. The system further comprises a detection system and, in a preferred embodiment, a processor.

Selecting an ionic or elemental species in the desired fraction and performing a screening based upon an intensity ratio $I_{\lambda1}/I_{\lambda2}$, which is characteristic of the emission properties of the ion or elemental species contained in the sample, make positive detection of a desired sample. The detection is accomplished with the use of a LIBS system, or another applicable system commensurate with the parameters of the excitation and emission wavelengths deemed most suitable for the sample.

The laser source range of an illustrative embodiment encompasses, but is not intended to be limited to, ~100–1000 Hz, with pulse energy of no less than 10 mJ. It is contemplated that the laser system may be selected based on subject ion or element, as being known to one of ordinary skill in the art. In addition to laser sources, a suitable excitation source may be employed after the subject wavelengths are determined; this excitation source being chosen based on the ion emission lines and the desired excitation wavelength desired.

Spectral analysis refers to a determination of the intensity of light as a function of wavelength. Any means of spectral analysis known in the art may be used, again, the choice being dependent on the particular application. In a preferred embodiment of the present invention, it was found to be desirable to use a ⅛-mm imaging spectrograph and an intensified thermoelectric-cooled ICCD camera, which is capable of imaging up to 500 spectra/second.

In order to differentiate between wanted and unwanted ore samples, an intensity ratio, $I_{\lambda 1}/I_{\lambda 2}$, threshold is determined, being representative of the composition of the ore contained in the subject deposit. A thorough study of the ores is first made, which includes obtaining a complete spectrum of the minerals from the sample, using the spectral range 200–900 nm with spectral resolution 1 nm. In some instances, it may be necessary to lower the resolution to 0.1 nm in order to resolve spectrally close lines. By using this spectrum rather than any form of database information, it is possible to obtain a spectral fingerprint of the ore and its components, with any interference problems caused by impurities represented by spectral shifts or line-definition problems.

In addition, comparative spectra are then obtained using different power levels and different excitation wavelengths for the laser source. In addition, studies of the decay times of the different lines are made for use with time-resolved spectroscopy. The $I_{\lambda 1}/I_{\lambda 2}$ ratio is then established by selection of two lines characteristic of a "good" sample, which exhibits good definition without interference from other materials.

The presence of a sample fraction in the stream is determined by measurement of its specific emission line intensities. The relative content of selected fraction is determined by the ratio between the numbers of the emission pulses associated with the selected fraction to the total number of emission pulses. This ratio is determined by an investigation of the mineral species contained in the subject ore fractions, both the "good" (wanted) ores and the "bad" (unwanted) ores.

The ratio technique of the present invention is suitable for ore samples having particle sizes from micrometer to large boulder sizes. It is within the scope of the invention to provide a portable version of the system, which provides an effective means of analyzing mine facial or perform in situ examinations within the mining site itself. The system may be applied to moving systems of all varieties known in the art; these including, but not limited to, flow cells, slurry systems, flotation systems, and other moving bed systems known in the art. These also include mechanical movement as well as chemical movement means. Because the ratio of the emission lines is determined for the subject ores from a specific location, the presence of organic impurities, water, other flocculents, and slurry agents or impurities does not affect the results, since the ratio is made from emission lines selected for their spectral purity. Indeed, any line that exhibits such interference is not of interest for establishment of the intensity ratios of the present invention.

In a further embodiment, the spectral analysis data can be output to a computer with a display monitor, combined with an electronic card or having an algorithm that enables the laser beam to synchronize with the ICCD, to measure two emission signals from two different pixels simultaneously, to calculate their ratio, to identify accept or reject fractions according to the ratio, to demonstrate the place of corresponding mineral on the computer screen, and then calculate the subject fraction content of desired or undesired ions or elements.

With respect to phosphate rocks, the intensity ratio of the characteristic emission lines of Mg at 518 nm and F at 604 nm enables a detection of pebbles having high dolomite content. Because dolomite $(Ca, Mg)(CO_3)_2$ contains Mg and not F, and phosphate $Ca_5(PO_4)_3(F,O):Ca_5(PO_4)_3CO_3$ contains F but only minimal Mg, $I_{518}/I_{604}$ enables that both phases be consistently identifiable within the time available for examination by LIBS.

The analytical line of Mg at 518 nm is characterized by a decay time of approximately 200 ns. This makes for an optimal time-resolution spectrum with a narrow gate of 1 μs. Under such conditions the intensity of the relatively broad band in the range 600–630 nm connected with carbonate is substantially lower, and the ratio $I_{518}/I_{606}$ is higher. The decay time of the F characteristic line at 606 nm of approximately 500 ns is longer than that for Mg, but it is still relatively strong with gate of 1 μs, and apatite is easily detected. Damp samples of apatite and dolomite from a moving belt have been checked, and essentially the same spectra are detected. Thus a delay time is not needed, and time-resolved spectroscopy with zero delay and a gate width of 1 ms may be accomplished using intensified thermoelectric-cooled ICCD cameras.

The system and method of the present invention are further characterized by the following example.

Example 1 Use of LIBS to Differentiate Florida Phosphate Ores

Natural apatite contains several characteristic luminescence centers that enable differentiation from dolomites (FIG. 1A). The most widespread characteristic luminescence center is uranyl $(UO_2)^{2+}$, with typical vibrational green-band luminescence under nitrogen laser excitation as shown in FIG. 1B. Under close inspection of Florida phosphate rock, this moiety was absent; FIGS. 2A–2D show the spectra derived by laser-induced luminescence of the apatite (FIGS. 2C,2D) and dolomite (FIGS. 2A,2B) from Florida mines.

In order to find a distinguishing or "fingerprint" characteristic ion for identifying dolomite and apatite, ICP-MS analysis of Florida phosphates was performed. It was found that apatite contained rare earth elements, and in the case of the Florida apatites, these were present in quantities suitable for laser-induced luminescence analysis. As seen in Table 1, the highest concentration and quantum efficiency is for $Ce^{3+}$, but this ion has a luminescence in the UV-violet portion of the spectrum and also has a very short decay time, comparable with times for organic material. Thus its luminescence would not be clearly seen if the sample contained a great deal of background organic matter. From the other rare-earth ions detected, $Dy^{3+}$ was the best candidate owing to its favorable combination of concentration, quantum efficiency, and spectral and temporal characteristics. According to the $Dy^{3+}$ excitation spectrum, the third harmonic of a Nd-YAG laser at 355 nm was deemed the most suitable among the lasers commonly available at present. Narrow lines of $Dy^{3+}$ with long decay times of 500–600 ms appear under 355-nm excitation in apatites, but they have never been detected in dolomite (see FIGS. 3A–3D), since dolomite comprises a very poor matrix for luminescence center formation, and because of the isomorphous substitution of $Ca^{2+}$ in apatite being much easier for the trivalent rare-earth elements than the divalent $Mg^{2+}$ found in dolomite. Thus the fingerprinting ion was determined for the present embodiment.

To further investigate the efficacy of the $Dy^{3+}$ for positive differentiation of apatite from dolomite, more than 200 samples were randomly chosen from ore. Two selective features were chosen to study: characteristic lines of $Dy^{3+}$ and intensity ratios at 580 and 530 nm ($I_{580}/I_{530}$). Typical spectra obtained under 355-nm excitation are presented in FIGS. 4A–4P.

The >200 samples were classified and identified as follows: Fraction +½ in. Twenty-two samples having sizes greater than ½ in. were randomly chosen from the light-colored part of the ore: 9 were identified by X-ray diffraction as apatite and 13 as dolomite. By laser-induced time-resolved luminescence (LITRL), 6 apatites clearly demonstrated $Dy^{3+}$ while this ion was never detected in dolomite. The parameters using $I_{580}/I_{550}$ are substantially the same.

Thirteen samples were randomly chosen from the dark-colored part, and all were identified by X-ray diffraction (XRD) as apatite. $Dy^{3+}$ appears only in 45%, while the intensity-ratio feature was not possible to check due to a lack of dark dolomite for comparison.

Fraction +⅜ in.

Twenty-nine samples having sizes greater than ⅜ in. were randomly chosen from the light-colored part: 15 were identified by XRD as apatite and 14 as dolomite. By LITRL, 6 apatites clearly demonstrated $Dy^{3+}$, while none was again detected in the dolomite. The intensity-ratio distinguishing feature enabled 12 apatite pebbles to be identified (80%), but one dolomite (7%) was also determined to be apatite.

Twelve samples were randomly chosen from the dark-colored part: 10 were identified by XRD as apatite and 2 as dolomite. $Dy^{3+}$ appeared only in 2 samples (20%), while the intensity-ratio distinguishing feature enabled identification of 8 apatite pebbles (80%) with complete rejection of dolomite.

Fraction +0.156 in.

Sixteen samples having sizes greater than 0.156 in. were randomly chosen from the light-colored part: 10 were identified by XRD as apatite and 6 as dolomite. By LITRL, 8 apatites (80%) clearly demonstrate $Dy^{3+}$, while again none was detected in the dolomite.

Twelve samples were randomly chosen from the dark-colored part: 11 were identified by XRD as apatite and 1 as dolomite. $Dy^{3+}$ appears in 9 samples (82%).

Fraction +16

Thirty-one samples having sizes greater than 16 mesh (approx. 1 mm) were randomly chosen from the light-colored part: 25 were identified by XRD as apatite and 6 as dolomite. By LITRL, 20 apatites (80%) clearly demonstrated $Dy^{3+}$, while again none was detected in the dolomite.

Twelve samples were randomly chosen for the dark-colored part, and all were identified by XRD as apatite. $Dy^{3+}$ appeared in 9 samples (75%), but no dark dolomite was available for comparison in this fraction.

Kingsford Sample

Twenty-three were randomly chosen from the light-colored part: 16 were identified by XRD as apatite and 7 as dolomite. By LITRL, 9 apatites (56%) clearly demonstrated $Dy^{3+}$, while again none was detected in the dolomite. The intensity-ratio distinctive feature enabled the identification of 13 apatite pebbles (81%).

Twelve samples were randomly chosen from the dark-colored part, and all were identified by XRD as apatite. $Dy^{3+}$ appeared in 9 samples (75%), with no available dark dolomite available for the ratio comparison.

Fort Green Sample

Eighteen samples were randomly chosen for the light-colored part: 15 were identified by XRD as apatite and 3 as dolomite. By LITRL 11 apatites (73%) clearly demonstrated the presence of $Dy^{3+}$, while again none was detected in the dolomite.

Twelve samples were randomly chosen from the dark-colored part: 11 were identified by XRD as apatite and 1 as dolomite. $Dy^{3+}$ appeared in 9 samples (82%).

The results of these studies are tabulated in Table 2, the data of which indicate that the main object is the light-colored fraction, where the average dolomite content was 33%, while that in the +½ fraction was nearly 60% and in the +⅜ fraction, more than 50%. The dark-colored fractions usually contained 1% dolomite.

In order to address the problem that Dy3+ luminescence intensity varies strongly from apatite to apatite, an optimal excitation band was chosen. It is well known that Dy3+ has very narrow excitation bands, this being confirmed by the fact that in the apatite it is strongly excited by 355-nm radiation, but absolutely not at 337 nm.

FIGS. 5A–5D are luminescence spectra under different excitations of $Dy^{3+}$ for a sample of sedimentary apatite from Florida with relatively strong lines of $Dy^{3+}$. The most important parameter for apatite and dolomite differentiation is the ratio of luminescence intensities at 482 and 500 nm ($I_{482}/I_{500}$). The best result was achieved for excitation under 351 nm, which was 1.2 times stronger than for excitation under 355 nm. FIGS. 6A–6D present the same data for Florida sedimentary apatite with weak $Dy^{3+}$ luminescence lines. Because under 355-nm excitation the $I_{482}/I_{500}$ ratio is very close to 1, it could be mistaken for dolomite, but under 351-nm excitation this ratio is 1.2 times stronger, and the identification is then correct. In addition, 351 nm exactly corresponds to the emission wavelength of excimer XeF lasers. Using a state-of-the-art laser, which has repetition rates up to 500 Hz with maximum energy of 20 mJ per pulse, further study of these energy parameters showed that Florida apatite having strong $Dy^{3+}$ luminescence was detected with a pulse energy of 5 mJ or less. In the case of weak $Dy^{3+}$ luminescence, the lowest level was determined to be 8–10 mJ.

In an additional embodiment, the sensitivity was improved by computerized spectral analysis using smoothing, which achieves an improvement of the signal-to-noise ratio by mathematical processing of the raw data. A widely used method of spectral data smoothing in the art is the moving window and polynomial curve fitting (the Savitzky-Golay method). This method also includes simultaneous processing of the data to locate peaks by the calculation of the spectrum derivatives. The moving window scans spanning M data points, moves along the data, and creates an estimation of smoothing spectrum or its derivative in the inner window point.

In order to computerize the analysis of spectral data, a software program was written containing the following elements:

1. Reading of the ASCII files
2. Smoothing by the Savitzky-Golay method (SGM)
3. Calculation of the first and second derivatives of spectrum data by SGM
4. Calculation of background by the least-squares method
5. Peak searching
6. Calculation of the peak amplitude above the background
7. Storing the results in Microsoft Excel files The significant difference between apatite and dolomite is the presence of a peak near 483 nm in the apatite spectrum that is not present in the dolomite spectrum.

The purpose of the first step of the analysis is smoothing of spectra and checking for a peak in the 483-nm area. A 5-point SGM has been used for smoothing, which gives effective results for increasing the signal-to-noise ratio. It was determined that all apatite spectra have peaks in the 483-nm region (the average wavelength of the peak maximum is 483.250 nm, with a standard deviation of 1.572 nm). At that time only 7 of the dolomite spectra demonstrated a peak in this area (average wavelength 483.219 nm, standard deviation 2.144 nm).

Background calculation was made by the least-squares method. The parabolic approximation of the background gave satisfactory results, and the peak amplitude over the background was calculated for all spectra. This analysis showed that peak amplitude above the background for the apatite spectra is much higher than for the dolomite spectra. For apatites, the average value is 9.74%, with a standard deviation of 6%, while for dolomites the average value is 0.91%, with a standard deviation of 2.21%.

The system 10 of the instant invention is illustrated schematically in FIG. 7. This system 10 comprises a computer such as a PC 30 in circuit communication with a laser source 20, here a Nd:YAG laser. As described previously, other suitable lasers or non-laser excitation sources may be used, depending on the material to be analyzed and on the wavelengths sought for optimal resolution. The beam emitted from the laser 20 passes through harmonic crystals 21 and a filter 22 before passing through lens 25 and then impinging on the sample 23. The crystals 21, filter 22, and lens 25 serve to attenuate the laser beam, and thus the excitation energy passed onto the sample 23 is optimized. A suitable detection apparatus such as a CCD time-gated system may be used or a detection system based on photomultipliers may also substituted. Such a system is shown in FIG. 7 and comprises a semitransparent mirror 26 and interference filters 24 connected to photomultiplier tubes 26, powered by power suppliers 27. The signals generated by the photomultiplier tubes 26 are then transmitted gating and integrating electronics 28, which then sends the signal back to the PC 30.

Figure 8:
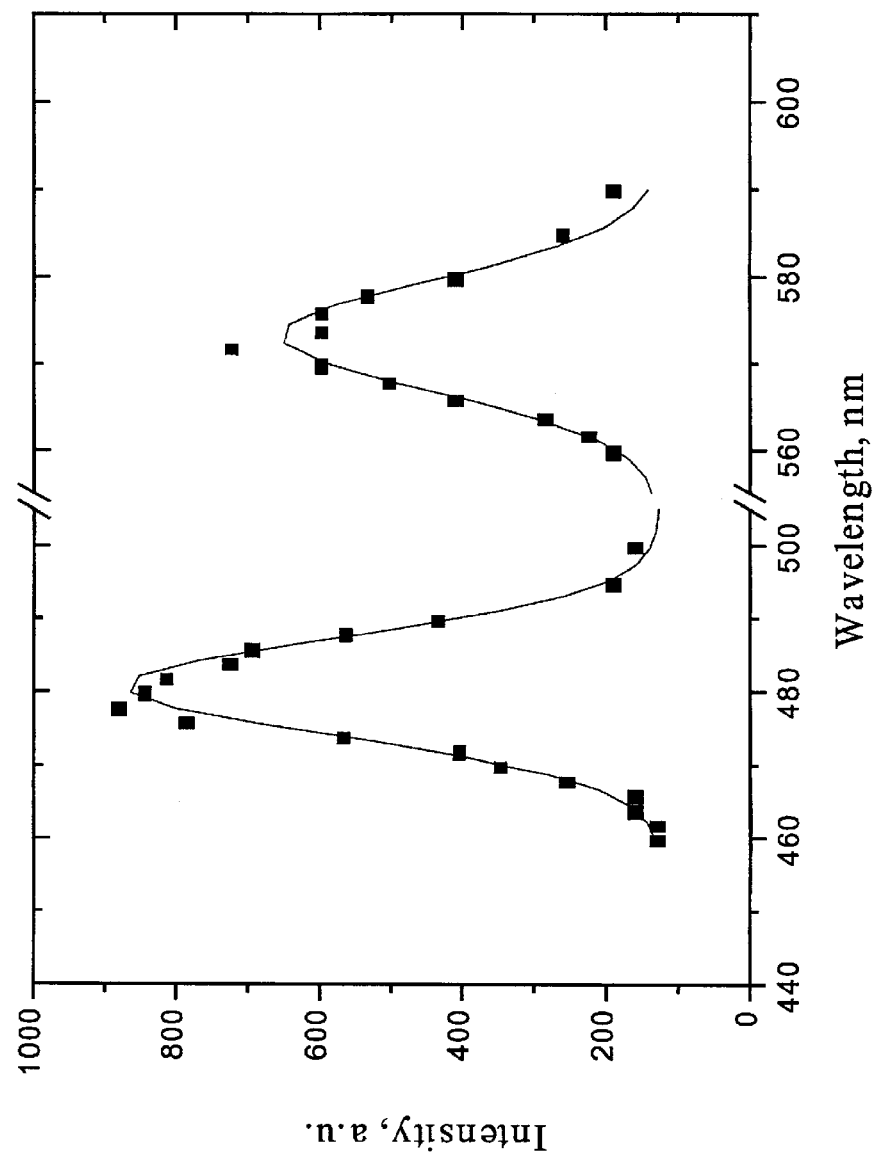
FIG. 8 is a $Dy^{3+}$ intensity spectrum.

In a further study of Florida apatite and dolomite, a light pulse of the 3 d harmonic of a Nd:YAG laser (355 nm, 30 ns) was used for luminescence excitation. The luminescent light after passing through the monochromator assembly comprising the crystals 21, filter 22, and lens 25 after contacting the sample 23 was transmitted to photomultiplier tubes (PMT) 26 via interference filters 24. The registered pulses were then transmitted to a memory oscilloscope, depicted as the gating and integrating device 28. Luminescence pulses at 480 nm consist of two elements: an intense fast element and a much weaker slow component, the fast component being approximately three orders higher in magnitude than the slow component. The decay time of the fast component is about 30 ns, and that of the slow component about 800 $\mu$s. At 500 nm only a fast luminescence component was detected, as shown in FIG. 8. The spectrum was recorded using an oscilloscope, and the amplitude of the signal was measured at a time delay of 500 ms. The spectrum and decay time of the slow component confirmed that this was due to the presence of the $Dy^{3+}$ in the sample, identifying it as apatite. The luminescence spectrum of the fast component was approximately the same for apatite and for dolomite, this being attributed to adsorbed water and organic matter.

Further modifications of the apparatus 10 are also intended to be within the scope of the present invention. In the embodiment above, apatite sorting was based on comparative time-delayed measurement of the luminescence intensity at certain spectral points, namely 480 and 520 nm. In this embodiment, in order to detect the $Dy^{3+}$ signal, which was very weak with respect to the background signal, a longer decay time was used, this being effected by the photomultiplier tubes" being started with a time delay. The PMT output delay was electronically regulated by the electronics 28, with both delay time and gate width being regulated. This enabled the weaker $Dy^{3+}$ lines to be read as if they were strong; thus the time delay overcame the lack of intensity, and differentiation between dolomite and apatite was successfully accomplished.

To overcome another problem caused by the time-delay system, another approach to the gating aspect was employed. Owing to the large resistance of the output PMT, the "tail" from the fast non-characteristic luminescence component still hid the weaker $Dy^{3+}$ luminescence, with a resulting sensitivity reduction. As an alternative approach, two PMT gated systems (Electron Tubes Ltd.) were used. The gating was based on switching out the PMT high voltage at a PMT cathode for time needed for delay (i.e., the gating time). The PMT housing, filter holder, and double PMT power supplier were also modified; these included coupled fiber connectors that enabled fibers to be used for simultaneously detecting two luminescence intensities at the two different wavelengths, 480 and 520 nm. The above substitutions and modifications are considered within the scope of ordinary skill in the art.

Figure 9A:
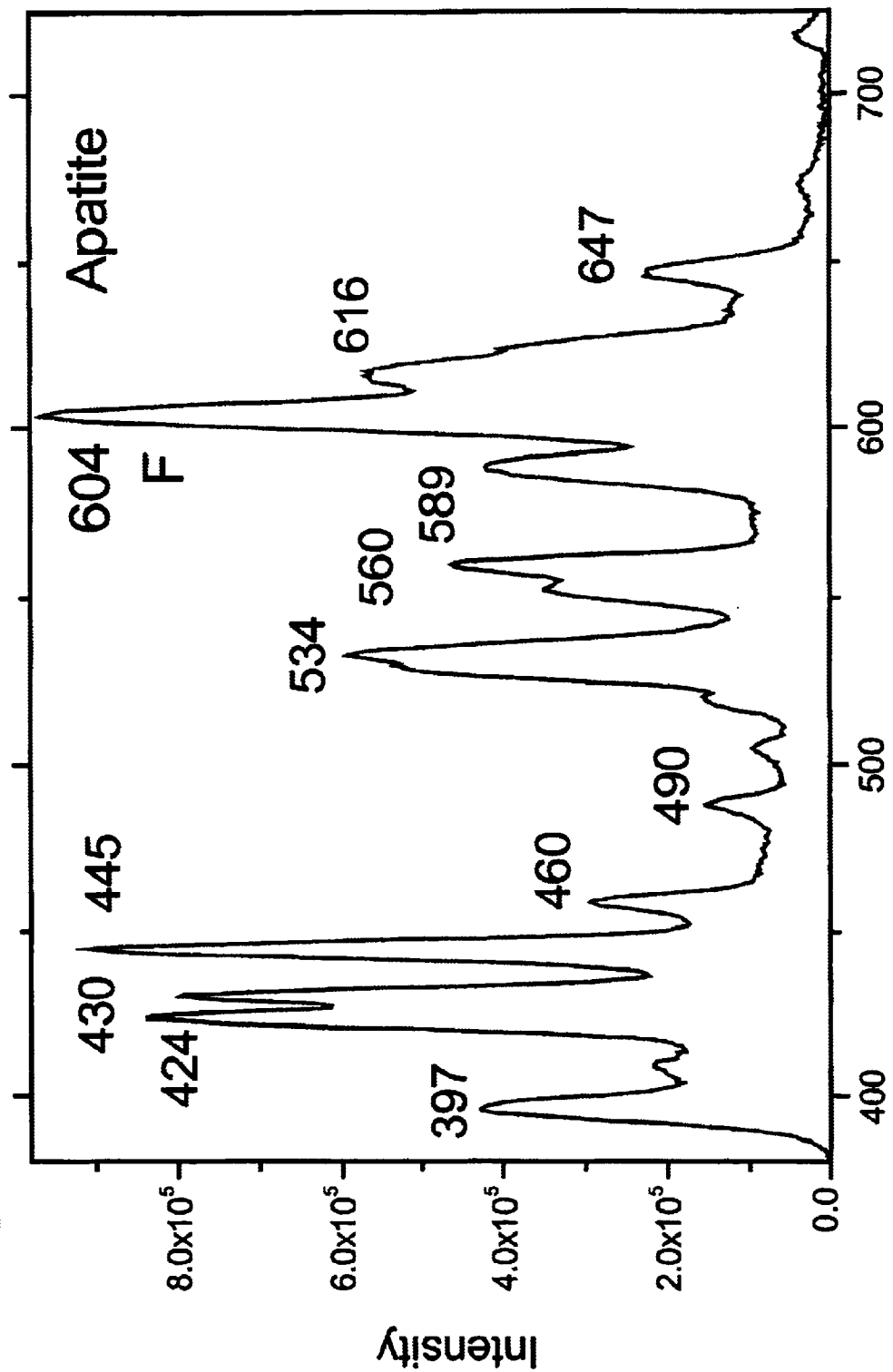
FIGS. 9A–9D are LIBS spectra for various minerals found in ores (FIG. 9A, apatite.
Figure 9B:
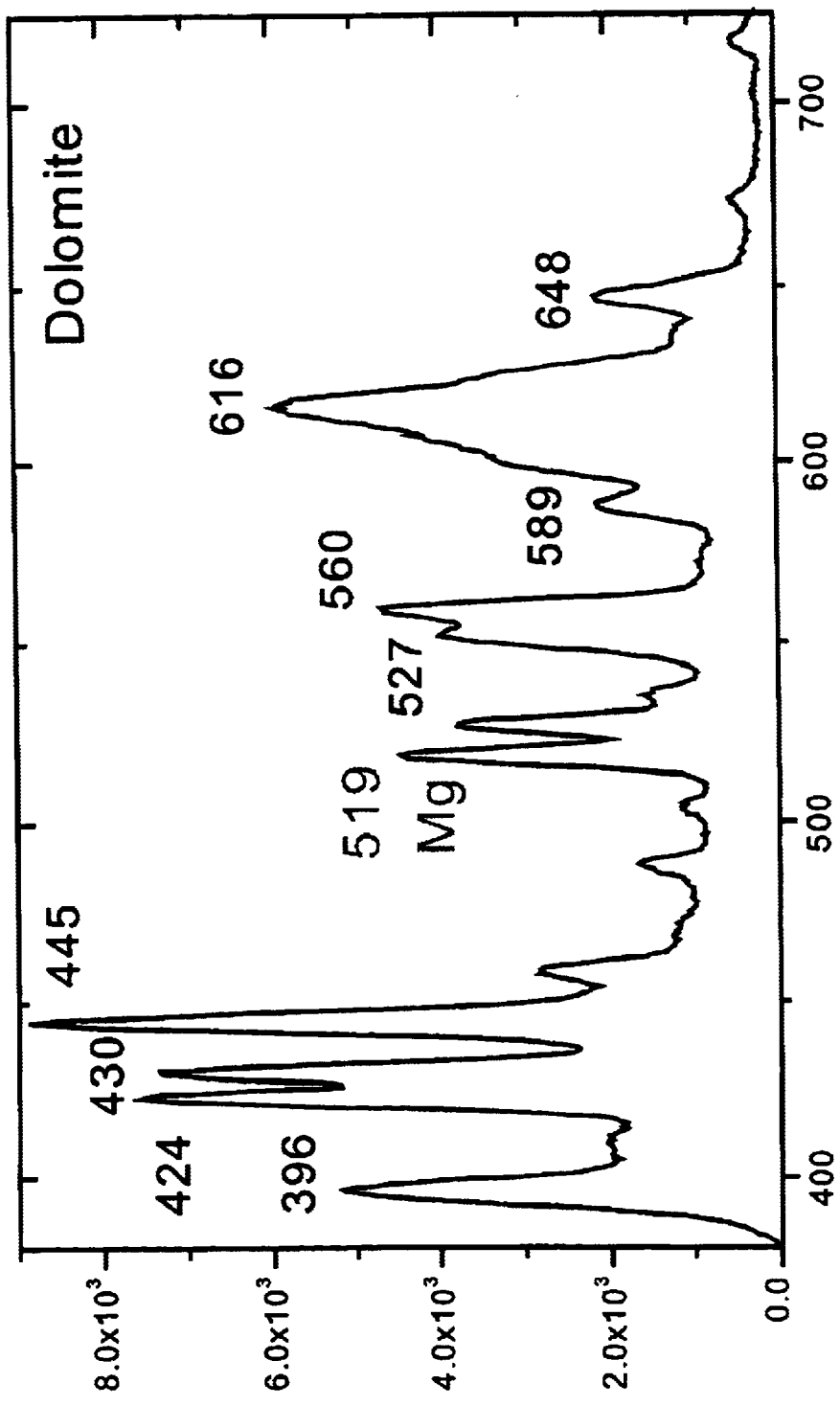
Figure 9C:
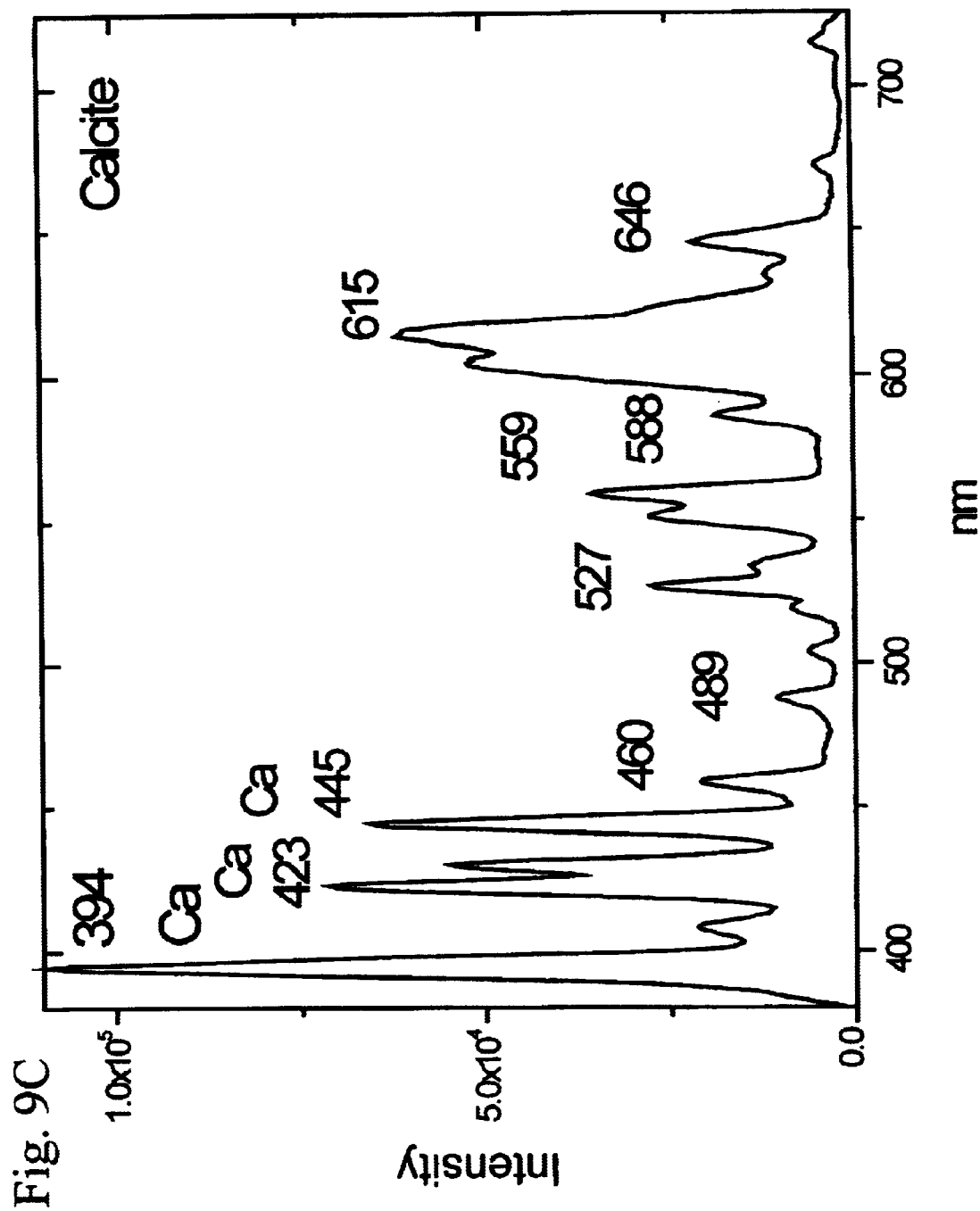
Figure 9D:
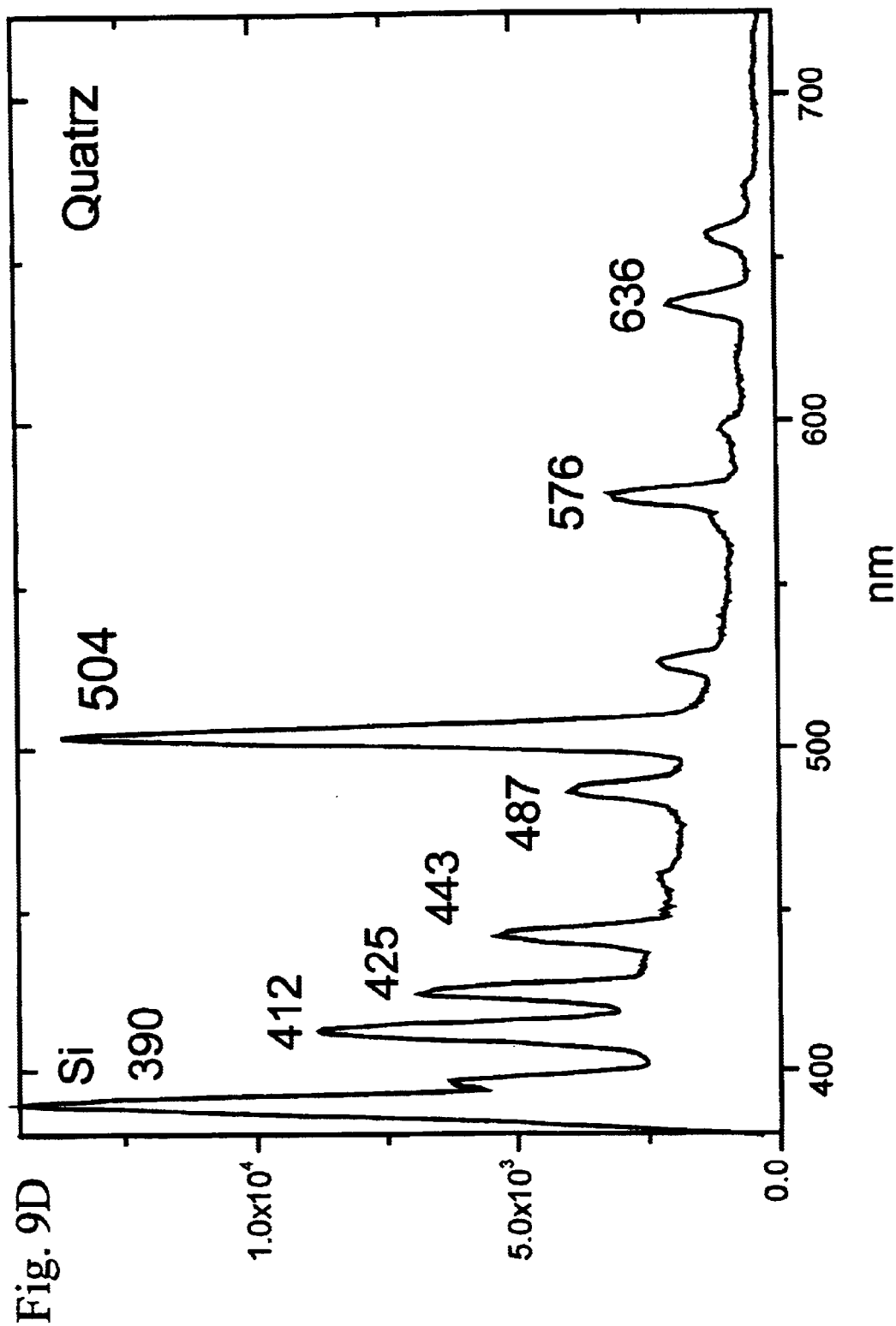
Figure 11A:
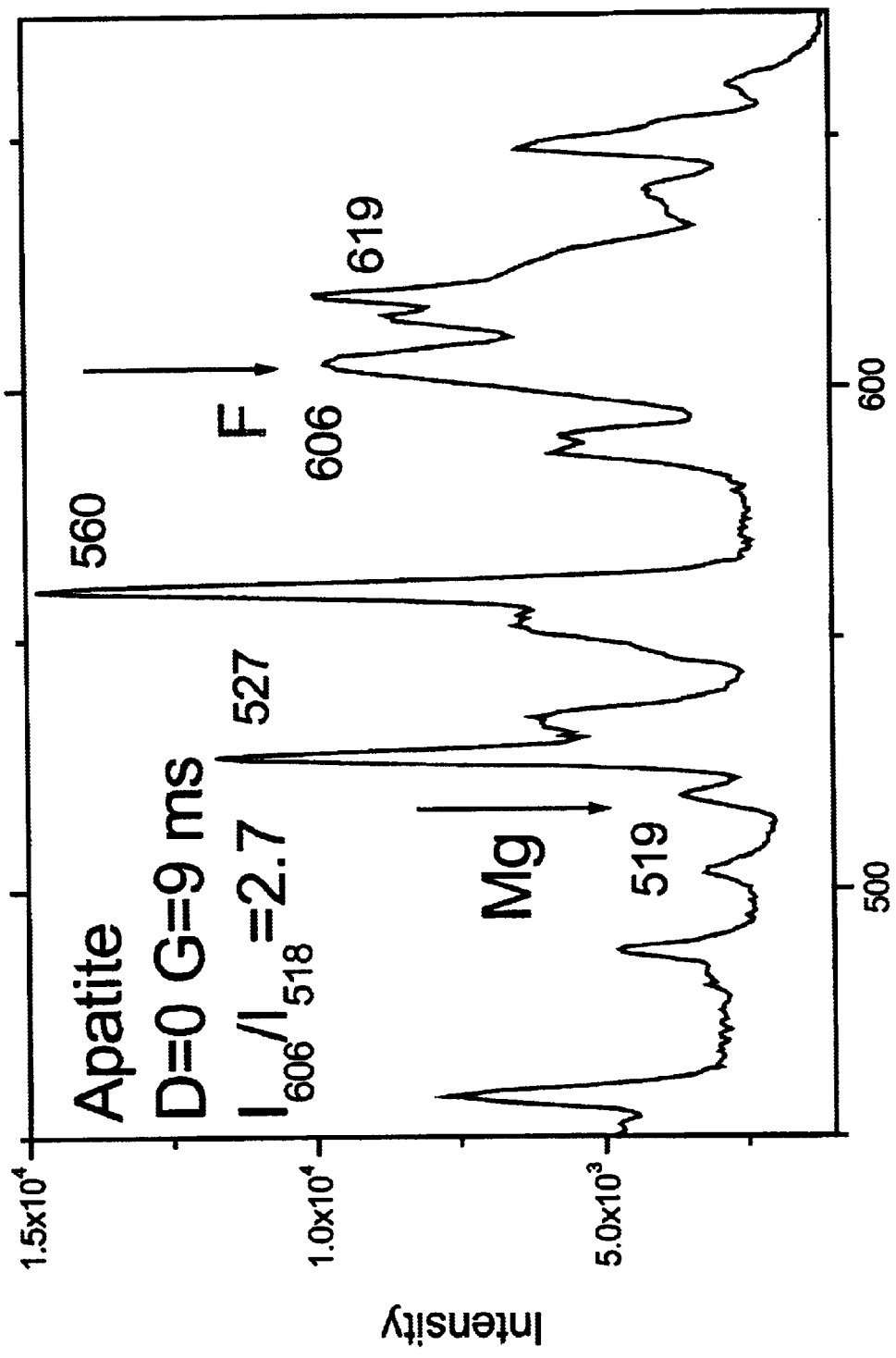
FIGS. 11A–11D are time-resolved LIBS spectra of Florida apatite (FIG. 11A, delay=0, gate=9 ms, $I_{606}//_{518}$=2.7.
Figure 11B:
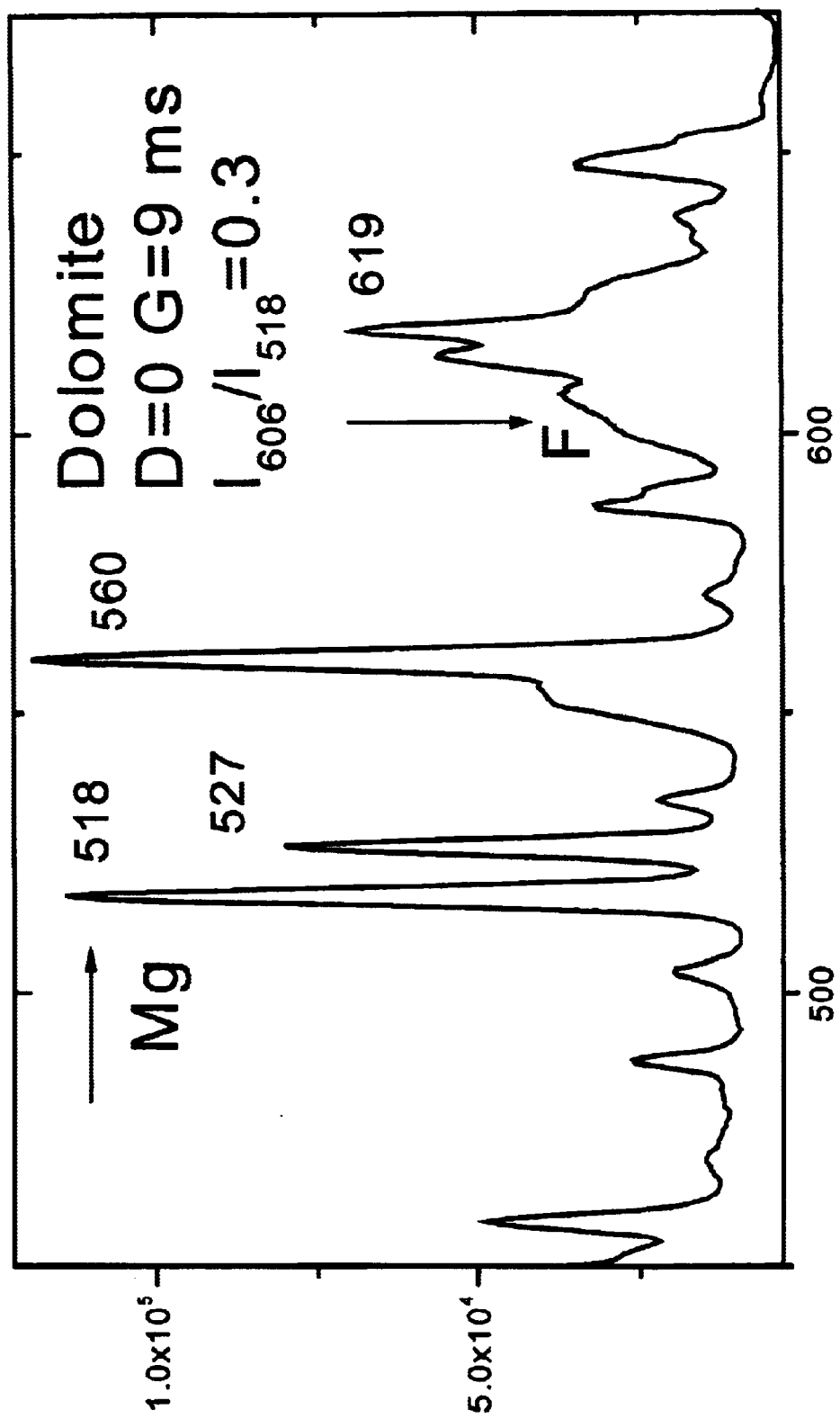
Figure 11C:
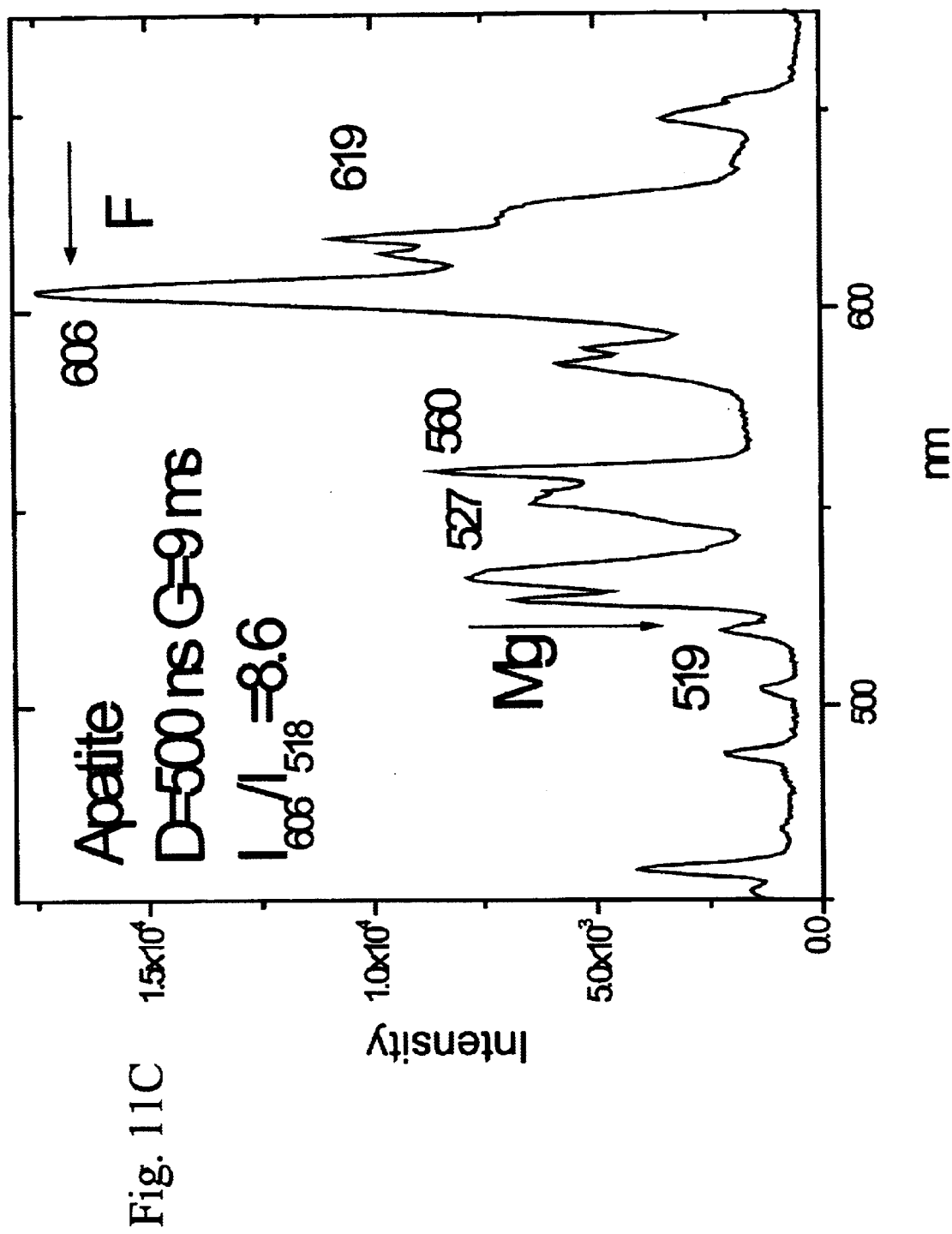
Figure 11D:
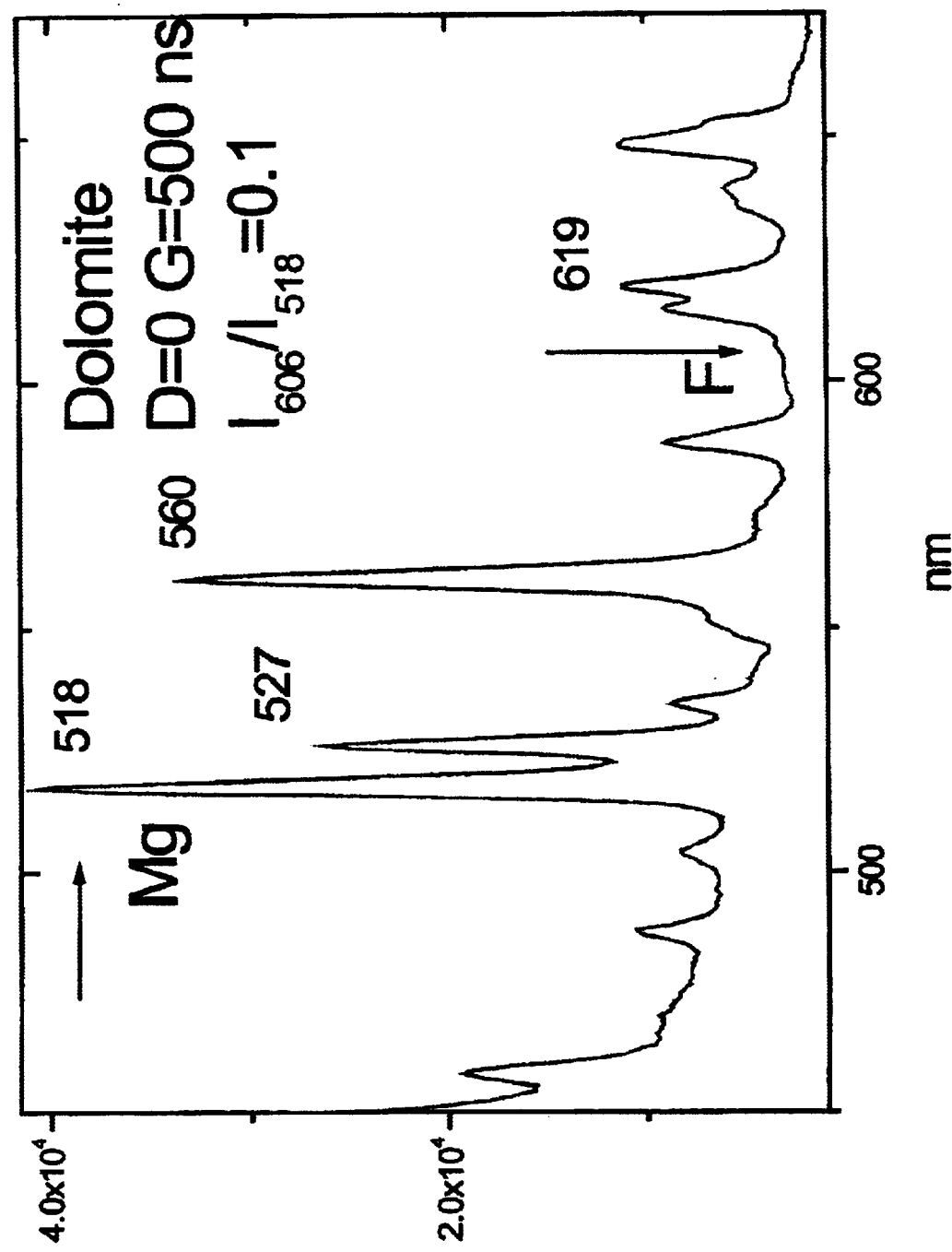
Figure 12A:
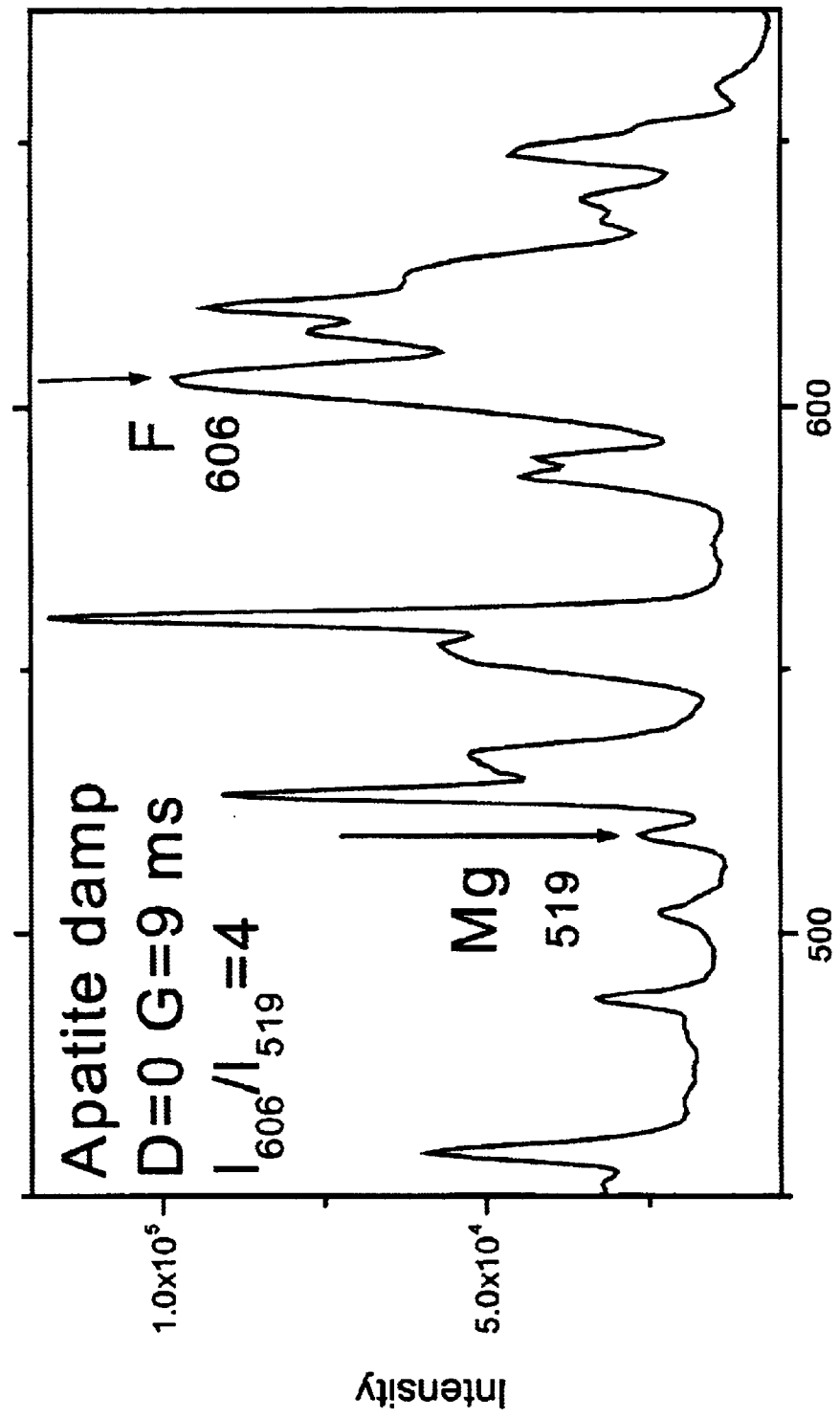
FIGS. 12A–12D are spectra of time-resolved LIBS for wet apatite (FIG. 12A, delay=0, gate=9 ms, $I_{606}//_{519}$=4.
Figure 12B:
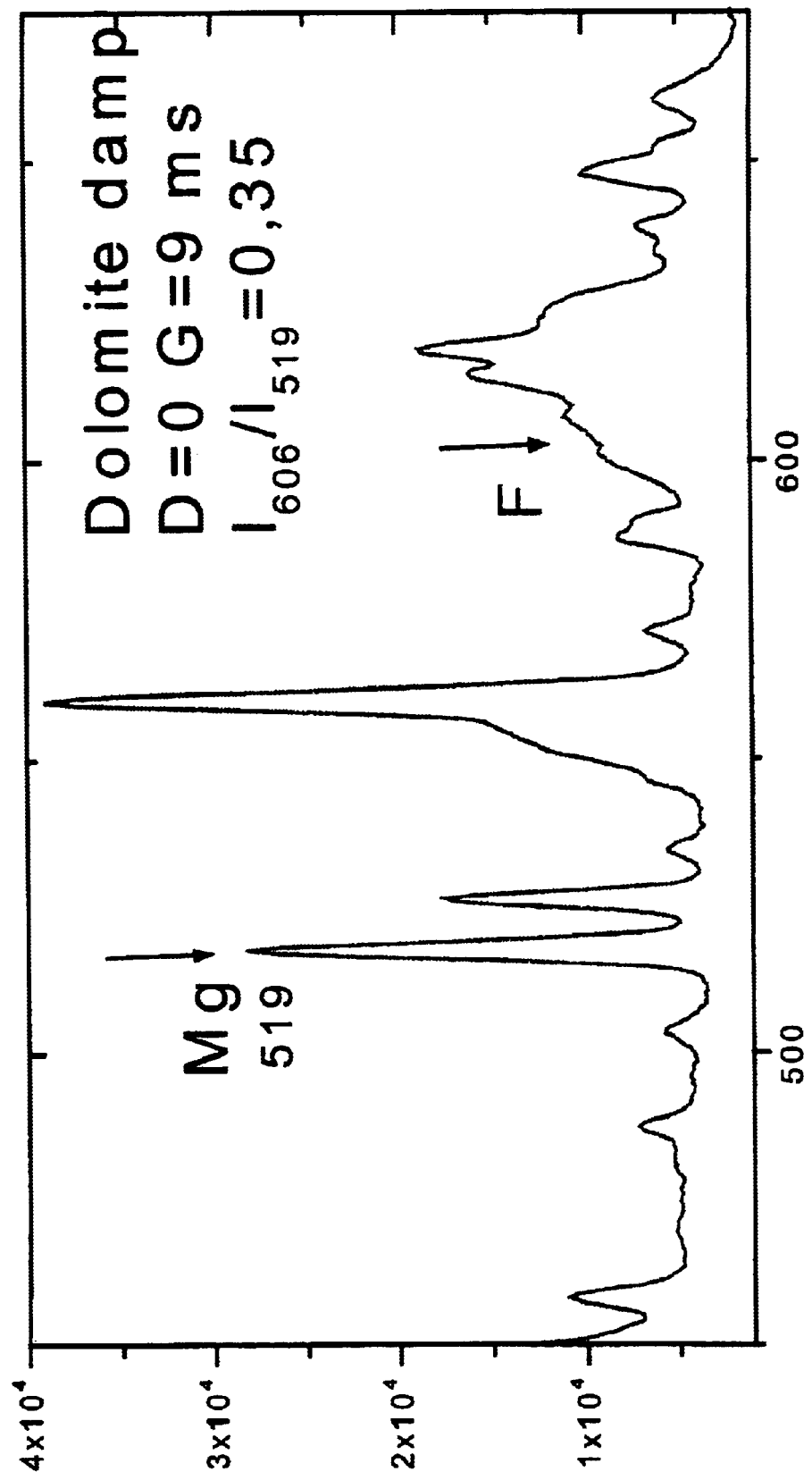
Figure 12C:
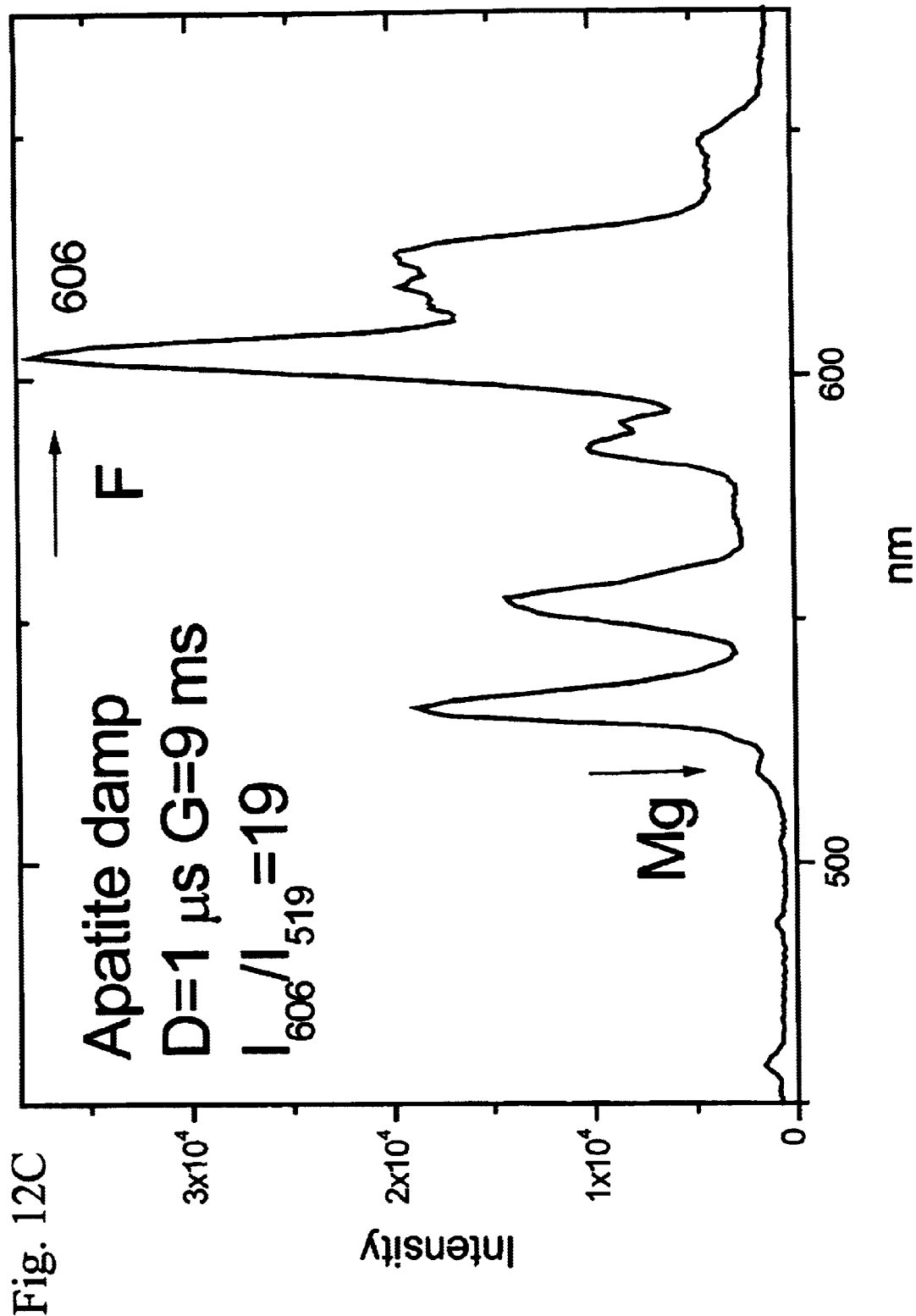
Figure 12D:
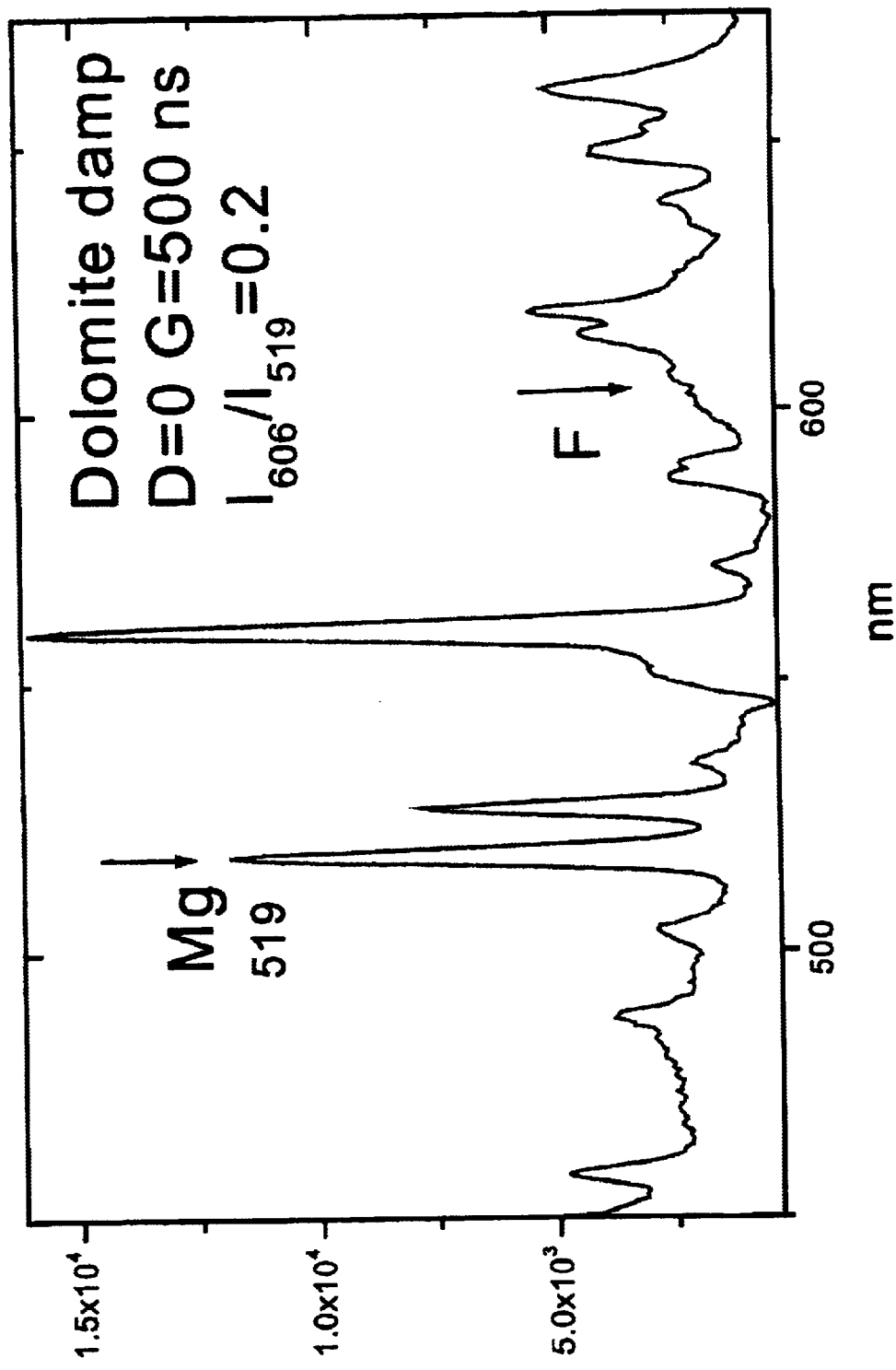
Figure 13A:
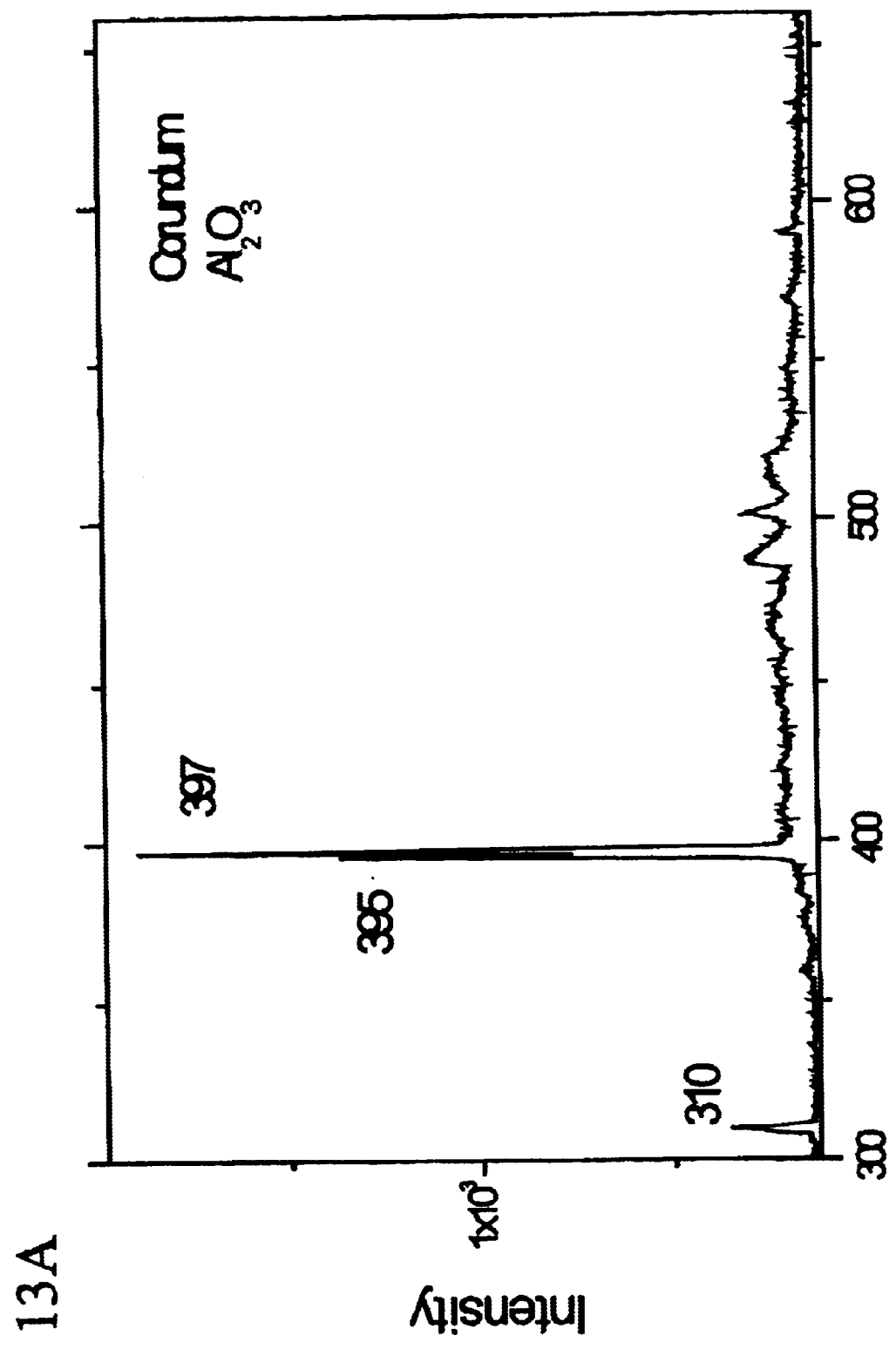
FIGS. 13A–13J are LIBS spectra of various minerals that can be treated by the system and method of the present invention [FIG. 13A, corundum, $Al_2O_3$.
Figure 13B:
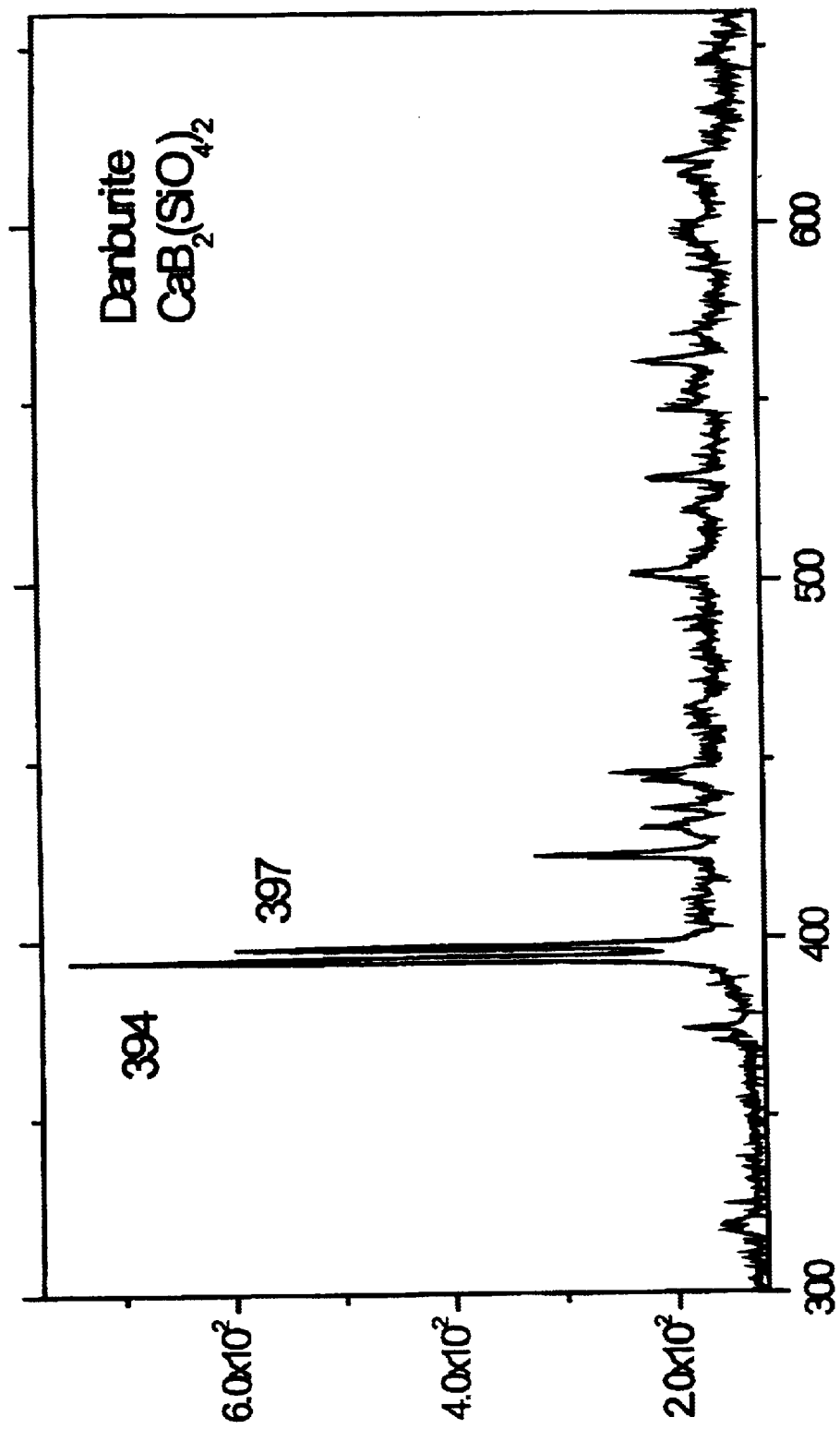
Figure 13C:
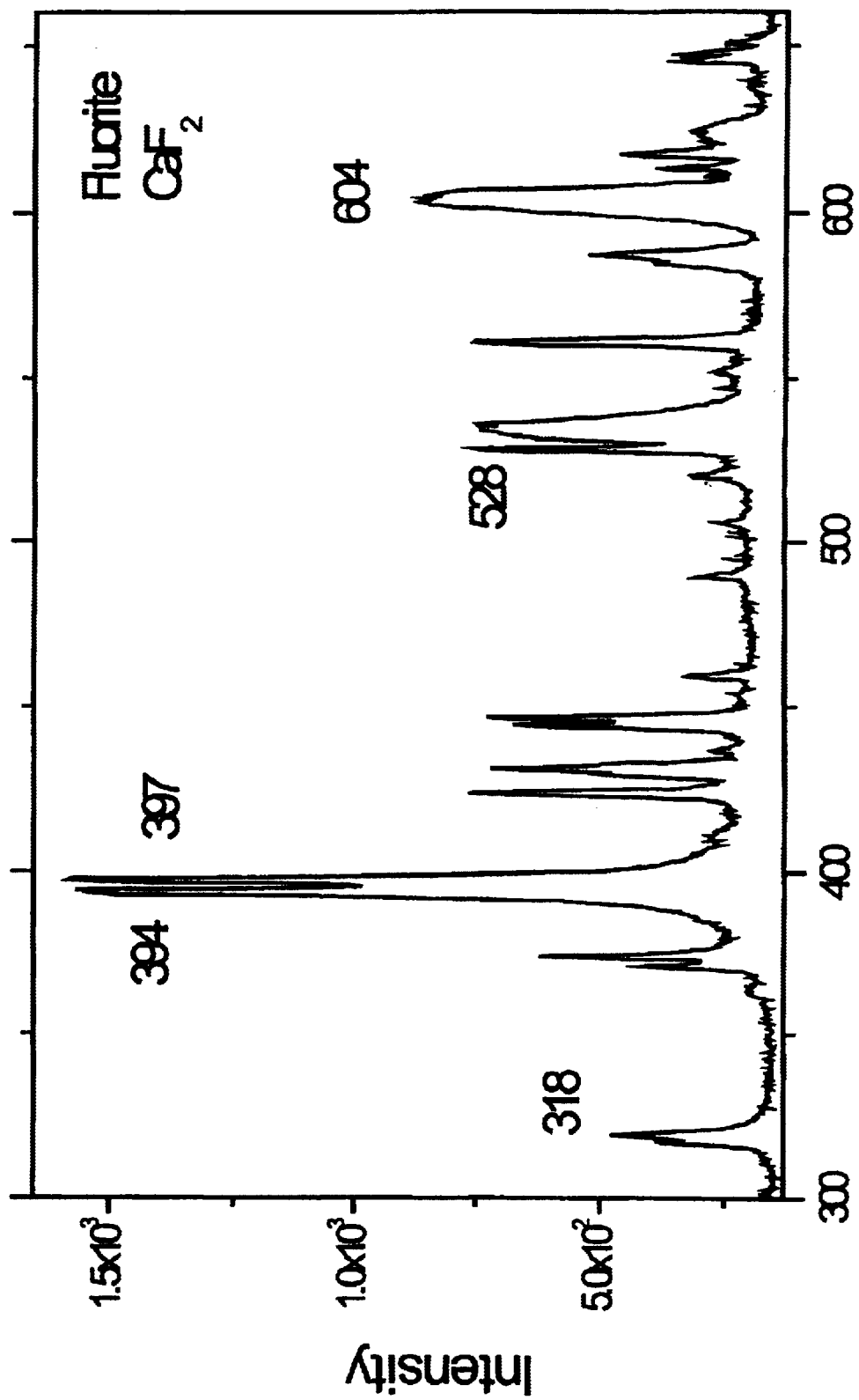
Figure 13D:
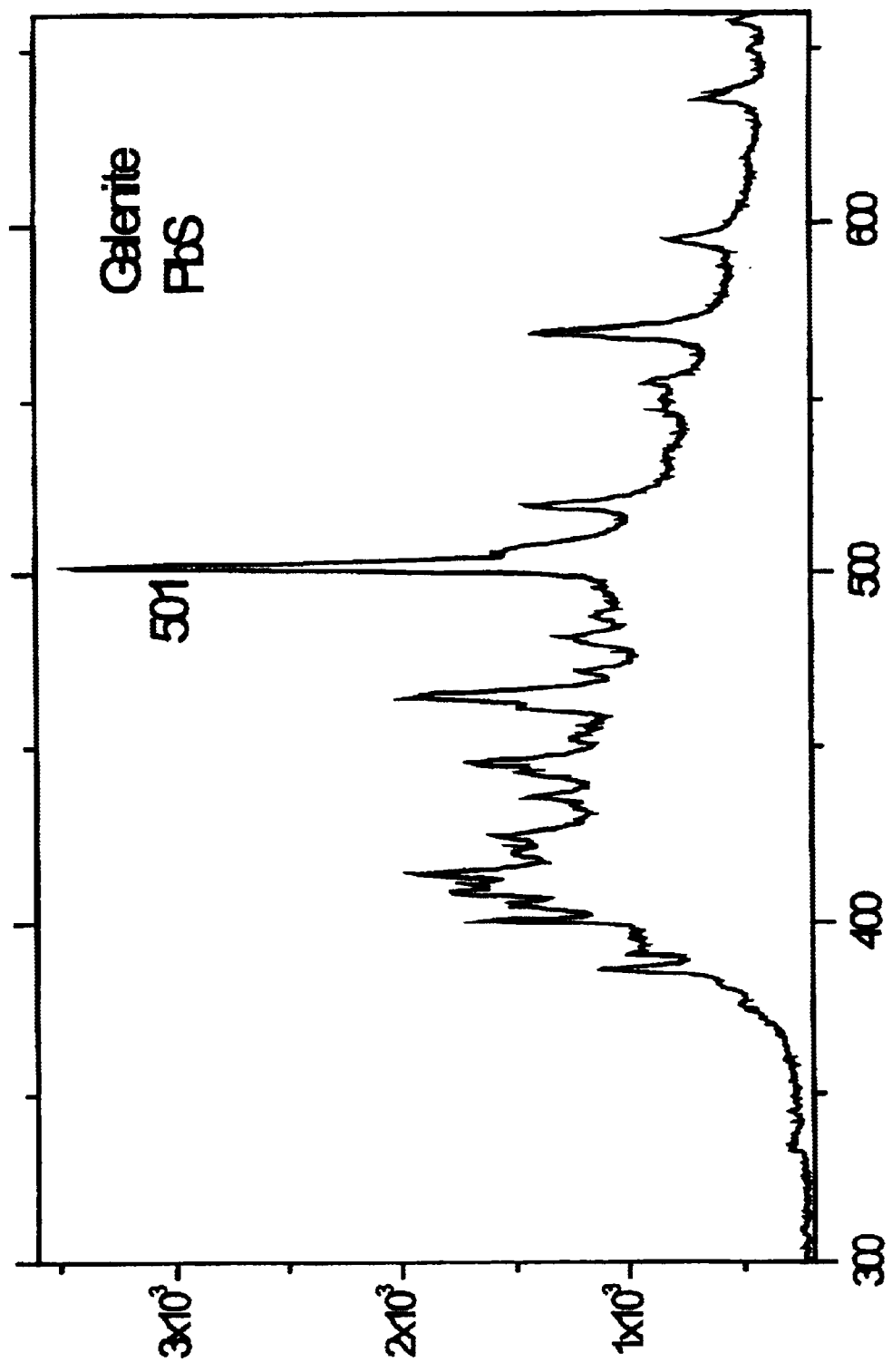
Figure 13E:
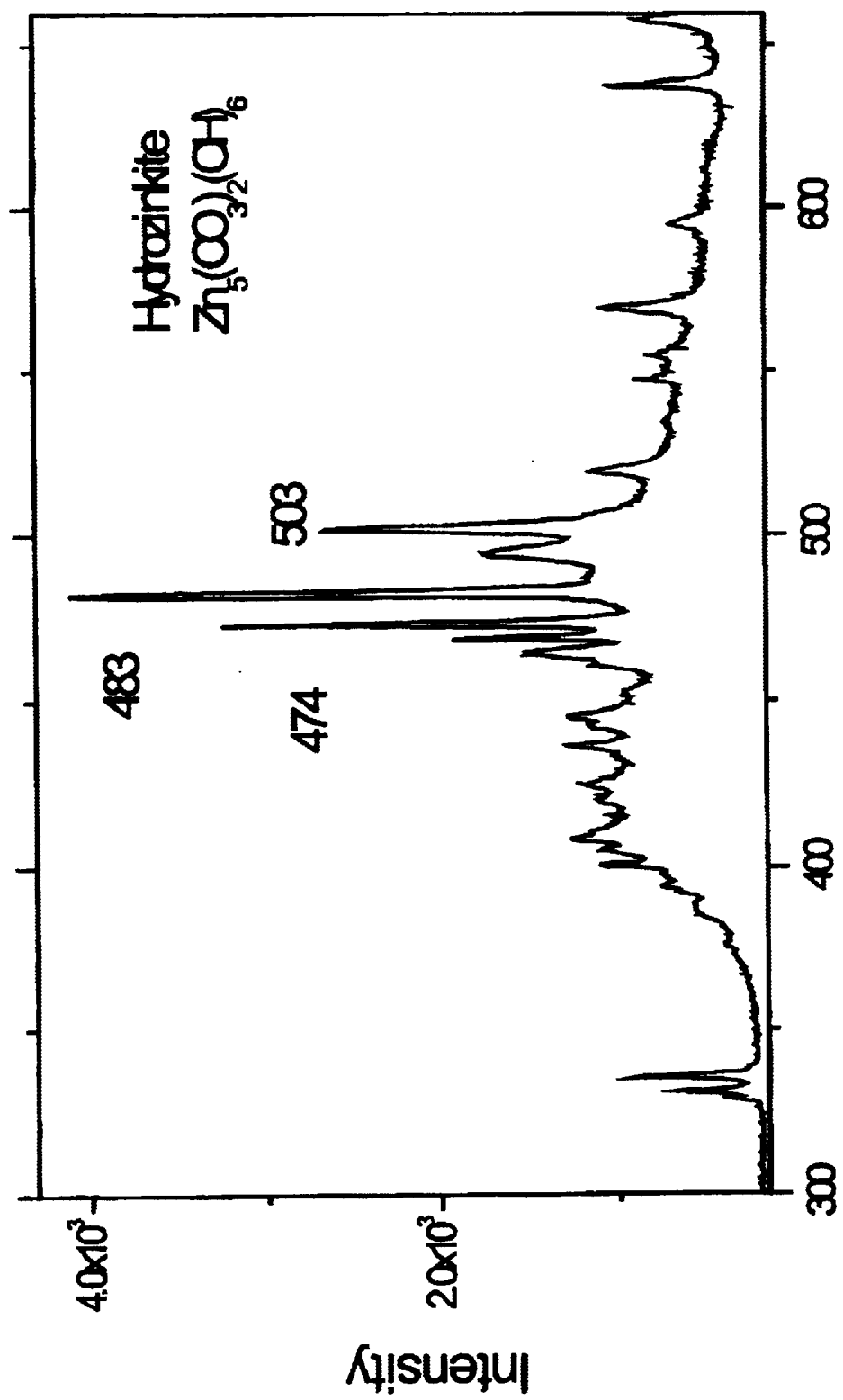
Figure 13F:
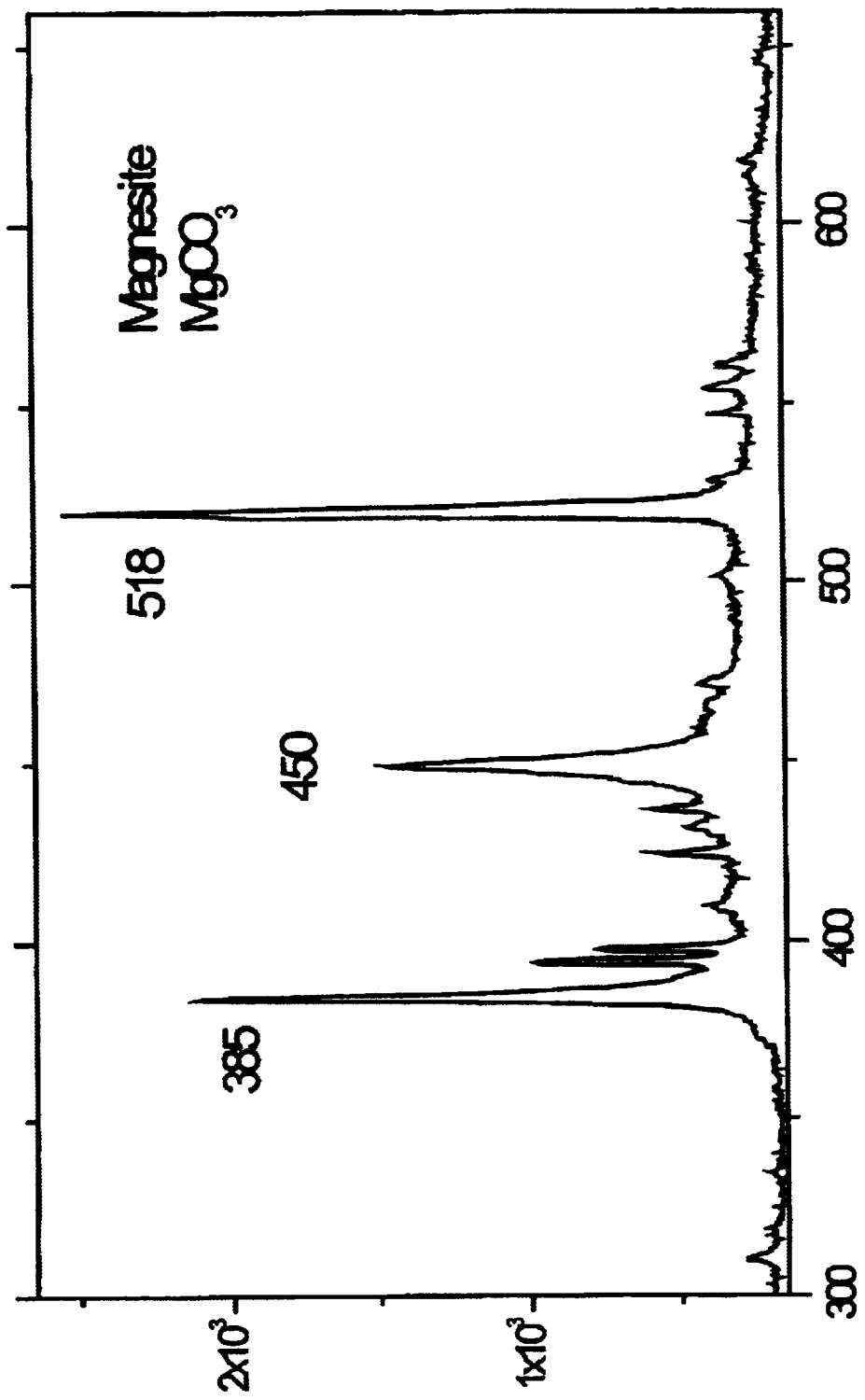
Figure 13G:
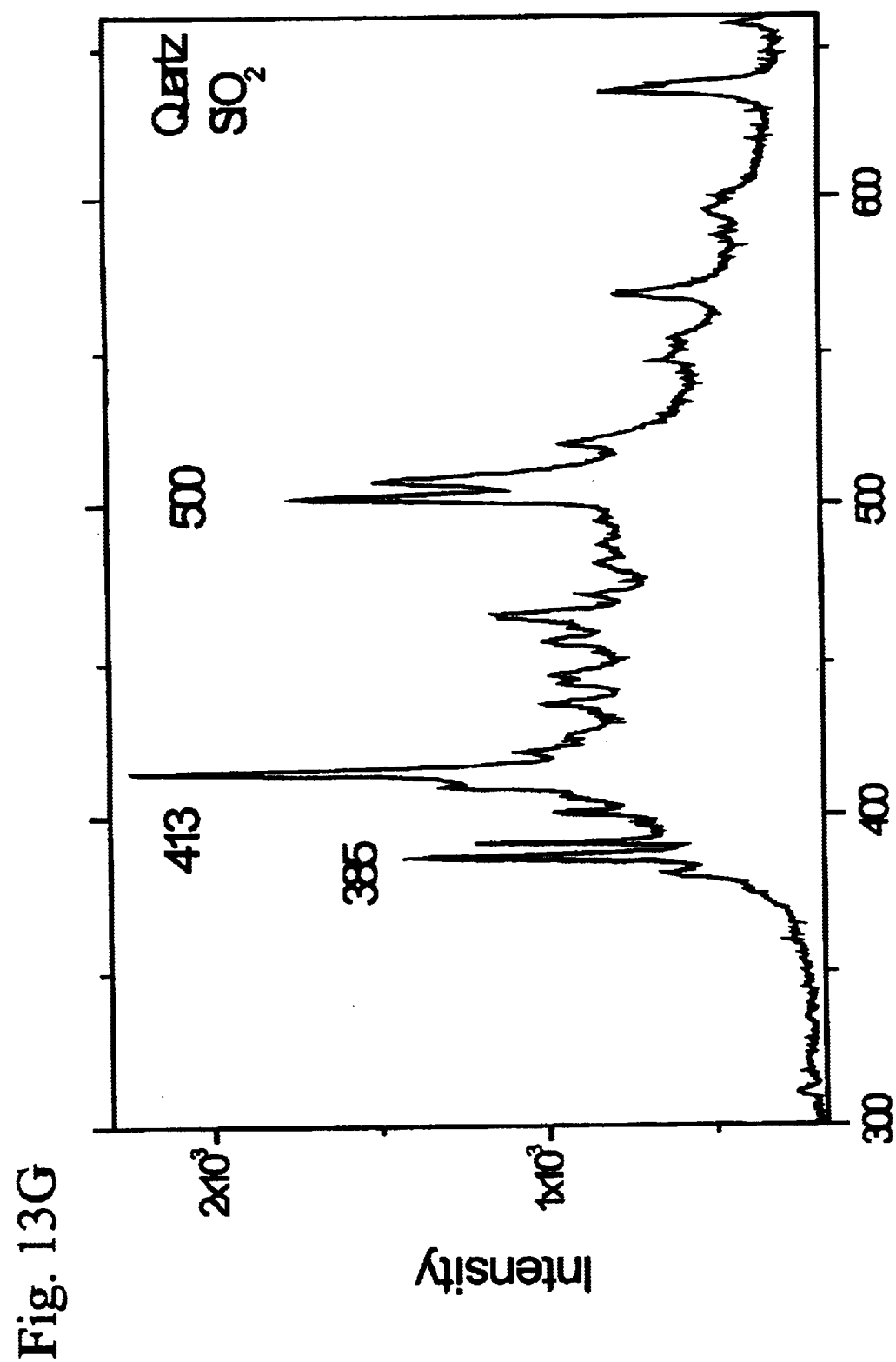
Figure 13H:
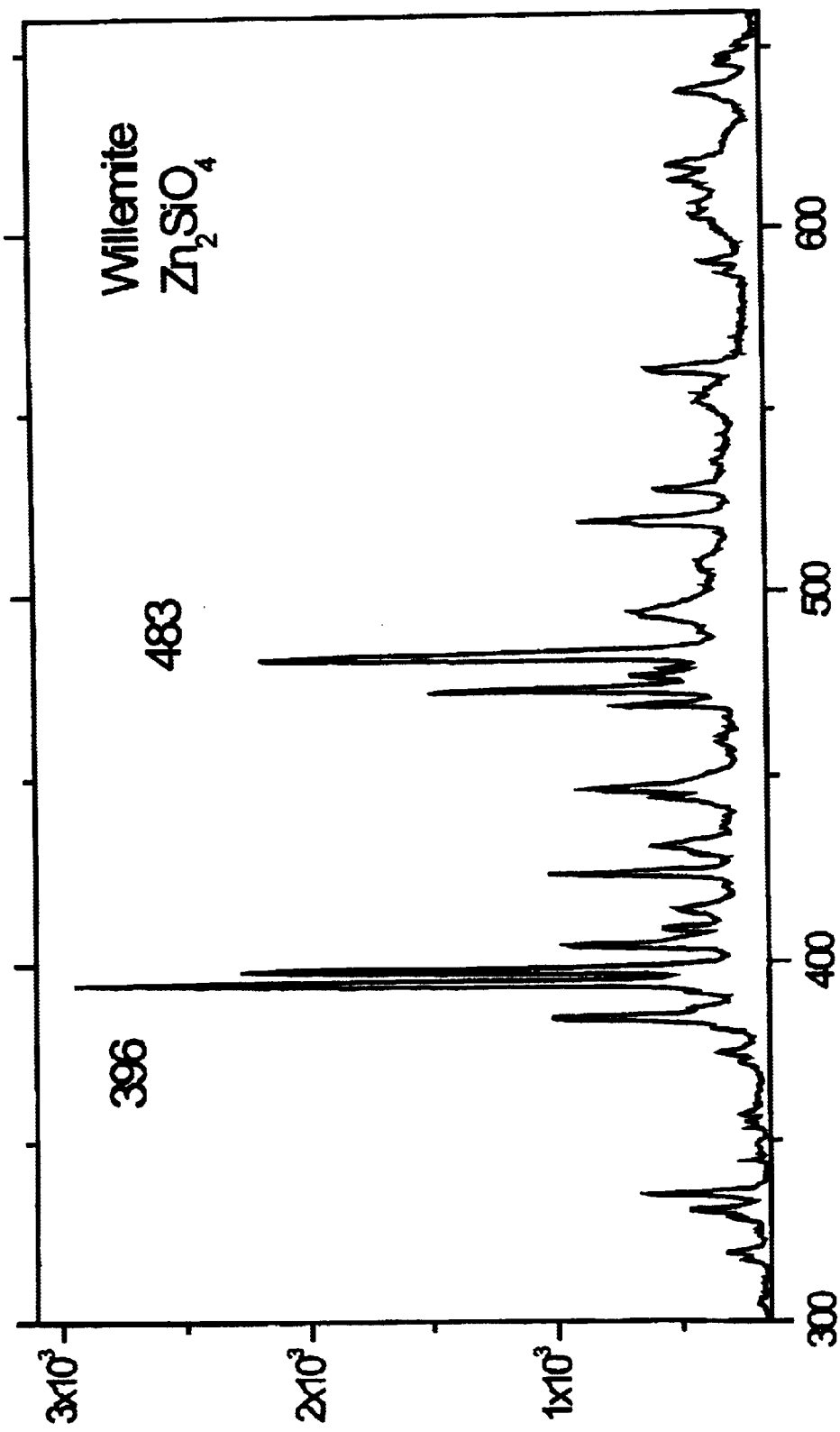
Figure 13I:
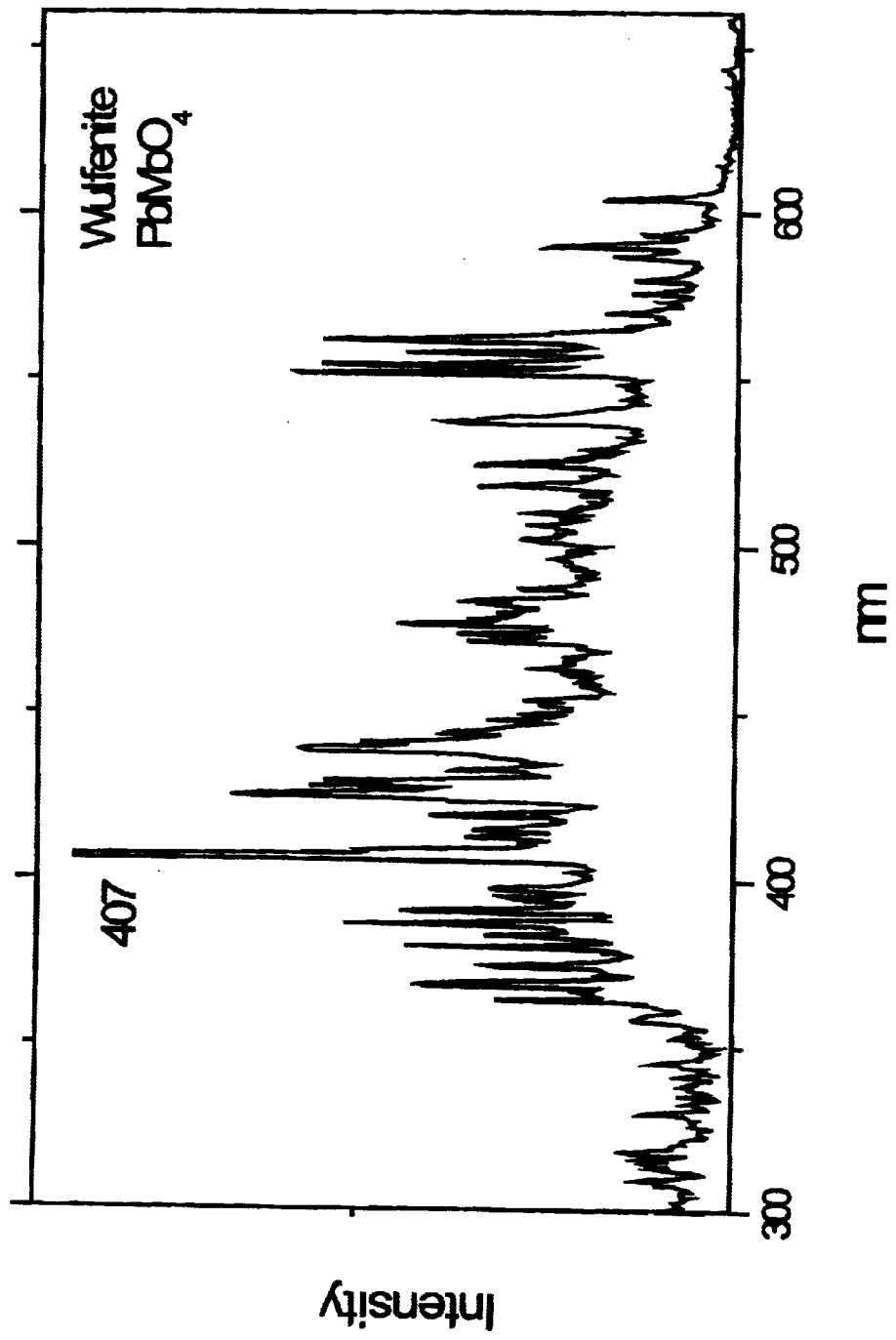
Figure 13J:
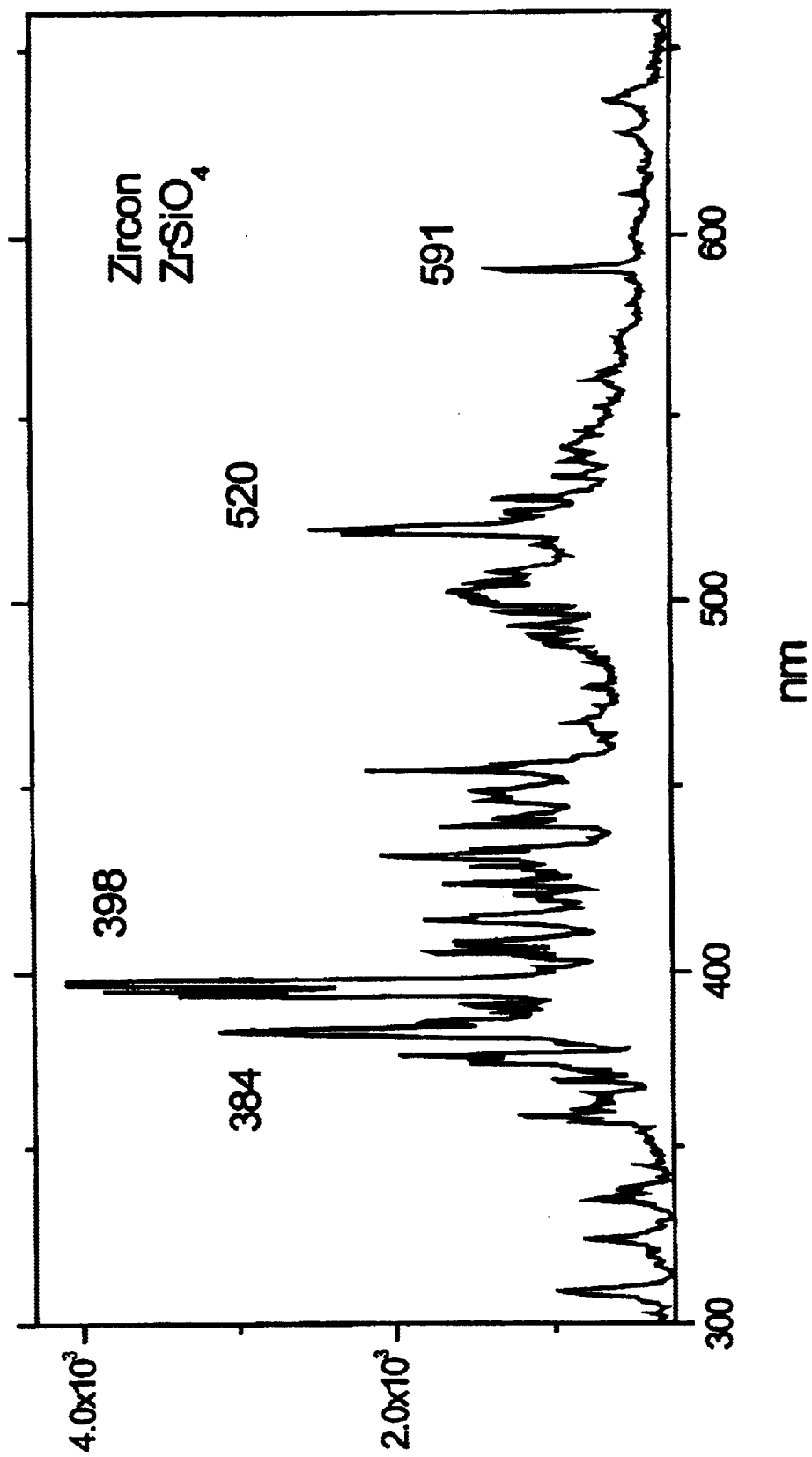

A further embodiment utilizes LIBS. FIGS. 9A–9D and 10A,B are comparison spectra of apatite (FIGS. 9A, 10A), dolomite (FIGS. 9B, 10B), calcite (FIG. 9C), and quartz (FIG. 9D). It may be clearly seen that the line at 604 nm, which is associated with F, belongs only to apatite, while the line at 518 nm, which is associated with Mg, belongs only to dolomite. Thus by using the ratio of the 604- and 518-nm lines ($I_{604}/I_{518}$), confident dolomite versus apatite detection can be made using plasma-induced time-released luminescence spectroscopy (PITRLS). It was found that the signals were very strong with the laser pulse at 5 mJ, and detection was made without delay and gating.

Example 2 Use of LIBS for Apatite and Dolomite Differentiation

The dual PMT system was used to inspect 160 pebbles obtained from a Florida source. These were analyzed in a condition similar to a moving-belt system, namely, from a distance of 1 meter using only one laser pulse. Three groupings were made, and each of these was separated into "bad" as containing dolomite and "good" as being apatite. In addition, an outside laboratory to determine the constituents performed a separate chemical analysis. Those results are contained in Table 3, which illustrates that the "bad" fraction contained mainly dolomite with the mean $/(MgO)//(P_2O_5)$= 0.7, while the "good" fraction is mainly apatite with the mean $/(MgO)//(P_2O_5)$=0.015, clearly 50 times lower.

The identification can also be enhanced by use of time-resolved spectroscopy. As shown in FIGS. 11A–11D, the analytical line of Mg at 518 nm is characterized by a very short decay time of 200 ns. By using a narrow gate of 1 $\mu$s, this may be further enhanced. Under these conditions the intensity of the relatively broad band in the range 600–630 nm associated with carbonate is substantially lower, and the ratio $I_{518}/I_{606}$ is higher. The decay time of the F characteristic line at 606 nm of approximately 500 ns is longer than that for Mg, but it is still relatively strong with the gate of 1 $\mu$s, thus making apatite easily detectable.

One potential problem with analysis of raw ore samples is interference due to water in the material. FIGS. 12A–12D are illustrative spectra of wet samples. A comparison of these with the dry samples of FIGS. 11A–11D clearly shows no interference due to the presence of water.

The description above should not be considered as limiting the scope of the invention, but as merely providing illustration of some of the preferred embodiments of the instant invention. In light of the above description and examples, various other modifications and variations will now become apparent to those of ordinary skill in the art and are therefore considered within the scope of the invention without departing from the spirit and scope of the invention.

What is claimed is:

1. A method for rapid analysis of a compound comprising the steps of:

establishing a spectral signature ratio for at least one predetermined substance, the signature having a first intensity at a first wavelength relative to a second intensity at a second wavelength;

applying pulsed laser energy to the compound whereby plasma is produced;

obtaining the spectral intensity of the plasma at the first and second wavelengths;

and calculating the ratio of the spectral intensity at the first wavelength by the spectral intensity at the second wavelength whereby the presence or absence of the substance may be resolved.

2. The method of claim 1 wherein the compound is analyzed substantially in real-time while in transit.

3. The method of claim 2 wherein the compound moves upon a conveyor belt.

4. The method of claim 1 further comprising the steps of: providing a computational processor; providing a radiation detector adapted to obtain the spectral intensity of the plasma; providing a database of spectral signatures for at least one substance; providing an output means communicatively coupled to the processor; communicatively coupling the radiation detector to the processor; communicatively coupling the processor to the database wherein the spectral intensity is obtained by the radiation detector and measured values for the first and second wavelengths are passed onto the processor which calculates and compares the ratio to the database of spectral signatures and communicates the results to the output means.

5. The method of claim 1 further comprising the step of time-gating the step of obtaining of the spectral intensity of the plasma.

6. The method of claim 1 wherein the compound is a mined ore.

7. The method of claim 1 wherein the compound is ingestible matter.

* * * * *

UNITED STATES PATENT AND TRADEMARK OFFICE
CERTIFICATE OF CORRECTION

PATENT NO. : 6,753,957 B1
DATED : June 22, 2004
INVENTOR(S) : Michael Graft and Lev Nagli It is certified that error appears in the above-identified patent and that said Letters Patent is hereby corrected as shown below:

<u>Title page,</u>
Item [75], Inventor, "Michael Graft" should be changed to -- Michael Gaft --

Signed and Sealed this

Nineteenth Day of April, 2005

JON W. DUDAS
*Director of the United States Patent and Trademark Office*